(12) United States Patent
Laurent et al.

(10) Patent No.: US 9,284,318 B2
(45) Date of Patent: Mar. 15, 2016

(54) PROTEIN KINASE INHIBITORS

(75) Inventors: Alain Laurent, Montreal (CA); Yannick Rose, Montreal (CA); Stephen Morris, Montreal (CA); James Jaquith, Montreal (CA)

(73) Assignee: Pharmascience, Inc., Montreal (CA)

( * ) Notice: Subject to any disclaimer, the term of this patent is extended or adjusted under 35 U.S.C. 154(b) by 113 days.

(21) Appl. No.: 14/008,977

(22) PCT Filed: Apr. 3, 2012

(86) PCT No.: PCT/CA2012/000285
§ 371 (c)(1),
(2), (4) Date: Feb. 18, 2015

(87) PCT Pub. No.: WO2012/135937
PCT Pub. Date: Oct. 11, 2012

(65) Prior Publication Data
US 2015/0210696 A1    Jul. 30, 2015

Related U.S. Application Data

(60) Provisional application No. 61/471,322, filed on Apr. 4, 2011.

(51) Int. Cl.
```
C07D 487/04    (2006.01)
C07D 491/147   (2006.01)
C07C 253/30    (2006.01)
C07C 269/06    (2006.01)
C07D 209/52    (2006.01)
C07D 261/14    (2006.01)
C07D 413/12    (2006.01)
```

(52) U.S. Cl.
CPC ............ C07D 487/04 (2013.01); C07C 253/30 (2013.01); C07C 269/06 (2013.01); C07D 209/52 (2013.01); C07D 261/14 (2013.01); C07D 413/12 (2013.01); C07D 491/147 (2013.01)

(58) Field of Classification Search
CPC .................... C07D 487/04; C07D 491/147
USPC .................... 514/267; 544/250, 251
See application file for complete search history.

(56) References Cited

FOREIGN PATENT DOCUMENTS

| | | |
|---|---|---|
| CA | 2698018 A1 | 3/2009 |
| CA | 2730319 A1 | 1/2010 |
| WO | 92/06094 A1 | 4/1992 |
| WO | 2010/006032 A1 | 1/2010 |

OTHER PUBLICATIONS

Crane, et al., Synthesis of Pyrrolo[3,2-d]pyrimidines from Furazano[3,4-d]pyrimidines via Enolate and Ene Adducts, J. Org. Chem., 45, pp. 3827-3831 (1980).*
European Patent Application No. 12767447.1, Extended European Search Report and Written Opinion mailed Jul. 17, 2014, 6 pages.
Chakrabarti et al., "Heteroarenobenzodiazepines. 3. 4-Piperazinyl-10H-thieno[2,3-b][1,5]Benzodiazepines as Potential Neuroleptics", Journal of Medicinal Chemistry, vol. 23, No. 8, Jan. 1, 1980, pp. 878-884.
Crane et al., "Synthesis of Pyrrolo[3,2-d]Pyrimidines from Furazano[3,4-d]Pyrimidines via Enolate and ene Adducts", The Journal of Organic Chemistry, vol. 45, 1980, pp. 3827-3831.
J. Med. Chem.. 1999. 42 (26). pp. 5464-5474. H.D. Hollis Showalter at al. "Tyrosine Kinase Inhibitors. 16. 6.5.6-Tricyclic Benzothieno[3.2-d]pyrimidines and Pyrimido[5.4-b]- and -[4.5-b]indoles as Potent Inhibitors of the Epidermal Growth Factor Receptor Tyrosine Kinase".
International Search Report dated Jun. 21, 2012 for International Patent Application PCT/CA2012/000285 filed on Apr. 3, 2012.
Written Opinion Received for Singapore Patent Application No. 2013068317, mailed on Oct. 16, 2014, 8 pages.

* cited by examiner

*Primary Examiner* — Erich A Leeser
(74) *Attorney, Agent, or Firm* — Morgan, Lewis & Bockius LLP

(57) ABSTRACT

The present invention relates to novel kinase inhibitors. Compounds of this class have been found to be effective inhibitors of protein kinases, including members of PDGFR and VEGFR families.

20 Claims, No Drawings

PROTEIN KINASE INHIBITORS

This application is a National Stage Entry of International Application No. PCT/CA2012/000285 filed Apr. 3, 2012, which claims priority to U.S. Provisional Application No. 61/471,322 filed Apr. 4, 2011. The entire disclosure of each of the foregoing references is incorporated herein in their entirety.

FIELD OF INVENTION

The present invention relates to novel kinase inhibitors. In particular, the present invention relates to inhibitors of receptor tyrosine kinases such as members of the platelet-derived growth factor receptor (PDGFR), including cFMS (CSF-1R) and FMS-like tyrosine kinase 3 (FLT3) which normally regulate cellular function through activation by external ligands.

BACKGROUND OF THE INVENTION

Protein kinases are a large group of intracellular and transmembrane signaling proteins in eukaryotic cells (for example, see Manning, G., D. B. Whyte, et al. (2002). "The protein kinase complement of the human genome." *Science* 298(5600): 1912-1934). These enzymes are responsible for transfer of the terminal (gamma) phosphate from ATP to specific amino acid residues of target proteins. Phosphorylation of specific amino-acid residues of target proteins can modulate their activity leading to profound changes in cellular signaling and metabolism. Kinases can be found in the cell membrane, cytosol and organelles such as the nucleus and are responsible for mediating multiple cellular functions including metabolism, cellular growth and division, cellular signaling, modulation of immune responses, and apoptosis. Cell surface receptors with protein tyrosine kinase activity are known as receptor tyrosine kinases. This large family of proteins includes growth factor receptors with diverse biological activity (for example, see Lemmon, M. A. and J. Schlessinger (2010). "Cell signaling by receptor tyrosine kinases." *Cell* 141(7): 1117-1134).

Aberrant activation or excessive expression of various protein kinases are implicated in the mechanism of multiple diseases and disorders characterized by benign and malignant proliferation, excess angiogenesis, as well as diseases resulting from inappropriate activation of the immune system. Thus, inhibitors of select kinases or kinase families are expected to be useful in the treatment of diseases and disorders such as: cancer, arthritis, myeloproliferative disorders, cardiac hypertrophy, lung fibrosis, hepatic fibrosis, atherosclerosis, restenosis, glomerulonephritis, psoriasis, lupus, multiple sclerosis, macular degeneration, asthma, reactive synoviotides and the like (for example, see: Chitu, V. and E. R. Stanley (2006). "Colony-stimulating factor-1 in immunity and inflammation." Curr *Opin Immunol* 18(1): 39-48; Mitchell-Jordan, S. A., T. Holopainen, et al. (2008). "Loss of Bmx nonreceptor tyrosine kinase prevents pressure overload-induced cardiac hypertrophy." *Circ Res* 103(12): 1359-1362; Uemura, Y., H. Ohno, et al. (2008). "The selective M-CSF receptor tyrosine kinase inhibitor Ki20227 suppresses experimental autoimmune encephalomyelitis." *J Neuroimmunol* 195(1-2): 73-80; Cohen, P. (2009). "Targeting protein kinases for the development of anti-inflammatory drugs." *Curr Opin Cell Biol* 21(2): 317-324; Menke, J., W. A. Rabacal, et al. (2009). "Circulating CSF-1 promotes monocyte and macrophage phenotypes that enhance lupus nephritis." *J Am Soc Nephrol* 20(12): 2581-2592; Grimminger, F., R. T. Schermuly, et al. (2010). "Targeting non-malignant disorders with tyrosine kinase inhibitors." *Nat Rev Drug Discov* 9(12): 956-970; Hilgendorf, I., S. Eisele, et al. (2011). "The oral spleen tyrosine kinase inhibitor fostamatinib attenuates inflammation and atherogenesis in low-density lipoprotein receptor-deficient mice." *Arterioscler Thromb Vasc Biol* 31(9): 1991-1999; Sharma, P. S., R. Sharma, et al. (2011). "VEGF/VEGFR pathway inhibitors as anti-angiogenic agents: present and future." *Curr Cancer Drug Targets* 11(5): 624-653; Fabbro, D., S. W. Cowan-Jacob, et al. (2012). "Targeting cancer with small-molecular-weight kinase inhibitors." *Methods Mol Biol* 795: 1-34).

Examples of kinases that can be targeted to modulate disease include receptor tyrosine kinases such as members of the platelet-derived growth factor receptor (PDGFR) and vascular endothelial growth factor receptor (VEGFR) families.

The PDGFR family of receptor tyrosine kinases includes cFMS (CSF-1R) and FMS-like tyrosine kinase 3 (FLT3) which normally regulate cellular function through activation by external ligands.

cFMS is a transmembrane receptor kinase that binds to colony-stimulating-factor-1 (CSF-1) and interleukin (IL)-34 (IL-34) (for example, see Chihara, T., S. Suzu, et al. (2010). "IL-34 and M-CSF share the receptor Fms but are not identical in biological activity and signal activation." *Cell Death Differ* 17(12): 1917-1927) and which plays an important role in macrophage, monocyte and osteoclast biology. The cFMS-CSF-1 pathway is upregulated in various human diseases that involve chronic macrophage activation. Activation of cFMS plays a central role in arthritis through its role in differentiation of monocytes (for example, see Paniagua, R. T., A. Chang, et al. (2010). "c-Fms-mediated differentiation and priming of monocyte lineage cells play a central role in autoimmune arthritis." *Arthritis Res Ther* 12(1): R32) and inhibition of cFMS has been shown to be effective in pre-clinical models of arthritis (for example, see: Conway, J. G., H. Pink, et al. (2008). "Effects of the cFMS kinase inhibitor 5-(3-methoxy-4-((4-methoxybenzyl)oxy)benzyl)pyrimidine-2,4-diamine (GW2580) in normal and arthritic rats." *J Pharmacol Exp Ther* 326(1): 41-50); Ohno, H., Y. Uemura, et al. (2008). "The orally-active and selective c-Fms tyrosine kinase inhibitor Ki20227 inhibits disease progression in a collagen-induced arthritis mouse model." *Eur J Immunol* 38(1): 283-291; Huang, H., D. A. Hutta, et al. (2009). "Pyrido [2,3-d]pyrimidin-5-ones: a novel class of antiinflammatory macrophage colony-stimulating factor-1 receptor inhibitors." *J Med Chem* 52(4): 1081-1099; and Illig, C. R., C. L. Manthey, et al. (2011). "Optimization of a potent class of arylamide colony-stimulating factor-1 receptor inhibitors leading to anti-inflammatory clinical candidate 4-cyano-N-[2-(1-cyclohexen-1-yl)-4-[1-[(dimethylamino)acetyl]-4-piperidinyl]phenyl]-1H-imidazole-2-carboxamide (JNJ-28312141)." *J Med Chem* 54(22): 7860-7883) suggesting that cFMS kinase inhibitors may be useful in treatment of human arthritis. cFMS inhibition has also been shown to be effective in a pre-clinical model of multiple sclerosis (Uemura, Y., H. Ohno, et al. (2008). "The selective M-CSF receptor tyrosine kinase inhibitor Ki20227 suppresses experimental autoimmune encephalomyelitis." *J Neuroimmunol* 195(1-2): 73-80).

Inhibitors of cFMS are expected to be therapeutically useful in treatment of tenosynovial gain cell tumor, pigmented villonodular synovitis and other reactive synovitides which are often characterized by high levels of CSF-1 expression (for example, see Cupp, J. S., M. A. Miller, et al. (2007). "Translocation and expression of CSF1 in pigmented villonodular synovitis, tenosynovial giant cell tumor, rheumatoid arthritis and other reactive synovitides." *Am J Surg Pathol* 31(6): 970-976). Preclinical studies using antibodies targeting CSF-1 predict that cFMS inhibitors may be useful in treating these human diseases (Cheng, H., P. W. Clarkson, et al. (2010). "Therapeutic Antibodies Targeting CSF1 Impede Macrophage Recruitment in a Xenograft Model of Tenosynovial Giant Cell Tumor." *Sarcoma* 2010: 174528).

cFMS is important in osteoclast differentiation and function and therefore cFMS inhibition may be useful in modulating osteoclast function in arthritis as well as in the formation and progression of bone metastases (for example, see Manthey, C. L., D. L. Johnson, et al. (2009). "JNJ-28312141, a novel orally active colony-stimulating factor-1 receptor/FMS-related receptor tyrosine kinase-3 receptor tyrosine kinase inhibitor with potential utility in solid tumors, bone metastases, and acute myeloid leukemia." *Mol Cancer Ther* 8(11): 3151-3161). Secretion of growth factors and immunosuppressive cytokines by tumor-associated macrophages suggests that targeting their function through inhibition of cFMS could be a useful anti-cancer therapy (for example, see Bingle, L., N. J. Brown, et al. (2002). "The role of tumour-associated macrophages in tumour progression: implications for new anticancer therapies." *J Pathol* 196(3): 254-265). Accordingly, cFMS inhibition or knockdown has shown efficacy in tumor models through inhibition of tumor associated macrophage (for example, see Aharinejad, S., P. Paulus, et al. (2004). "Colony-stimulating factor-1 blockade by antisense oligonucleotides and small interfering RNAs suppresses growth of human mammary tumor xenografts in mice." *Cancer Res* 64(15): 5378-5384; and Manthey, Johnson et al. 2009) suggesting that cFMS inhibitors may have utility in the treatment of human cancer.

FLT3 is mutated in approximately 30% of adult patients with acute myeloid leukemia (AML) and has a significant impact on prognosis (for example, see Gilliland, D. G. and J. D. Griffin (2002). "The roles of FLT3 in hematopoiesis and leukemia." *Blood* 100(5): 1532-1542). Accordingly, inhibition of FLT3 is expected to be useful in the treatment of malignancies such as AML (for example, see: Knapper, S. (2011). "The clinical development of FLT3 inhibitors in acute myeloid leukemia." *Expert Opin Investig Drugs* 20(10): 1377-1395; Pemmaraju, N., H. Kantarjian, et al. (2011). "FLT3 inhibitors in the treatment of acute myeloid leukemia: the start of an era?" *Cancer* 117(15): 3293-3304). Additionally, FLT3-ligand is implicated in induction and progression of arthritis suggesting that inhibitors of FLT3 may be useful in the treatment of arthritis (for example, see Dehlin, M., M. Bokarewa, et al. (2008). "Intra-articular fms-like tyrosine kinase 3 ligand expression is a driving force in induction and progression of arthritis." *PLoS One* 3(11): e3633).

Inhibition of members of the vascular endothelial growth factor (VEGF) and TIE2 families are expected to have anti-angiogenic effects which may be useful in the treatment of many diseases or disorders including cancer and arthritis (for example, see: Timar, J. and B. Dome (2008). "Antiangiogenic drugs and tyrosine kinases." *Anticancer Agents Med Chem* 8(5): 462-469; Huang, H., A. Bhat, et al. (2010). "Targeting the ANGPT-TIE2 pathway in malignancy." *Nat Rev Cancer* 10(8): 575-585; and Huang, H., J. Y. Lai, et al. (2011). "Specifically targeting angiopoietin-2 inhibits angiogenesis, Tie2-expressing monocyte infiltration, and tumor growth." *Clin Cancer Res* 17(5): 1001-1011).

Fibroblast growth factor receptor 1 (FGFR1) provides a further example of a kinase that may be targeted for therapeutic effect. FGFR1 is amplified in select subsets of cancers (for example, see: Courjal, F., M. Cuny, et al. (1997). "Mapping of DNA amplifications at 15 chromosomal localizations in 1875 breast tumors: definition of phenotypic groups." *Cancer Res* 57(19): 4360-4367; and Tsujimoto, H., H. Sugihara, et al. (1997). "Amplification of growth factor receptor genes and DNA ploidy pattern in the progression of gastric cancer." *Virchows Arch* 431(6): 383-389) and inhibition of FGFR1 has shown efficacy in preclinical models of cancer (for example, see Gozgit, J. M., M. J. Wong, et al. (2012). "Ponatinib (AP24534), a multi-targeted pan-FGFR inhibitor with activity in multiple FGFR-amplified or mutated cancer models." *Mol Cancer Ther*. 11(3):690-9).

Inhibition of kinases using small molecule inhibitors has successfully led to several approved therapeutic agents used in the treatment of human conditions. Herein, we disclose a novel family of kinase inhibitors. Further, we demonstrate that modifications in compound substitution can influence kinase selectivity and therefore the biological function of that agent and disease state for which it may be useful as a therapeutic agent.

SUMMARY OF THE INVENTION

The present invention relates to a new class of 5-aryl-5H-pyrrolo[3,2-d]pyrimidin-4-amines which contain 6,7-fuse alkyl and heteroalkyl ring systems. Compounds of this class have been found to be effective inhibitors of protein kinases, more particularly including cFMS, Flt3, KDR, and FGFR1.

Provided herein is a compound of Formula 1:

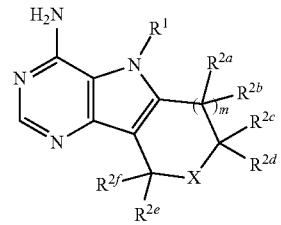

Formula 1 m is an integer from 0 to 1;
n is an integer for 0 to 2;
$R^1$ is selected from alkyl, heteroalkyl, carbocyclyl, or heterocyclyl;
$R^1$ is also selected from aryl, or heteroaryl, wherein the aryl and heteroaryl may be further substituted by the groups selected from:
  1) Halogen,
  2) Alkoxy,
  3) Amino,
  4) —N(H)C(O)O-alkyl
  5) —N(H)SO$_2$-aryl,
  6) —N(H)SO$_2$-heteroaryl,
  7) —N(H)CON(H)-aryl,
  8) and —N(H)CON(H)-heteroaryl;
$R^{2a}$, $R^{2b}$, $R^{2c}$, $R^{2d}$, $R^{2e}$, $R^{2f}$ are independently selected from hydrogen, alkyl, heteroalkyl, carbocyclyl, heterocyclyl, aryl, heteroaryl. $R^{2a}$ and $R^{2b}$, $R^{2c}$ and $R^{2d}$ or $R^{2e}$ and $R^{2f}$ can be fused to form a 3 to 8 membered cycloalkyl or heterocyclyl ring system;
X is selected from CH$_2$, O, S(O)$_n$, NR$^3$;
$R^3$ is selected from hydrogen, alkyl, heteroalkyl, carbocyclyl, heterocyclyl, aryl, heteroaryl, —C(O)R$^4$, —C(O)OR$^4$, —S(O)$_2$R$^4$, —C(O)NR$^4$R$^5$, —S(O)$_2$NR$^4$R$^5$, —C(S)NR$^4$R$^5$;
$R^4$ and $R^5$ are independently selected from alkyl, heteroalkyl, carbocyclyl, heterocyclyl, aryl, heteroaryl or R$^4$ and R$^5$ can be fused to form a 3 to 8 membered heterocyclyl ring system;

In certain embodiments, compounds of Formula 1 may be further defined as:
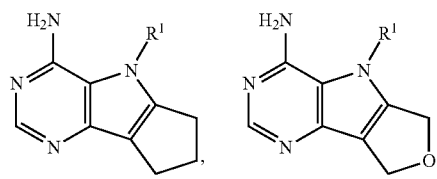
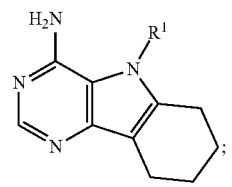
Wherein R¹ may be defined as:
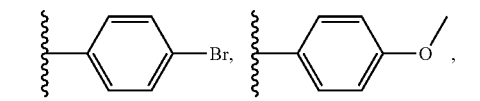
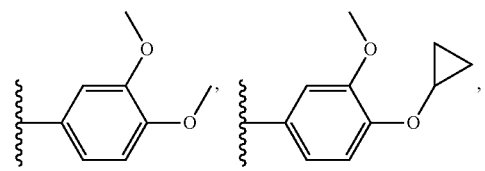
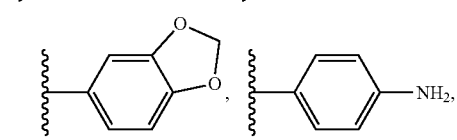
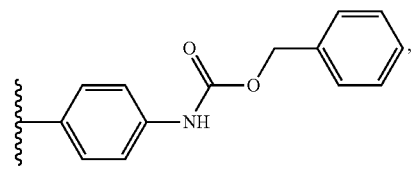
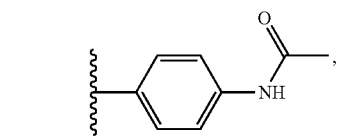
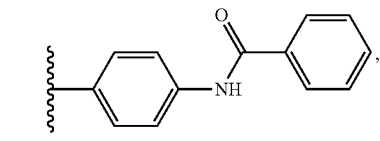
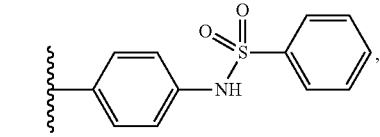
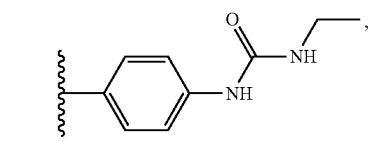
-continued
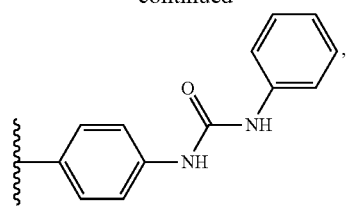
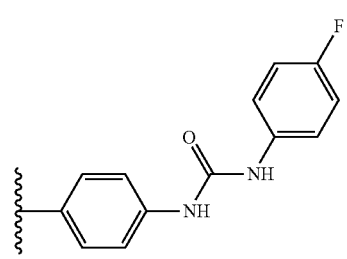
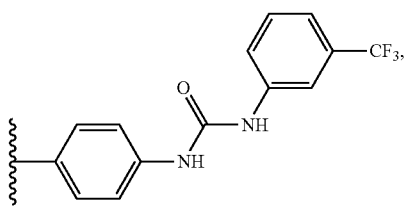
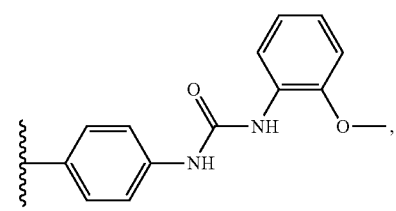
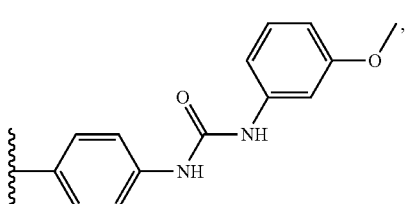
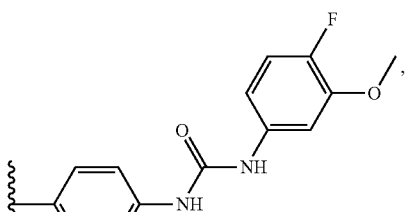
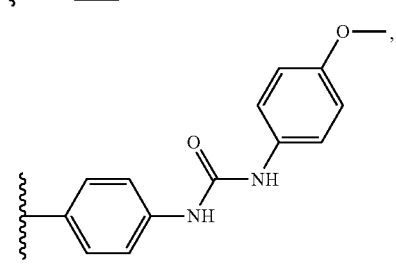

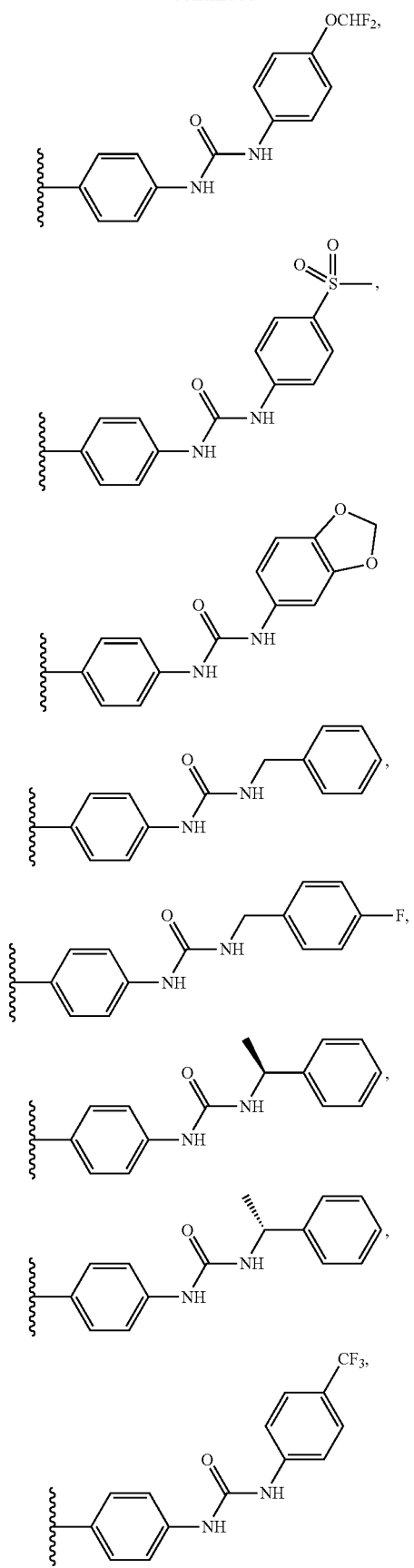
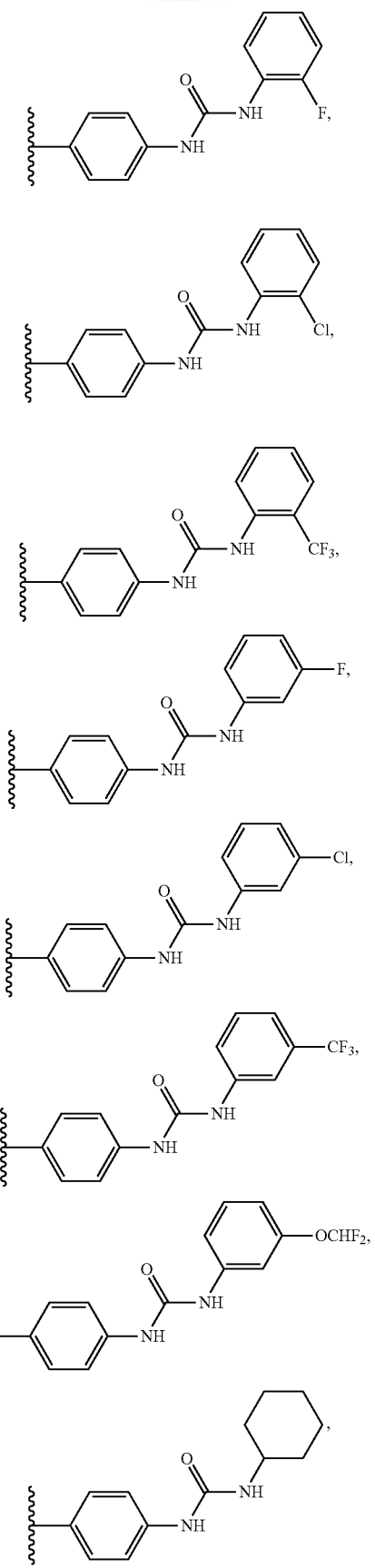

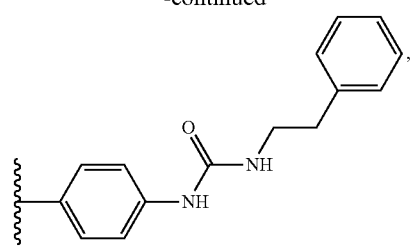
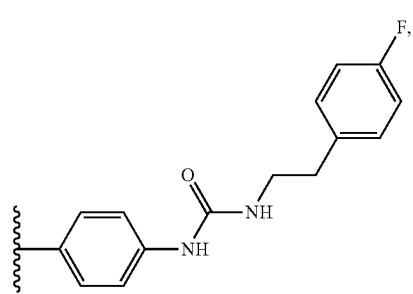
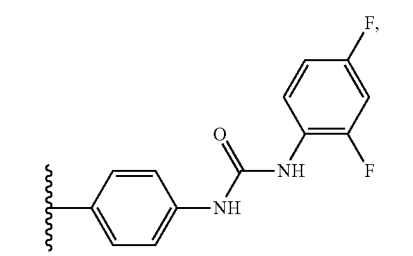
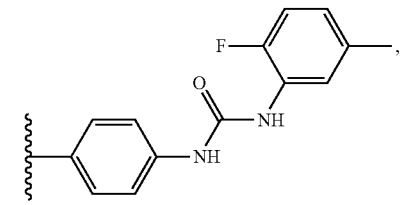
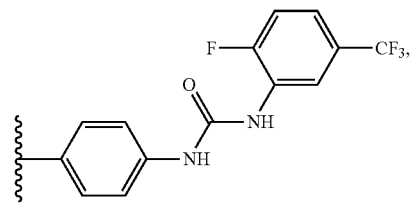
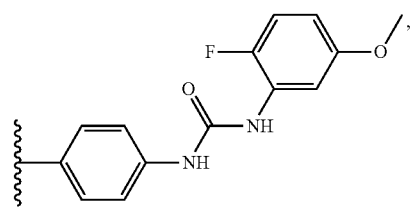
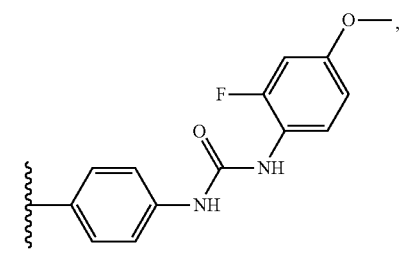
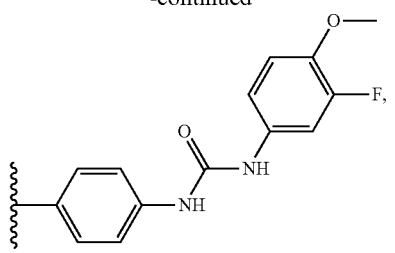
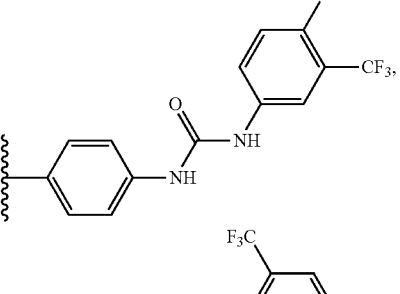
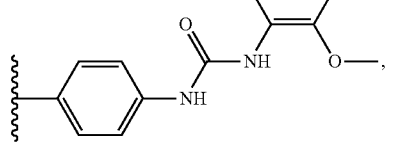
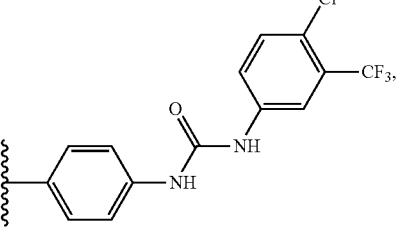
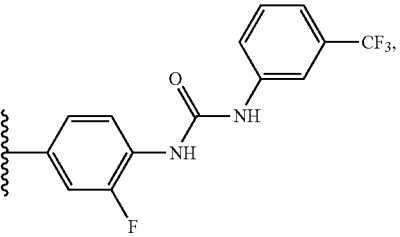
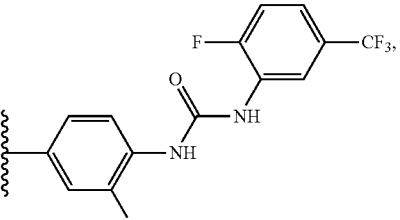
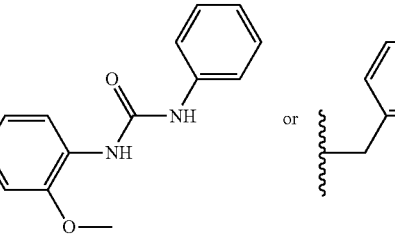

The present invention encompasses all compounds described by Formula 1, racemic or diastereoisomeric mixtures, pharmaceutically acceptable salts, prodrugs and active metabolites thereof.

Another aspect of the present invention provides a pharmaceutical composition comprising an effective amount of compound of Formula 1 and a pharmaceutically acceptable carrier, diluent or excipient.

In another aspect of the present invention, there is provided a use of the compound of Formula 1 as an inhibitor of protein kinase, more particularly, as an inhibitor of cFMS, Flt3, KDR, FGFR1 and Tie2.

Another aspect of the present invention provides a method of modulating kinase function, the method comprising contacting a cell with a compound of the present invention in an amount sufficient to modulate the enzymatic activity of a given kinase or kinases, such as cFMS, FLT3, KDR, FGFR1, Tie2 or others, thereby modulating the kinase function.

Another aspect of the present invention provides a method of modulating the target kinase function, the method comprising a) contacting a cell with a compound of the present invention in an amount sufficient to modulate the target kinase function, thereby b) modulating the target kinase activity and signaling.

Another aspect of the present invention provides a probe, the probe comprising a compound of Formula 1 labeled with a detectable label or an affinity tag. In other words, the probe comprises a residue of a compound of Formula 1 covalently conjugated to a detectable label. Such detectable labels include, but are not limited to, a fluorescent moiety, a chemiluminescent moiety, a paramagnetic contrast agent, a metal chelate, a radioactive isotope-containing moiety, or biotin. As used herein, the term "affinity tag" means a ligand or group, linked either to a compound of the present invention or to the target kinase, that allows the conjugate to be extracted from a solution.

DETAILED DESCRIPTION OF PREFERRED EMBODIMENTS

The present invention relates to a new class of 5-aryl-5H-pyrrolo[3,2-d]pyrimidin-4-amines which contain 6,7-fused alkyl and heteroalkyl ring systems. The inventors have found these compounds to be effective inhibitors of protein kinases, including members of the receptor tyrosine super family.

Compounds of the present invention may be formulated into a pharmaceutical composition which comprises an effective amount of a compound of Formula 1 with a pharmaceutically acceptable diluent or carrier. For example, the pharmaceutical compositions may be in a conventional pharmaceutical form suitable for oral administration (e.g., tablets, capsules, granules, powders and syrups), parenteral administration (e.g., injections (intravenous, intramuscular, or subcutaneous)), drop infusion preparations, inhalation, eye lotion, topical administration (e.g., ointment), or suppositories. Regardless of the route of administration selected the compounds may be formulated into pharmaceutically acceptable dosage forms by conventional methods known to those of skill in the art.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition, or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch, potato starch, and substituted or unsubstituted β-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically acceptable salt" refers to the relatively non-toxic, inorganic and organic acid addition salts of the compound(s). These salts can be prepared in situ during the final isolation and purification of the compound(s), or by separately reacting a purified compound(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. (See, for example, Berge et al. (1977) "Pharmaceutical Salts", *J. Pharm. Sci.* 66: 1-19.)

In other cases, the compounds of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of a compound(s). These salts can be likewise be prepared in situ during the final isolation and purification of the compound(s), or by separately reacting the purified compound(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

As used herein, the term "affinity tag" means a ligand or group, linked either to a compound of the present invention or to an protein kinase domain, that allows the conjugate to be extracted from a solution.

The term "alkyl" refers to substituted or unsubstituted saturated hydrocarbon groups, including straight-chain alkyl and branched-chain alkyl groups, including haloalkyl groups such as trifluoromethyl and 2,2,2-trifluoroethyl, etc. Representative alkyl groups include methyl, ethyl, n-propyl, isopropyl, n-butyl, t-butyl, isobutyl, sec-butyl, (cyclohexyl)m- ethyl, cyclopropylmethyl, n-pentyl, n-hexyl, n-heptyl, n-octyl, and the like. The terms "alkenyl" and "alkynyl" refer to substituted or unsubstituted unsaturated aliphatic groups analogous in length and possible substitution to the alkyls described above, but that contain at least one double or triple bond respectively. Representative alkenyl groups include vinyl, propen-2-yl, crotyl, isopenten-2-yl, 1,3-butadien-2-yl), 2,4-pentadienyl, and 1,4-pentadien-3-yl. Representative alkynyl groups include ethynyl, 1- and 3-propynyl, and 3-butynyl. In certain preferred embodiments, alkyl substituents are lower alkyl groups, e.g., having from 1 to 6 carbon atoms. Similarly, alkenyl and alkynyl preferably refer to lower alkenyl and alkynyl groups, e.g., having from 2 to 6 carbon atoms. As used herein, "alkylene" refers to an alkyl group with two open valencies (rather than a single valency), such as —$(CH_2)_{1-10}$— and substituted variants thereof.

The term "alkoxy" refers to an alkyl group having an oxygen attached thereto. Representative alkoxy groups include methoxy, ethoxy, propoxy, tert-butoxy and the like. An "ether" is two hydrocarbons covalently linked by an oxygen. Accordingly, the substituent of an alkyl that renders that alkyl an ether is or resembles an alkoxy.

The term "alkoxyalkyl" refers to an alkyl group substituted with an alkoxy group, thereby forming an ether.

The terms "amide" and "amido" are art-recognized as an amino-substituted carbonyl and includes a moiety that can be represented by the general formula:

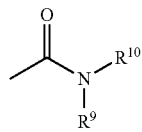

wherein $R^9$, $R^{10}$ are as defined above. Preferred embodiments of the amide will not include imides, which may be unstable.

The terms "amine" and "amino" are art-recognized and refer to both unsubstituted and substituted amines and salts thereof, e.g., a moiety that can be represented by the general formulae:

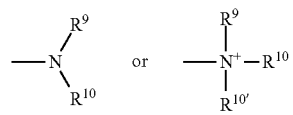

wherein $R^9$, $R^{10}$ and $R^{10'}$ each independently represent a hydrogen, an alkyl, an alkenyl, —$(CH_2)_m$—$R^8$, or $R^9$ and $R^{10}$ taken together with the N atom to which they are attached complete a heterocycle having from 4 to 8 atoms in the ring structure; $R^8$ represents an aryl, a cycloalkyl, a cycloalkenyl, a heterocyclyl or a polycyclyl; and m is zero or an integer from 1 to 8. In preferred embodiments, only one of $R^9$ or $R^{10}$ can be a carbonyl, e.g., $R^9$, $R^{10}$, and the nitrogen together do not form an imide. In even more preferred embodiments, $R^9$ and $R^{10}$ (and optionally $R^{10'}$) each independently represent a hydrogen, an alkyl, an alkenyl, or —$(CH_2)_m$—$R^8$. In certain embodiments, the amino group is basic, meaning the protonated form has a $pK_a \geq 7.00$.

The term "aralkyl", as used herein, refers to an alkyl group substituted with an aryl group.

The term "aryl" as used herein includes 5-, 6-, and 7-membered substituted or unsubstituted single-ring aromatic groups in which each atom of the ring is carbon. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, anthracene, and phenanthrene.

The terms "carbocycle" and "carbocyclyl", as used herein, refer to a non-aromatic substituted or unsubstituted ring in which each atom of the ring is carbon. The terms "carbocycle" and "carbocyclyl" also include polycyclic ring systems having two or more cyclic rings in which two or more carbons are common to two adjoining rings wherein at least one of the rings is carbocyclic, e.g., the other cyclic rings can be cycloalkyls, cycloalkenyls, cycloalkynyls, aryls, heteroaryls, and/or heterocyclyls. Representative carbocyclic groups include cyclopentyl, cyclohexyl, 1-cyclohexenyl, and 3-cyclohexen-1-yl, cycloheptyl.

The term "carbonyl" is art-recognized and includes such moieties as can be represented by the general formula:

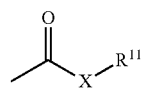

wherein X is a bond or represents an oxygen or a sulfur, and $R^{11}$ represents a hydrogen, an alkyl, an alkenyl, —$(CH_2)_m$—$R^8$ or a pharmaceutically acceptable salt. Where X is an oxygen and $R^{11}$ is not hydrogen, the formula represents an "ester". Where X is an oxygen, and $R^{11}$ is a hydrogen, the formula represents a "carboxylic acid".

The terms "heteroaryl" includes substituted or unsubstituted aromatic 5- to 7-membered ring structures, more preferably 5- to 6-membered rings, whose ring structures include one to four heteroatoms. The term "heteroaryl" also includes polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, isoxazole, oxazole, thiazole, triazole, pyrazole, pyridine, pyrazine, pyridazine and pyrimidine, and the like.

The term "heteroatom" as used herein means an atom of any element other than carbon or hydrogen. Preferred heteroatoms are nitrogen, oxygen, and sulfur.

The terms "heterocyclyl" or "heterocyclic group" refer to substituted or unsubstituted non-aromatic 3- to 10-membered ring structures, more preferably 3- to 7-membered rings, whose ring structures include one to four heteroatoms. The term terms "heterocyclyl" or "heterocyclic group" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, tetrahydrofuran, tetrahydropyran, piperidine, piperazine, pyrrolidine, morpholine, lactones, and lactams.

The term "hydrocarbon", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The terms "polycyclyl" or "polycyclic" refer to two or more rings (e.g., cycloalkyls, cycloalkenyls, cycloalkynyls, aryls, heteroaryls, and/or heterocyclyls) in which two or more carbons are common to two adjoining rings, e.g., the rings are "fused rings". Each of the rings of the polycycle can be substituted or unsubstituted.

As used herein, the term "probe" means a compound of the invention which is labeled with either a detectable label or an affinity tag, and which is capable of binding, either covalently or non-covalently, to a protein kinase domain. When, for example, the probe is non-covalently bound, it may be displaced by a test compound. When, for example, the probe is bound covalently, it may be used to form cross-linked adducts, which may be quantified and inhibited by a test compound.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

Compounds of the invention also include all isotopes of atoms present in the intermediates and/or final compounds. Isotopes include those atoms having the same atomic number but different mass numbers. For example, isotopes of hydrogen include deuterium and tritium.

Table 1 summarizes some illustrative embodiments of the compound of Formula 1.

TABLE 1

| Compound | Structure | MS (m/z) |
|---|---|---|
| 1 | 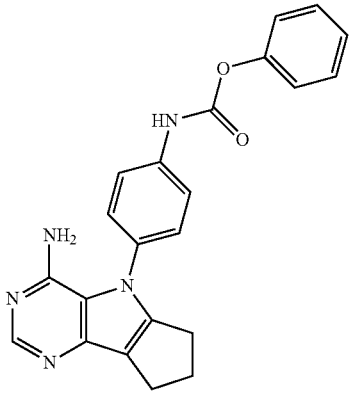 [SMILES: Nc1ncnc2c3c(n(-c4ccc(NC(=O)Oc5ccccc5)cc4)c12)CCC3] | $[M + H]^+ = 400.2$ |
| 2 | 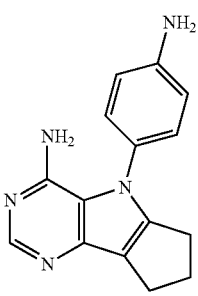 | $[M + H]^+ = 266.2$ |

TABLE 1-continued

| Compound | Structure | MS (m/z) |
|---|---|---|
| 3 | 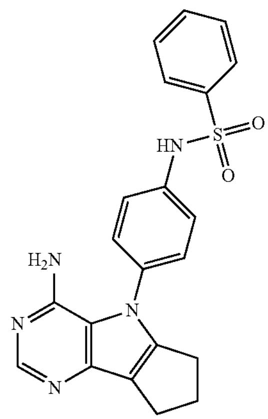 [SMILES: Nc1ncnc2c3c(n(-c4ccc(NS(=O)(=O)c5ccccc5)cc4)c12)CCC3] | [M + H]+ = 406.1 |
| 4 | 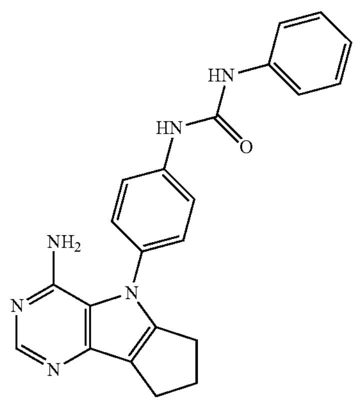 [SMILES: Nc1ncnc2c3c(n(-c4ccc(NC(=O)Nc5ccccc5)cc4)c12)CCC3] | [M + H]+ = 358.2 |
| 5 | 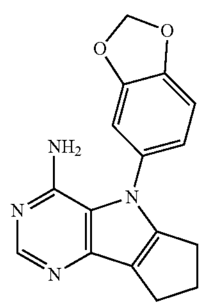 [SMILES: Nc1ncnc2c3c(n(-c4ccc5c(c4)OCO5)c12)CCC3] | [M + H]+ = 295.1 |
| 6 | 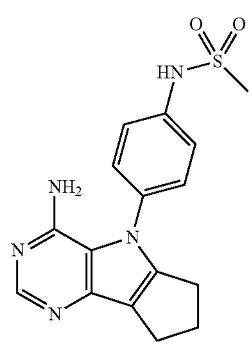 [SMILES: CS(=O)(=O)Nc1ccc(-n2c3c(c4ncnc(N)c42)CCC3)cc1] | [M + H]+ = 344.1 |

TABLE 1-continued
| Compound | Structure | MS (m/z) |
| --- | --- | --- |
| 7 | 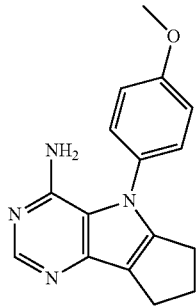 [SMILES: COc1ccc(-n2c3c(c4ncnc(N)c42)CCC3)cc1] | [M + H]⁺ = 281.1 |
| 8 | 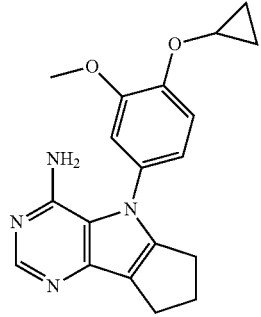 [SMILES: COc1cc(-n2c3c(c4ncnc(N)c42)CCC3)ccc1OC1CC1] | [M + H]⁺ = 339.2 |
| 9 | 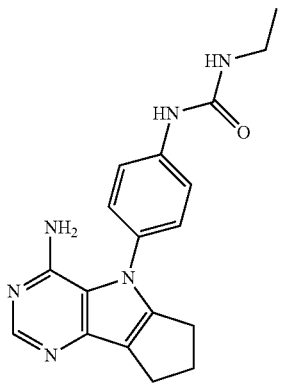 [SMILES: CCNC(=O)Nc1ccc(-n2c3c(c4ncnc(N)c42)CCC3)cc1] | [M + H]⁺ = 337.2 |
| 10 | 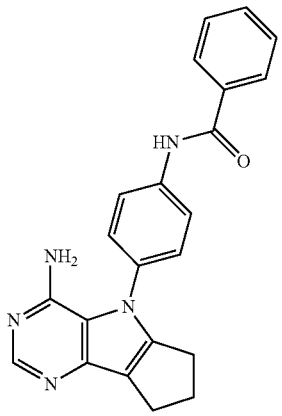 [SMILES: Nc1ncnc2c3c(n(-c4ccc(NC(=O)c5ccccc5)cc4)c12)CCC3] | [M + H]⁺ = 370.2 |

TABLE 1-continued

| Compound | Structure | MS (m/z) |
|---|---|---|
| 11 | 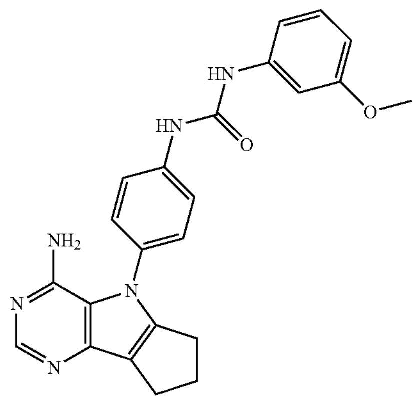 [SMILES: COc1cccc(NC(=O)Nc2ccc(-n3c4c(c5ncnc(N)c53)CCC4)cc2)c1] | [M + H]⁺ = 415.2 |
| 12 | 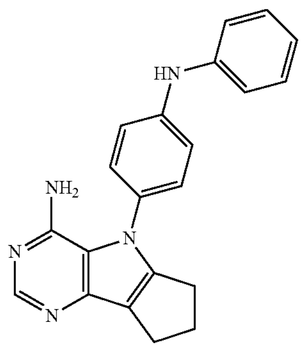 [SMILES: Nc1ncnc2c3c(n(-c4ccc(Nc5ccccc5)cc4)c12)CCC3] | [M + H]⁺ = 342.2 |
| 13 | 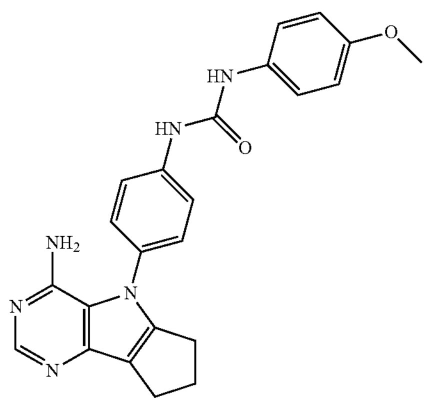 [SMILES: COc1ccc(NC(=O)Nc2ccc(-n3c4c(c5ncnc(N)c53)CCC4)cc2)cc1] | [M + H]⁺ = 415.2 |
| 14 | 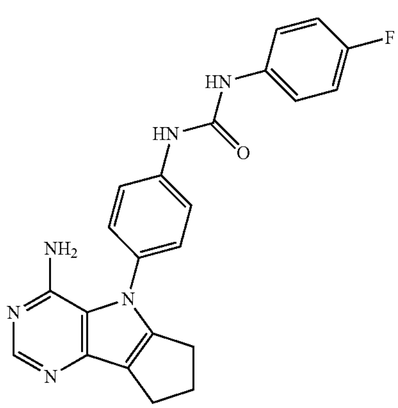 [SMILES: Nc1ncnc2c3c(n(-c4ccc(NC(=O)Nc5ccc(F)cc5)cc4)c12)CCC3] | [M + H]⁺ = 403.2 |

TABLE 1-continued

| Compound | Structure | MS (m/z) |
| --- | --- | --- |
| 15 | 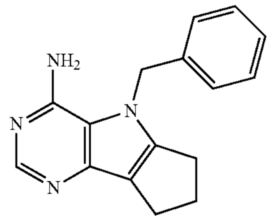 [SMILES: Nc1ncnc2c3c(n(Cc4ccccc4)c12)CCC3] | [M + H]⁺ = 265.1 |
| 16 | 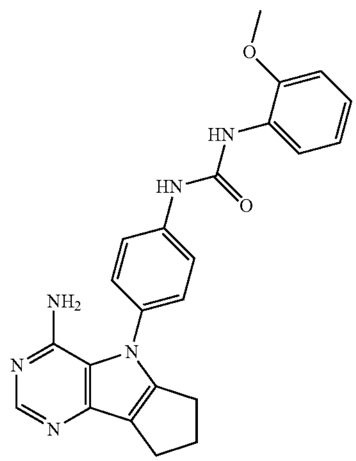 [SMILES: COc1ccccc1NC(=O)Nc1ccc(-n2c3c(c4ncnc(N)c42)CCC3)cc1] | [M + H]⁺ = 415.1 |
| 17 | 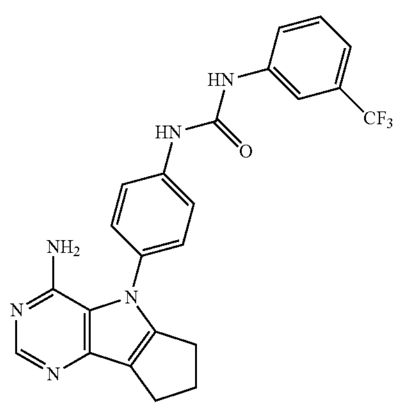 [SMILES: Nc1ncnc2c3c(n(-c4ccc(NC(=O)Nc5cccc(C(F)(F)F)c5)cc4)c12)CCC3] | [M + H]⁺ = 453.1 |
| 18 | 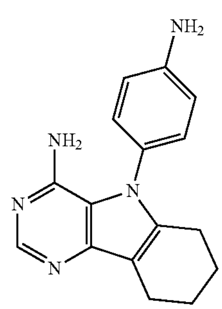 [SMILES: Nc1ccc(-n2c3c(c4ncnc(N)c42)CCCC3)cc1] | [M + H]⁺ = 280.2 |

TABLE 1-continued
| Compound | Structure | MS (m/z) |
|---|---|---|
| 19 | 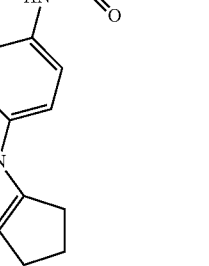 | [M + H]⁺ = 403.1 |
| 20 | 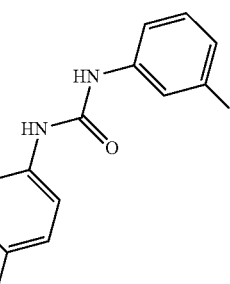 | [M + H]⁺ = 419.3 |
| 21 | 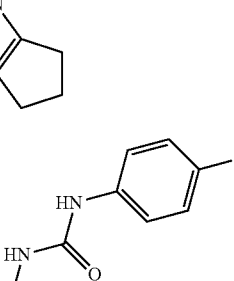 | [M + H]⁺ = 453.1 |
| 22 | 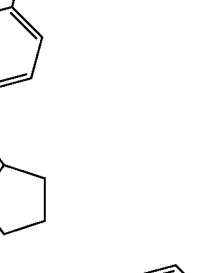 | [M + H]⁺ = 419.5 |

TABLE 1-continued

| Compound | Structure | MS (m/z) |
|---|---|---|
| 23 | 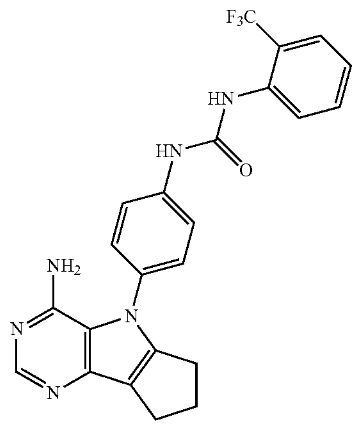 [SMILES: Nc1ncnc2c3c(n(-c4ccc(NC(=O)Nc5ccccc5C(F)(F)F)cc4)c12)CCC3] | [M + H]⁺ = 453.1 |
| 24 | 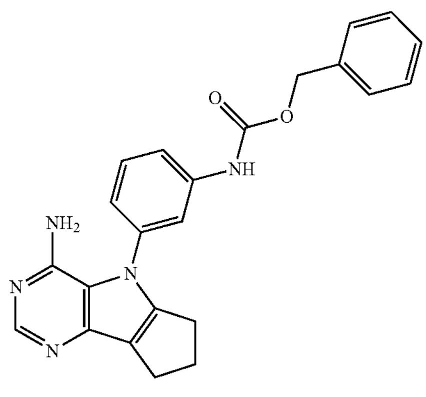 [SMILES: Nc1ncnc2c3c(n(-c4cccc(NC(=O)OCc5ccccc5)c4)c12)CCC3] | [M + H]⁺ = 400.2 |
| 25 | 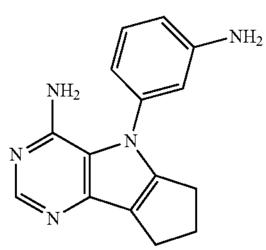 [SMILES: Nc1cccc(-n2c3c(c4ncnc(N)c42)CCC3)c1] | [M + H]⁺ = 266.1 |
| 26 | 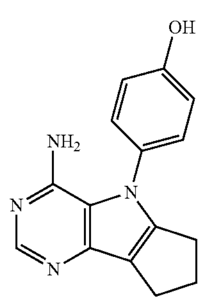 [SMILES: Nc1ncnc2c3c(n(-c4ccc(O)cc4)c12)CCC3] | [M + H]⁺ = 267.1 |

TABLE 1-continued

| Compound | Structure | MS (m/z) |
|---|---|---|
| 27 | 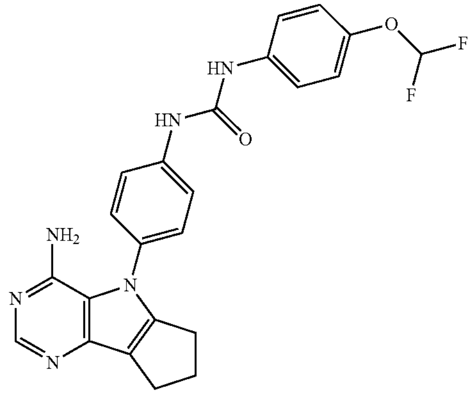 [SMILES: Nc1ncnc2c3c(n(-c4ccc(NC(=O)Nc5ccc(OC(F)F)cc5)cc4)c12)CCC3] | [M + H]⁺ = 451.1 |
| 28 | 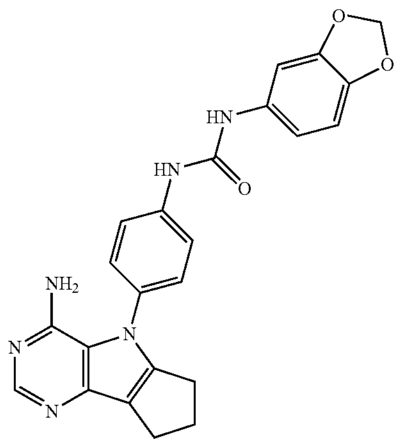 [SMILES: Nc1ncnc2c3c(n(-c4ccc(NC(=O)Nc5ccc6c(c5)OCO6)cc4)c12)CCC3] | [M + H]⁺ = 429.1 |
| 29 | 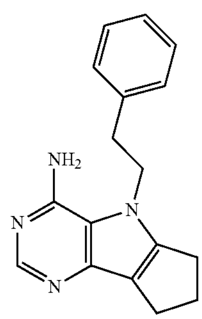 [SMILES: Nc1ncnc2c3c(n(CCc4ccccc4)c12)CCC3] | [M + H]⁺ = 279.2 |
| 30 | 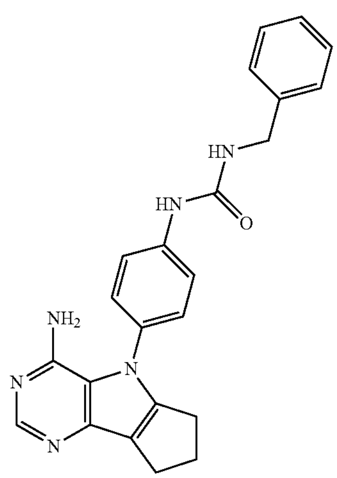 [SMILES: Nc1ncnc2c3c(n(-c4ccc(NC(=O)NCc5ccccc5)cc4)c12)CCC3] | [M + H]⁺ = 399.2 |

TABLE 1-continued

| Compound | Structure | MS (m/z) |
| --- | --- | --- |
| 31 | 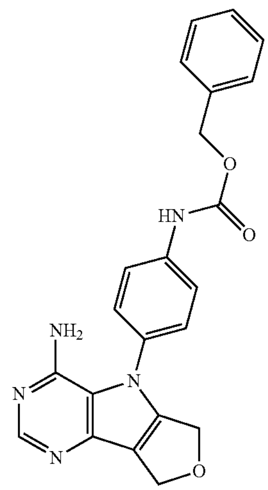 [SMILES: Nc1ncnc2c3c(n(-c4ccc(NC(=O)OCc5ccccc5)cc4)c12)COC3] | [M + H]+ = 402.2 |
| 32 | 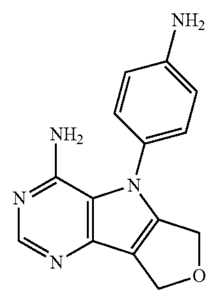 | [M + H]+ = 268.2 |
| 33 | 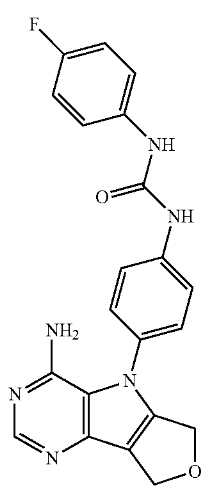 [SMILES: Nc1ncnc2c3c(n(-c4ccc(NC(=O)Nc5ccc(F)cc5)cc4)c12)COC3] | [M + H]+ = 405.2 |
| 34 | 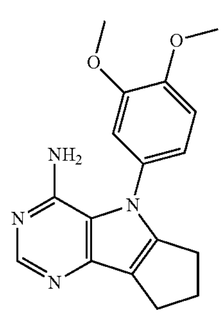 [SMILES: COc1ccc(-n2c3c(c4ncnc(N)c42)CCC3)cc1OC] | [M + H]+ = 311.2 |

TABLE 1-continued

| Compound | Structure | MS (m/z) |
| --- | --- | --- |
| 35 | 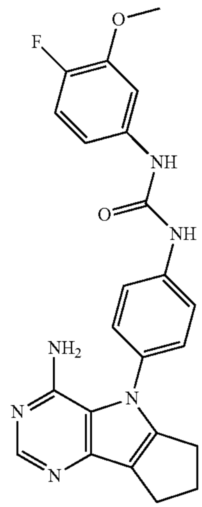 [SMILES: COc1cc(NC(=O)Nc2ccc(-n3c4c(c5ncnc(N)c53)CCC4)cc2)ccc1F] | $[M + H]^+ = 433.2$ |
| 36 | 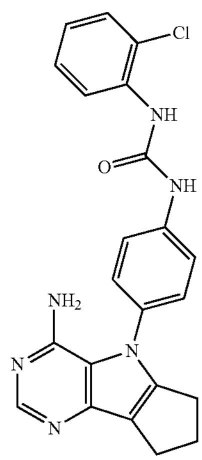 [SMILES: Nc1ncnc2c3c(n(-c4ccc(NC(=O)Nc5ccccc5Cl)cc4)c12)CCC3] | $[M + H]^+ = 419.4$ |
| 37 | 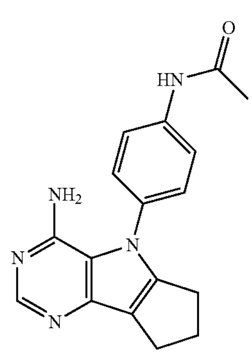 [SMILES: CC(=O)Nc1ccc(-n2c3c(c4ncnc(N)c42)CCC3)cc1] | $[M + H]^+ = 308.3$ |

TABLE 1-continued
| Compound | Structure | MS (m/z) |
|---|---|---|
| 38 | 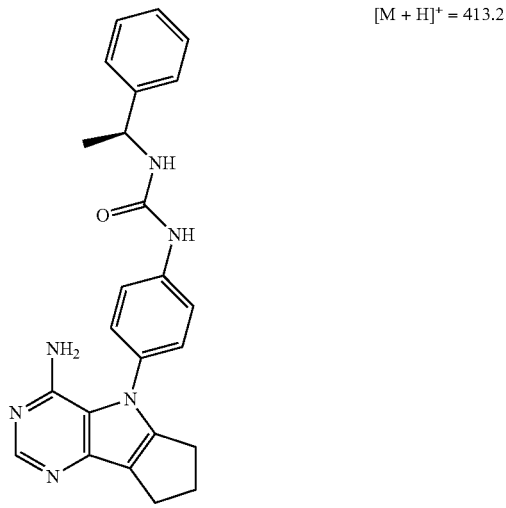 | [M + H]+ = 413.2 |
| 39 | 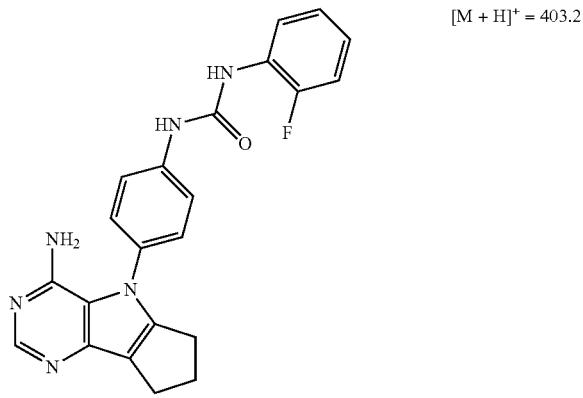 | [M + H]+ = 403.2 |
| 40 | 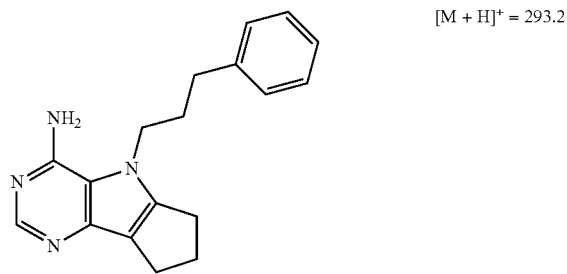 | [M + H]+ = 293.2 |

TABLE 1-continued

| Compound | Structure | MS (m/z) |
|---|---|---|
| 41 | 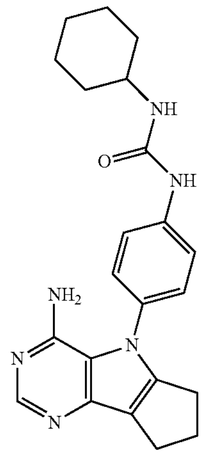 [SMILES: Nc1ncnc2c3c(n(-c4ccc(NC(=O)NC5CCCCC5)cc4)c12)CCC3] | [M + H]⁺ = 391.3 |
| 42 | 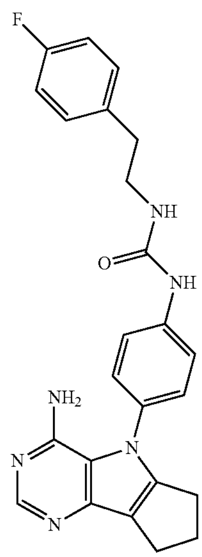 [SMILES: Nc1ncnc2c3c(n(-c4ccc(NC(=O)NCCc5ccc(F)cc5)cc4)c12)CCC3] | [M + H]⁺ = 431.2 |
| 43 | 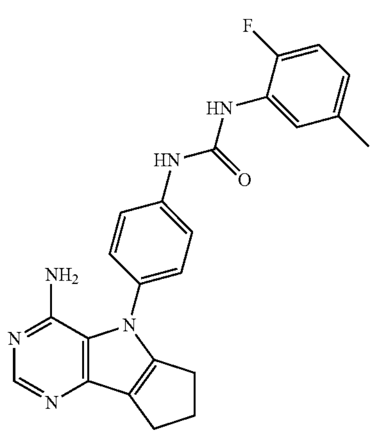 [SMILES: Cc1ccc(F)c(NC(=O)Nc2ccc(-n3c4c(c5ncnc(N)c53)CCC4)cc2)c1] | [M + H]⁺ = 417.2 |

TABLE 1-continued

| Compound | Structure | MS (m/z) |
|---|---|---|
| 44 | 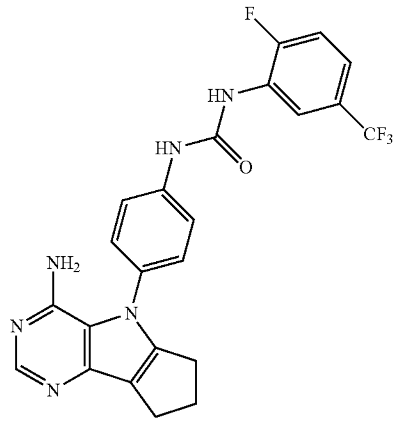 | [M + H]⁺ = 471.1 |
| 45 | 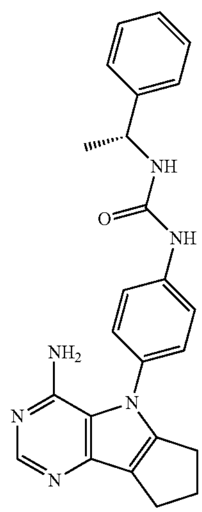 [SMILES: C[C@@H](NC(=O)Nc1ccc(-n2c3c(c4ncnc(N)c42)CCC3)cc1)c1ccccc1] | [M + H]⁺ = 413.2 |
| 46 | 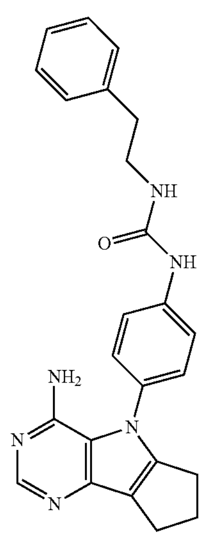 [SMILES: Nc1ncnc2c3c(n(-c4ccc(NC(=O)NCCc5ccccc5)cc4)c12)CCC3] | [M + H]⁺ = 413.2 |

TABLE 1-continued

| Compound | Structure | MS (m/z) |
| --- | --- | --- |
| 47 | 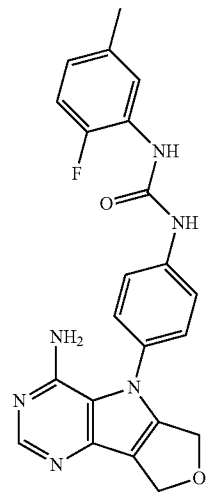 [SMILES: Cc1ccc(F)c(NC(=O)Nc2ccc(-n3c4c(c5ncnc(N)c53)COC4)cc2)c1] | $[M + H]^+ = 419.2$ |
| 48 | 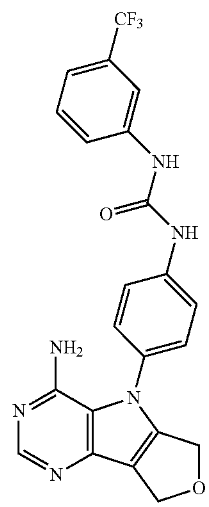 [SMILES: Nc1ncnc2c3c(n(-c4ccc(NC(=O)Nc5cccc(C(F)(F)F)c5)cc4)c12)COC3] | $[M + H]^+ = 455.1$ |
| 49 | 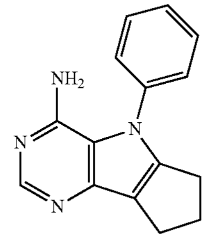 [SMILES: Nc1ncnc2c3c(n(-c4ccccc4)c12)CCC3] | $[M + H]^+ = 251.1$ |

TABLE 1-continued

| Compound | Structure | MS (m/z) |
| --- | --- | --- |
| 50 | 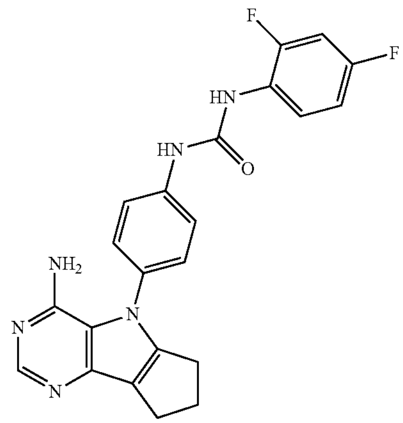 [SMILES: Nc1ncnc2c3c(n(-c4ccc(NC(=O)Nc5ccc(F)cc5F)cc4)c12)CCC3] | [M + H]⁺ = 421.2 |
| 51 | 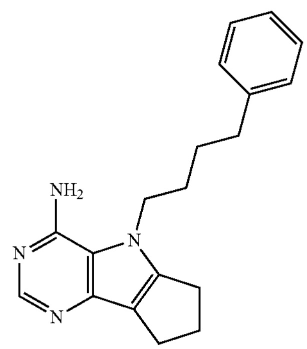 [SMILES: Nc1ncnc2c3c(n(CCCCc4ccccc4)c12)CCC3] | [M + H]⁺ = 307.2 |
| 52 | 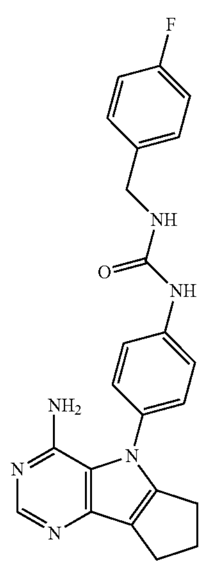 [SMILES: Nc1ncnc2c3c(n(-c4ccc(NC(=O)NCc5ccc(F)cc5)cc4)c12)CCC3] | [M + H]⁺ = 417.2 |

TABLE 1-continued

| Compound | Structure | MS (m/z) |
|---|---|---|
| 53 | 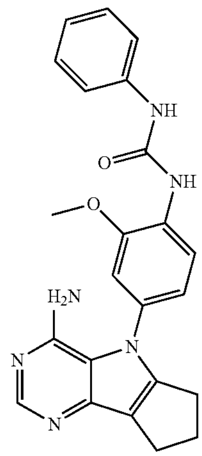 | [M + H]⁺ = 373.2 |
| 54 | 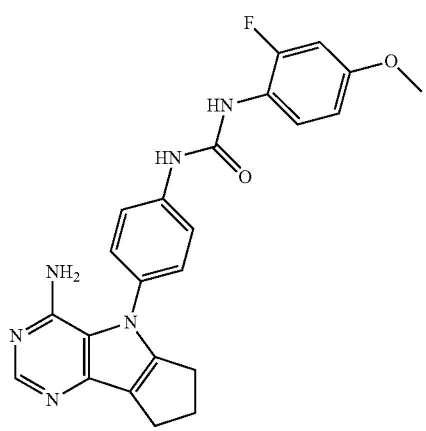 [SMILES: COc1ccc(NC(=O)Nc2ccc(-n3c4c(c5ncnc(N)c53)CCC4)cc2)c(F)c1] | [M + H]⁺ = 433.2 |
| 55 | 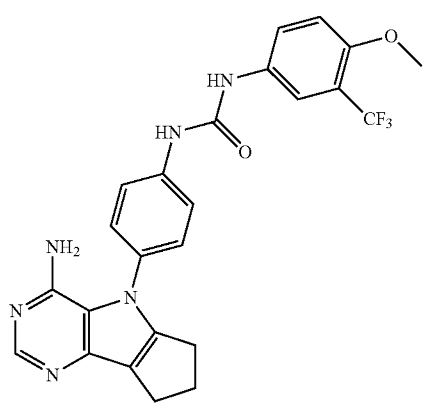 [SMILES: COc1ccc(NC(=O)Nc2ccc(-n3c4c(c5ncnc(N)c53)CCC4)cc2)cc1C(F)(F)F] | [M + H]⁺ = 483.1 |

TABLE 1-continued

| Compound | Structure | MS (m/z) |
|---|---|---|
| 56 | 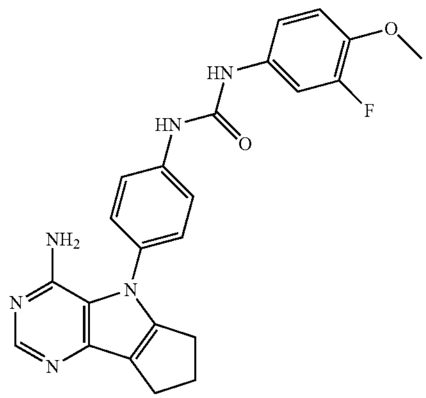 [SMILES: COc1ccc(NC(=O)Nc2ccc(-n3c4c(c5ncnc(N)c53)CCC4)cc2)cc1F] | [M + H]⁺ = 433.3 |
| 57 | 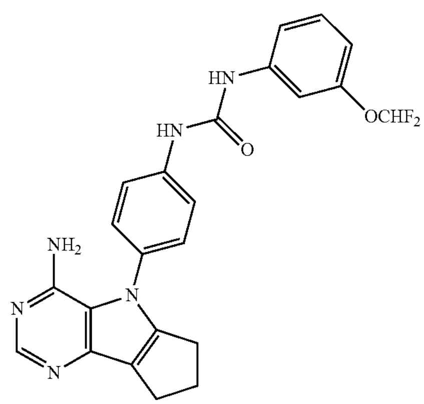 [SMILES: Nc1ncnc2c3c(n(-c4ccc(NC(=O)Nc5cccc(OC(F)F)c5)cc4)c12)CCC3] | [M + H]⁺ = 451.1 |
| 58 | 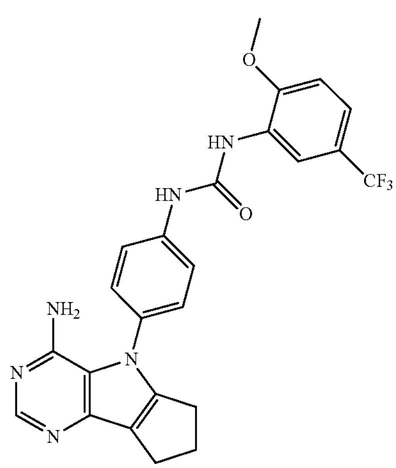 [SMILES: COc1ccc(C(F)(F)F)cc1NC(=O)Nc1ccc(-n2c3c(c4ncnc(N)c42)CCC3)cc1] | [M + H]⁺ = 483.1 |

TABLE 1-continued

| Compound | Structure | MS (m/z) |
|---|---|---|
| 59 | 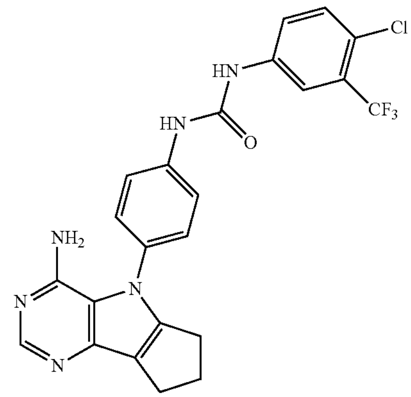 [SMILES: Nc1ncnc2c3c(n(-c4ccc(NC(=O)Nc5ccc(Cl)c(C(F)(F)F)c5)cc4)c12)CCC3] | [M + H]⁺ = 487.3 |
| 60 | 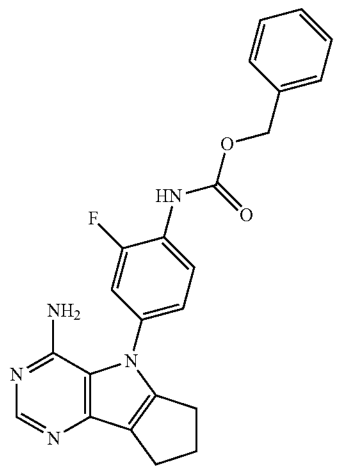 [SMILES: Nc1ncnc2c3c(n(-c4ccc(NC(=O)OCc5ccccc5)c(F)c4)c12)CCC3] | [M + H]⁺ = 418.1 |
| 61 | 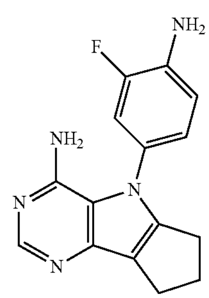 [SMILES: Nc1ccc(-n2c3c(c4ncnc(N)c42)CCC3)cc1F] | |
| 62 | 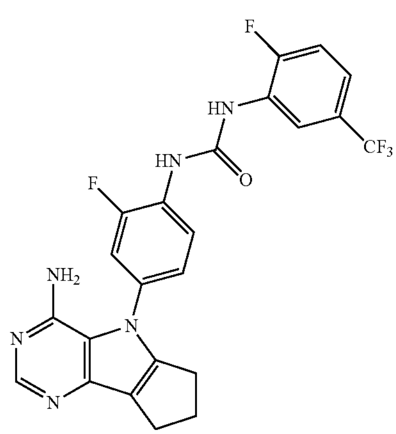 [SMILES: Nc1ncnc2c3c(n(-c4ccc(NC(=O)Nc5cc(C(F)(F)F)ccc5F)c(F)c4)c12)CCC3] | [M + H]⁺ = 489.1 |

TABLE 1-continued

| Compound | Structure | MS (m/z) |
|---|---|---|
| 63 | 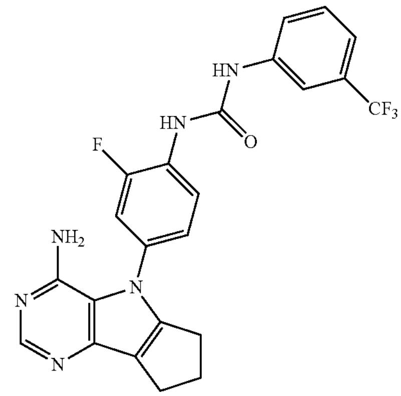 [SMILES: Nc1ncnc2c3c(n(-c4ccc(NC(=O)Nc5cccc(C(F)(F)F)c5)c(F)c4)c12)CCC3] | [M + H]+ = 471.1 |
| 64 | 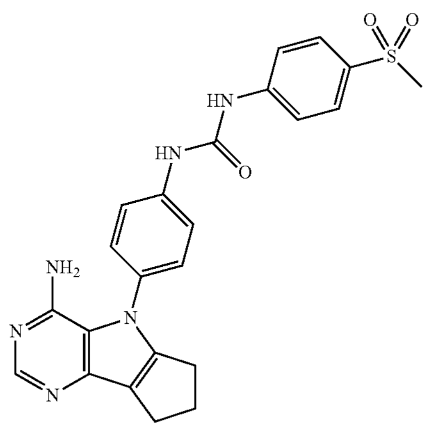 [SMILES: CS(=O)(=O)c1ccc(NC(=O)Nc2ccc(-n3c4c(c5ncnc(N)c53)CCC4)cc2)cc1] | [M + H]+ = 463.2 |
| 65 | 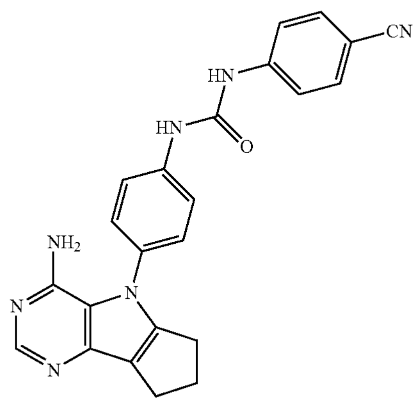 [SMILES: N#Cc1ccc(NC(=O)Nc2ccc(-n3c4c(c5ncnc(N)c53)CCC4)cc2)cc1] | [M + H]+ = 410.2 |
| 66 | 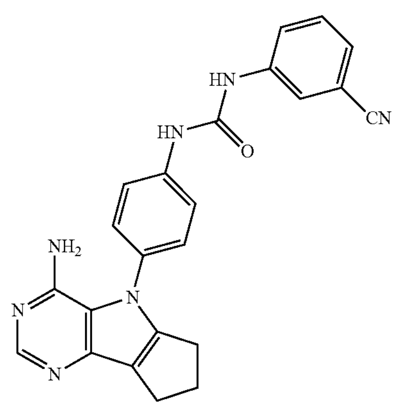 [SMILES: N#Cc1cccc(NC(=O)Nc2ccc(-n3c4c(c5ncnc(N)c53)CCC4)cc2)c1] | [M + H]+ = 410.2 |

TABLE 1-continued
| Compound | Structure | MS (m/z) |
| --- | --- | --- |
| 67 | 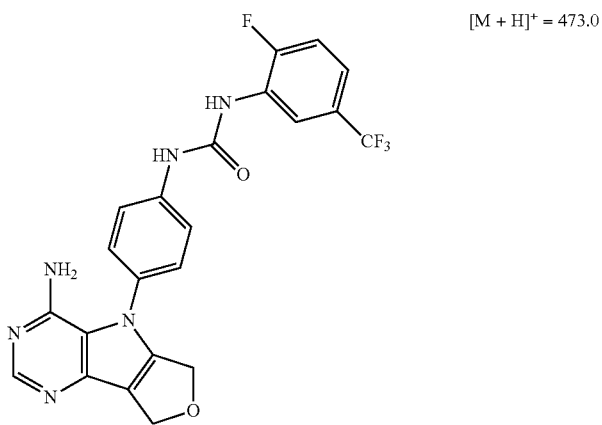 | [M + H]⁺ = 473.0 |
| 68 | 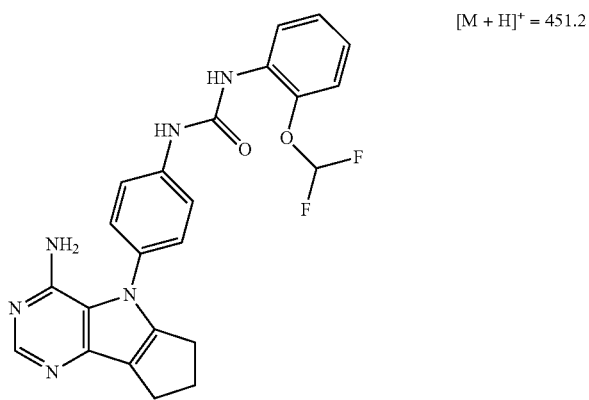 | [M + H]⁺ = 451.2 |
| 69 | 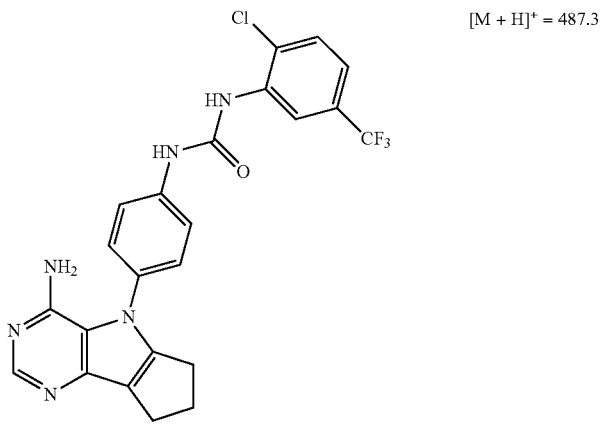 | [M + H]⁺ = 487.3 |

TABLE 1-continued
| Compound | Structure | MS (m/z) |
|---|---|---|
| 70 | 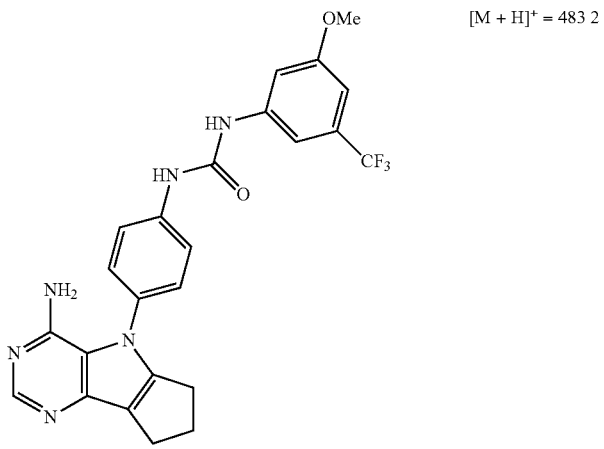 | [M + H]⁺ = 483.2 |
| 71 | 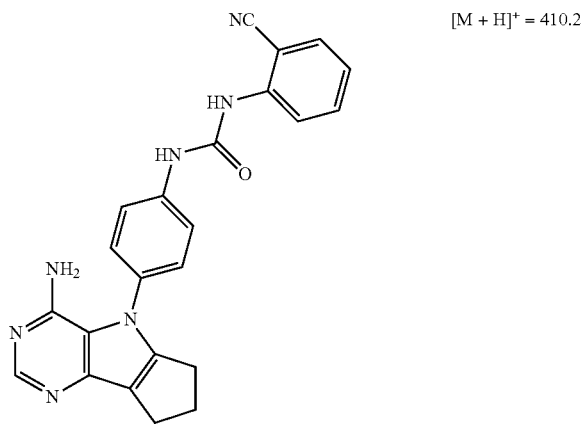 | [M + H]⁺ = 410.2 |
| 72 | 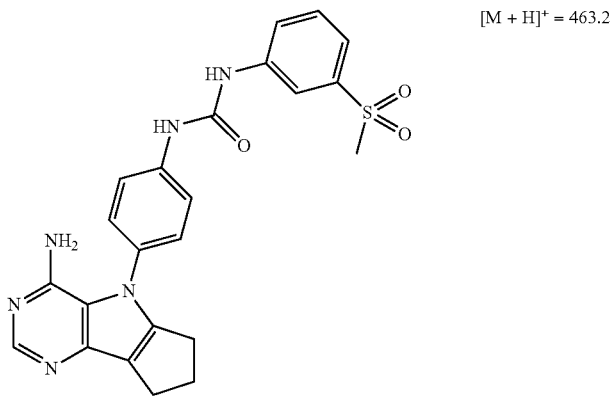 | [M + H]⁺ = 463.2 |

TABLE 1-continued

| Compound | Structure | MS (m/z) |
|---|---|---|
| 73 | 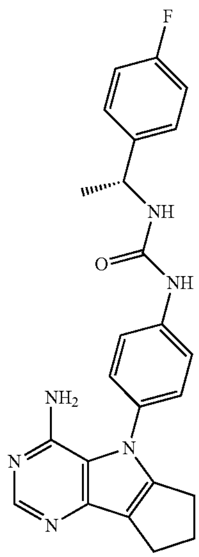 [SMILES: C[C@@H](NC(=O)Nc1ccc(-n2c3c(c4ncnc(N)c42)CCC3)cc1)c1ccc(F)cc1] | [M + H]⁺ = 431.2 |
| 74 | 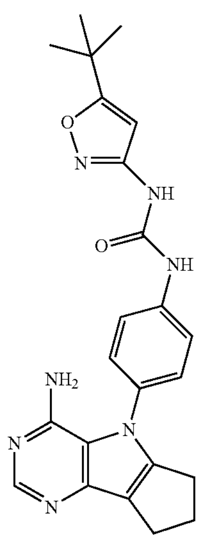 [SMILES: CC(C)(C)c1cc(NC(=O)Nc2ccc(-n3c4c(c5ncnc(N)c53)CCC4)cc2)no1] | [M + H]⁺ = 432.2 |

General Synthetic Methods

General Synthetic Method A:

Compounds of general formula i-e were prepared in a four step process which is summarized in Scheme i. Alkylation of $R^1NH_2$ with bromoacetonitrile provided intermediate i-a. Condensation of i-a with i-b in the presence of an acid such as p-toluenesulphonic acid, provided intermediate i-c. Treatment of intermediate i-c with a base such as tBuOK in t-BuOH provided intermediate i-d. Treatment of intermediate i-d with formamidine acetate in ethanol provided compounds of general formula i-e.

Scheme i

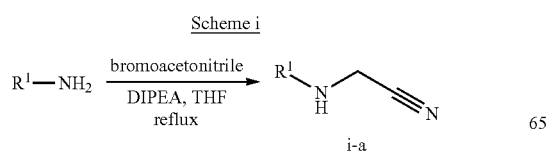

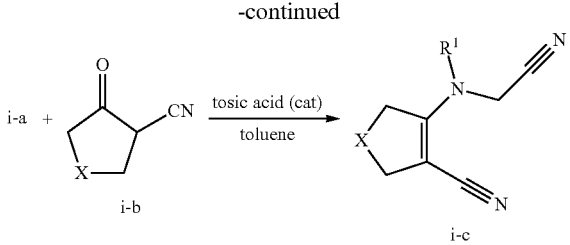

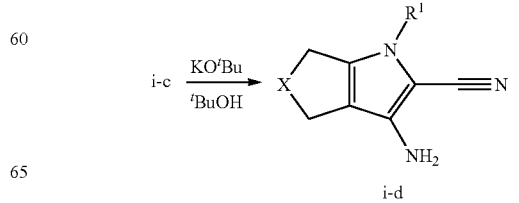

-continued

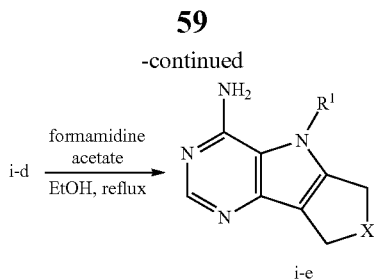

i-e

Synthesis of Compound 1

Scheme 1

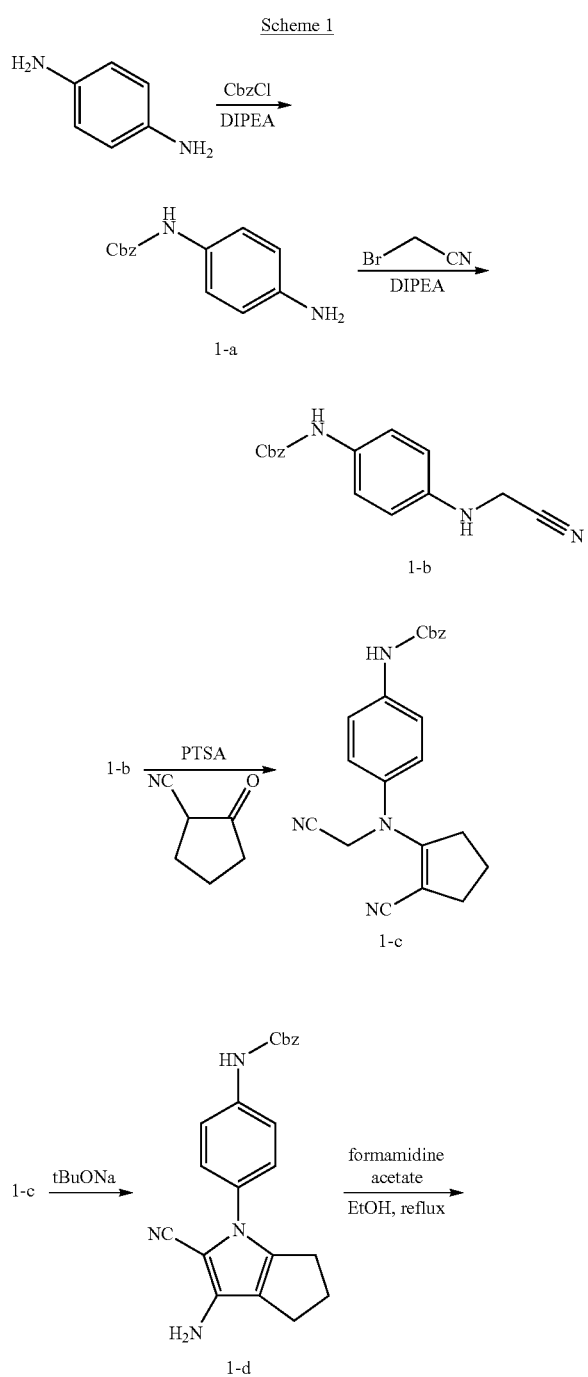

-continued

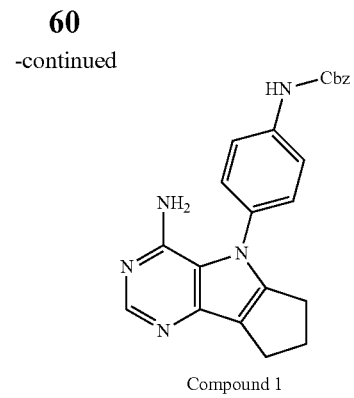

Compound 1

Step 1: Intermediate 1-a

To a solution of benzene-1,4-diamine (10.0 g, 92 mmol) in dichloromethane (1000 mL), cooled to 0° C., were added benzyl chloroformate (13.20 ml, 92.0 mmol) and DIPEA (16.15 ml, 92.0 mmol). The reaction mixture was slowly warmed to room temperature and stirred overnight. The reaction was concentrated to half volume. Water and ethyl acetate was added, the organic layer was separated, washed with brine, dried over $MgSO_4$, filtered and concentrated under reduced pressure. Diethyl ether (30 mL) was added to the residue; a precipitated formed and was removed by filtration. The filtrate was concentrated in vacuo to provide intermediate 1-a as beige solid.

Step 2: Intermediate 1-b

To a solution of intermediate 1-a (14.3 g, 59.0 mmol) and 2-bromoacetonitrile (7.79 g, 64.9 mmol) in THF (150 ml) was added DIPEA at room temperature. The reaction mixture was stirred at 80° C. overnight and then cooled to room temperature. Saturated aqueous ammonium chloride and ethyl acetate were added; the organic layer was separated, washed with saturated aqueous ammonium chloride and brine, dried over $MgSO_4$, filtered and concentrated under reduced pressure. Diethyl ether was added to the residue, a precipitate formed, and intermediate 1-b was collected by filtration as beige solid.

Step 3: Intermediate 1-c

To a solution of intermediate 1-b (2.00 g, 7.11 mmol) in toluene (50 mL) were added 2-oxocyclopentanecarbonitrile (815 mg, 7.47 mmol) and 4-methylbenzenesulfonic acid hydrate (0.135 g, 0.711 mmol). The reaction was refluxed for 3 hours using a dean-stark and then cooled to room temperature. Saturated aqueous $NaHCO_3$ and ethyl acetate were added, the organic layer was separated, washed with brine, dried over $MgSO_4$, filtered and concentrated under reduced pressure. Hexane was added to the residue, a precipitate formed, intermediate 1-c was collected by filtration as beige solid.

Step 4: Intermediate 1-d

To a solution of intermediate 1-c (2.10 g, 5.64 mmol) in tert-butanol (25 mL) was added sodium tert-butoxide (542 mg, 5.64 mmol) and the reaction was stirred at 80° C. for 2 hours and then cooled to room temperature. Saturated aqueous ammonium chloride and ethyl acetate were added, the organic layer was separated, the aqueous phase was extracted with ethyl acetate, the combined organic extracts were washed with brine, dried over $MgSO_4$, filtered and concentrated under reduced pressure. Diethyl ether was added to the residue, a precipitate formed, intermediate 1-d was collected by filtration as beige solid.

Step 5: Compound 1

To a solution of intermediate 1-d (2.39 g, 6.42 mmol) in ethanol (50 ml) was added formamidine acetate (5.34 g, 51.3 mmol) and the reaction was stirred at 80° C. for 1.5 hour. The reaction was concentrated under reduced pressure. A saturated aqueous solution of NaHCO₃ and ethyl acetate were added, the organic layer was separated, washed with brine, dried over anhydrous MgSO₄, filtered and concentrated under reduced pressure to provide compound 1 as beige solid. MS (m/z) M+H=400.2

Synthesis of Compound 2

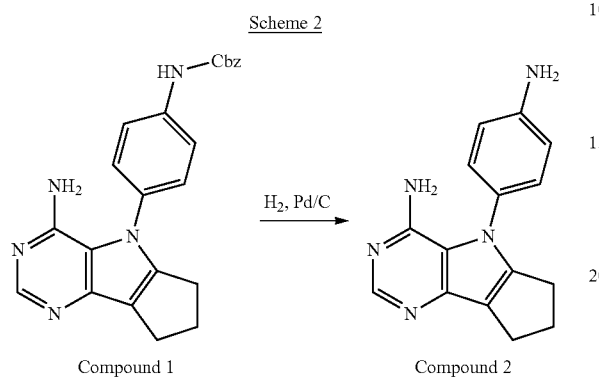

A methanol solution of compound 1 (114 mg, 0.24 mmol) was treated with 10% Pd/C (53 mg, 0.02 mmol) and purged with H₂. The solution was stirred under H2 (1 atom.) for 18 hours before being filtered through celite. The filtrate was concentrated in vacuo and purified by silica gel chromatography provided compound 2 as beige solid. MS (m/z) M+H=266.2

Synthesis of Compound 3

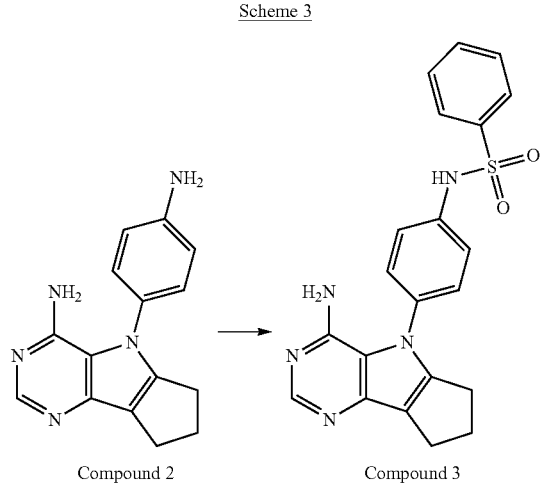 [SMILES: Nc1ccc(-n2c3c(c4ncnc(N)c42)CCC3)cc1 ; Nc1ncnc2c3c(n(-c4ccc(NS(=O)(=O)c5ccccc5)cc4)c12)CCC3]

To a solution of compound 2 (50 mg, 0.16 mmol) in pyridine (1 mL), cooled to 0° C., were added DMAP (2.0 mg, 0.017 mmol) and phenylsulfonyl chloride (64.3 mg, 0.364 mmol) in dichloromethane. The reaction was stirred at 80° C. for 3 hours and then cooled to room temperature. A saturated aqueous solution of ammonium chloride and ethyl acetate were added, the organic layer was separated, washed with a saturated aqueous solution of NaHCO₃ and brine, dried over MgSO₄, filtered and concentrated in vacuo. Purification by silica gel chromatography provided compound 3 as beige solid. MS (m/z) M+H=406.1

Synthesis of Compound 4

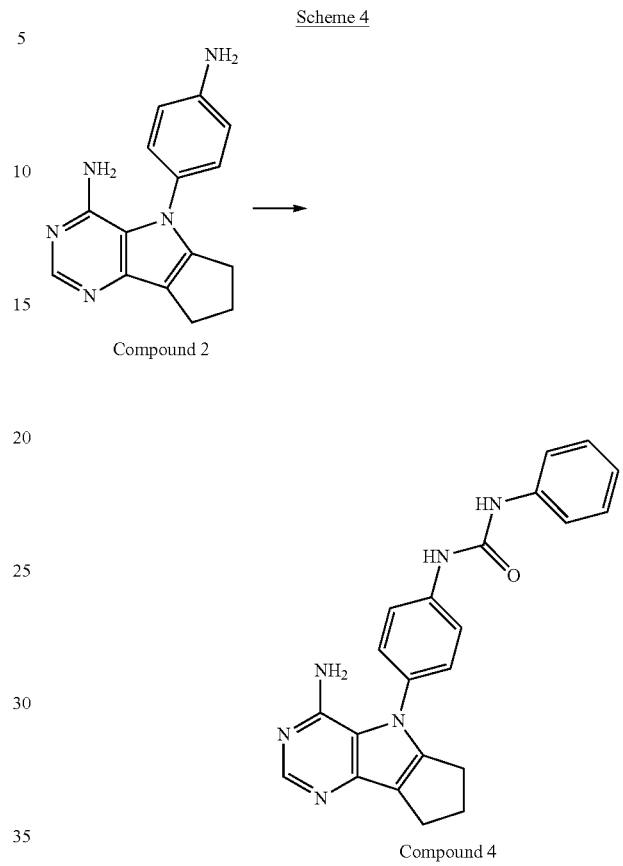

To a solution of compound 2 (83 mg, 0.275 mmol) in pyridine (1 mL), cooled to 0° C., was added a solution of phenylisocyanate (36 mg, 0.30) in dichloromethane. The reaction was then stirred at room temperature for 18 hours. A saturated aqueous solution of ammonium chloride and ethyl acetate were added, the organic layer was separated, washed with a saturated aqueous solution of NaHCO₃ and brine, dried over MgSO₄, filtered and concentrated in vacuo. Purification by reverse phase chromatography eluting with 10-70% methanol in 1% HCl gradient provided compound 4.HCl as white solid. MS (m/z) M+H=358.2

Synthesis of Compound 17

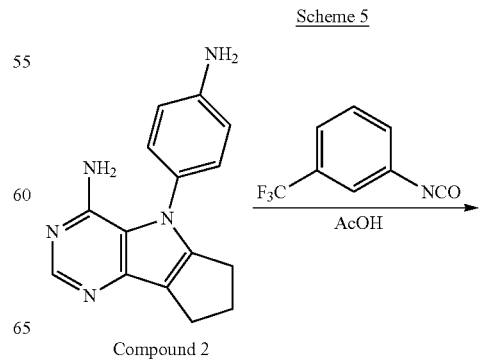

-continued

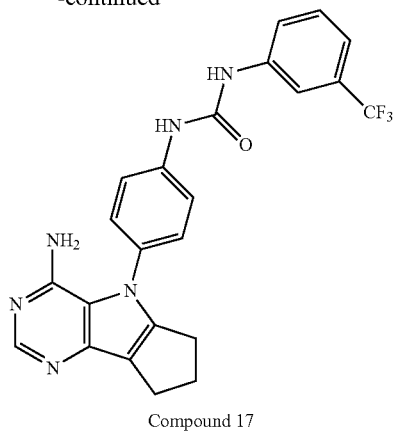
Compound 17

To a solution of compound 2 (150 mg, 0.56 mmol) in acetic acid (5 mL) was added (trifluoromethyl)phenyl isocyanate (83 uL, 0.59 mmol) and the reaction was then stirred at room temperature for 30 minutes. Ethyl acetate was added; a precipitate formed and was collected by filtration, dried under vacuo to provide compound 17 as a white solid. MS (m/z) M+H=453.1

Synthesis of Compound 27

Scheme 6

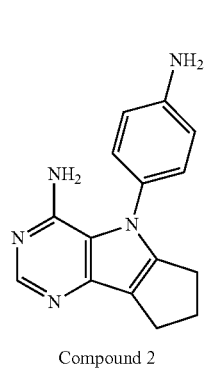
Compound 2

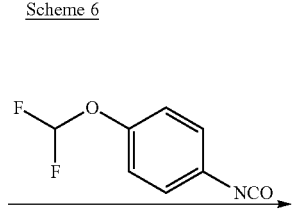

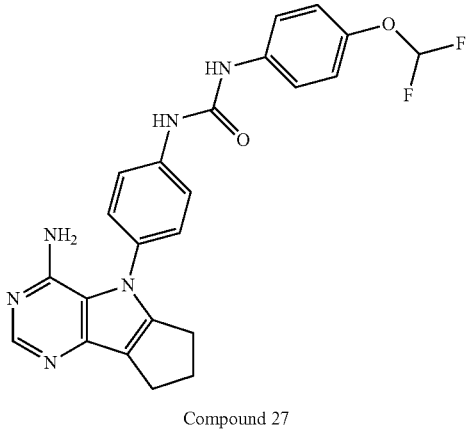
Compound 27

To a solution of compound 2 (150 mg, 0.56 mmol) in THF (1 mL) and DCM (3 mL) was added 4-(difluoromethoxy)phenyl isocyanate (87 uL, 0.62 mmol) and the reaction was then stirred at room temperature for 30 minutes. Volatiles were removed under reduced pressure. Purification by reverse phase chromatography eluting with 10-70% methanol in 1% HCl gradient provided compound 27.HCl as white solid. MS (m/z) M+H=451.1

Synthesis of Compound 30

Scheme 7

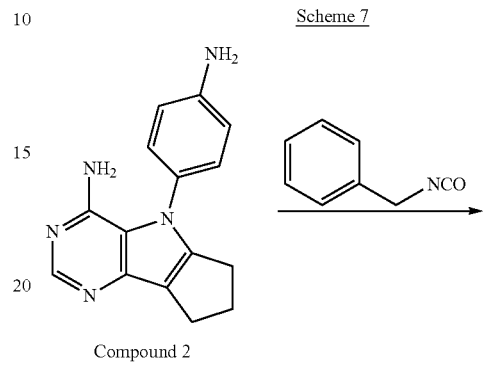
Compound 2

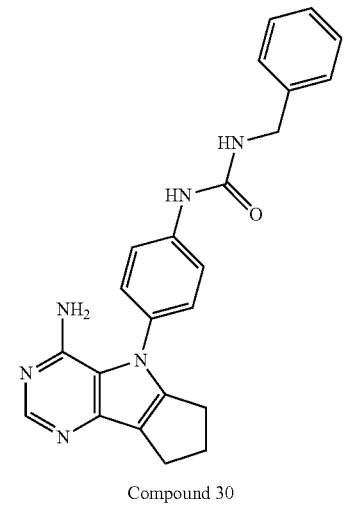
Compound 30

To a solution of compound 2 (100 mg, 0.37 mmol) in THF (1 mL) and DCM (3 mL) was added benzyl isocyanate (51 uL, 0.41 mmol) and the reaction was then stirred at room temperature for 18 hours. Volatiles were removed under reduced pressure. Purification by reverse phase chromatography eluting with 10-70% methanol in 1% HCl gradient provided compound 30.HCl as white solid. MS (m/z) M+H=399.2

Synthesis of Compound 31

Scheme 8

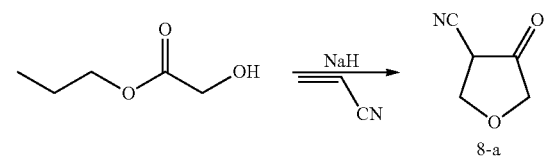
8-a

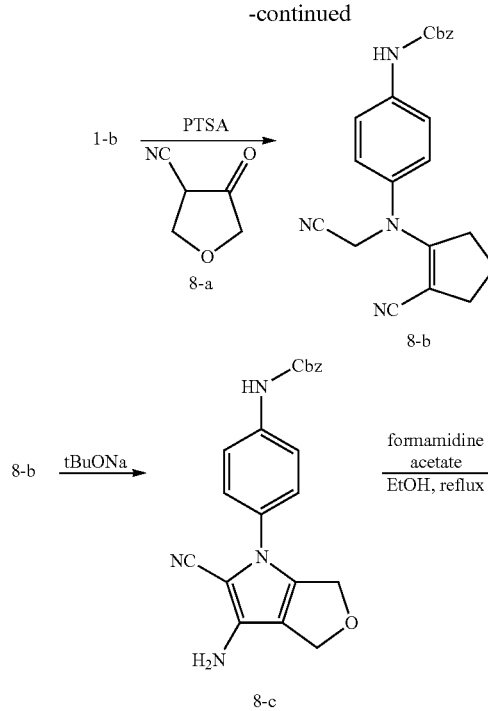

Step 3: Intermediate 8-c

To a solution of intermediate 8-b (2.0 g, 5.34 mmol) in tert-butanol (25 mL) was added potassium tert-butoxide (659 mg, 5.88 mmol) and the reaction was stirred at 80° C. for 30 minutes and then cooled to room temperature. 10% aqueous HCl and ethyl acetate were added, the organic layer was separated, the aqueous phase was extracted with ethyl acetate, the combined organic extracts were washed with brine, dried over MgSO$_4$, filtered and concentrated under reduced pressure to provide intermediate 8-c as brown solid.

Step 4: Compound 31

To a solution of intermediate 8-c (1.9 g, 5.07 mmol) in ethanol (50 ml) was added formamidine acetate (4.23 g, 40.6 mmol) and the reaction was stirred at 80° C. for 1.5 hour. The reaction was concentrated under reduced pressure. A saturated aqueous solution of NaHCO$_3$ and ethyl acetate were added, the organic layer was separated, washed with brine, dried over anhydrous MgSO$_4$, filtered and concentrated under reduced pressure to provide compound 31 as beige solid. MS (m/z) M+H=402.2

Synthesis of Compound 32

Scheme 9

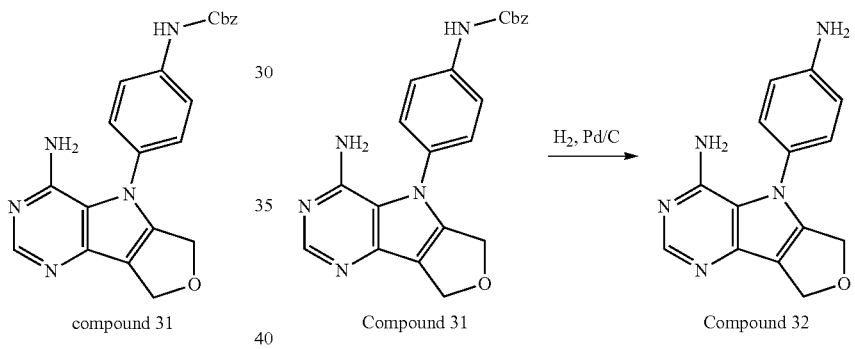

Step 1: Intermediate 8-a

A solution of butyl 2-hydroxyacetate (47.2 g, 357 mmol) in THF (50 mL) was added dropwise to a suspension of sodium hydride (14.28 g, 357 mmol) in THF (250 mL). The mixture is treated at reflux with a solution of crotonitrile (23.96 g, 357 mmol) in THF (50 mL) and the mixture is held at reflux for 2 hours then cooled to room temperature. The solvent was evaporated; 2N NaOH (200 mL) and diethyl ether (200 mL) were added to the residue. The organic layer was separated; the aqueous phase was extracted twice with diethyl ether and then acidified to pH 1 with concentrated HCl (75 mL). The aqueous phase was then extracted with 3 times with dichloromethane; the combined organic extracts were dried over MgSO$_4$, filtered and concentrated under vacuum to provide intermediate 8-a as brown oil.

Step 2: Intermediate 8-b

To a solution of intermediate 1-b (3.38 g, 12.0 mmol) in toluene (60 mL) were added intermediate 8-a (2.0 g, 18.0 mmol) and 4-methylbenzenesulfonic acid hydrate (228 mg, 1.20 mmol). The reaction was refluxed for 3 hours using a dean-stark and then cooled to room temperature. Saturated aqueous NaHCO$_3$ and ethyl acetate were added, the organic layer was separated, washed with brine, dried over MgSO$_4$, filtered and concentrated under reduced pressure. Purification by silica gel chromatography provided intermediate 8-b as beige solid.

A methanol solution of compound 31 (200 mg, 0.49 mmol) was treated with 10% Pd/C (106 mg, 0.05 mmol) and purged with H$_2$. The solution was stirred under H$_2$ (1 atm) for 45 minutes before being filtered through celite. The filtrate was concentrated in vacuo and purified by silica gel chromatography provided compound 32 as off-white solid. MS (m/z) M+H=268.2

Synthesis of Compound 33

Scheme 10

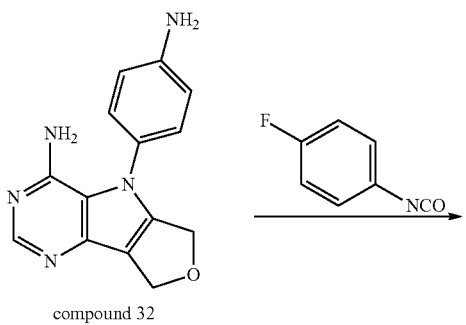

-continued

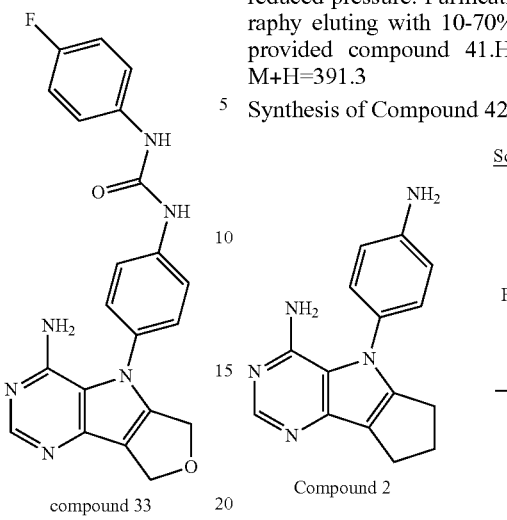

compound 33

To a solution of compound 32 (123 mg, 0.46 mmol) in dichloromethane (3 mL) was added 4-fluorophenyl isocyanate (63 mg, 0.46 mmol), acetic acid (0.5 mL) and the reaction was then stirred at room temperature for 30 minutes. Volatiles were removed under reduced pressure. Purification by reverse phase chromatography eluting with 10-40% methanol in 1% HCl gradient provided compound 33.HCl as beige solid. MS (m/z) M+H=405.2

Synthesis of Compound 41

Scheme 11

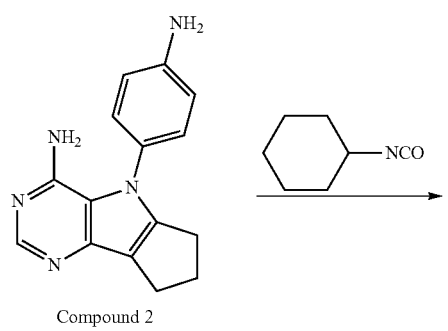

Compound 2

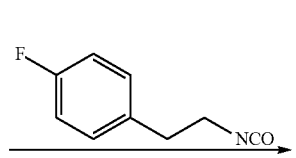

Compound 41

To a solution of compound 2 (156 mg, 0.58 mmol) in DCM (5 mL) was added cyclohexyl isocyanate (79 uL, 0.62 mmol), acetic acid (0.5 mL) and the reaction was then stirred at room temperature for 18 hours. Volatiles were removed under reduced pressure. Purification by reverse phase chromatography eluting with 10-70% methanol in 1% HCl gradient provided compound 41.HCl as beige solid. MS (m/z) M+H=391.3

Synthesis of Compound 42

Scheme 12

Compound 2

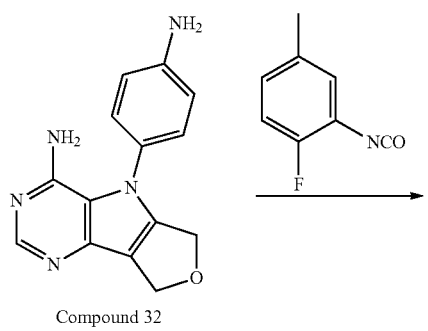

Compound 42

To a solution of compound 2 (112 mg, 0.42 mmol) in DCM (3 mL) was added 1-fluoro-4(2-isocyanatoethyl)benzene (77 mg, 0.46 mmol), acetic acid (0.6 mL) and the reaction was then stirred at room temperature for 18 hours. Volatiles were removed under reduced pressure. Purification by reverse phase chromatography eluting with 10-70% methanol in 1% HCl gradient provided compound 42.HCl as beige solid. MS (m/z) M+H=431.2

Synthesis of Compound 47

Scheme 13

Compound 32

-continued

Compound 47

To a solution of compound 32 (200 mg, 0.74 mmol) in DCM (3 mL) was added 1-fluoro-2-isocyanato-4-methylbenzene (113 mg, 0.74 mmol), acetic acid (0.5 mL) and the reaction was then stirred at room temperature for 30 minutes. Volatiles were removed under reduced pressure. Purification by reverse phase chromatography eluting with 10-40% methanol in 1% HCl gradient provided compound 47.HCl as beige solid. MS (m/z) M+H=419.2

Synthesis of Compound 48

Scheme 14

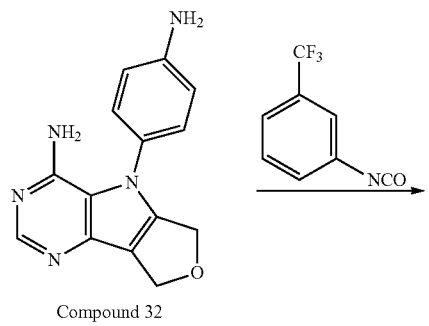

Compound 32

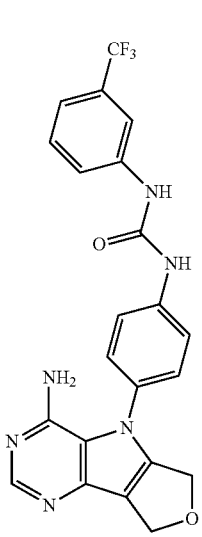

Compound 48

To a solution of compound 32 (154 mg, 0.57 mmol) in acetic acid (5 mL) was added 1-isocyanato-3-(trifluoromethyl)benzene (108 mg, 0.57 mmol) and the reaction was then stirred at room temperature overnight. Volatiles were removed under reduced pressure. Purification by reverse phase chromatography eluting with 10-40% methanol in 1% HCl gradient provided compound 48.HCl as beige solid. MS (m/z) M+H=455.1

Synthesis of Compound 60

Scheme 15

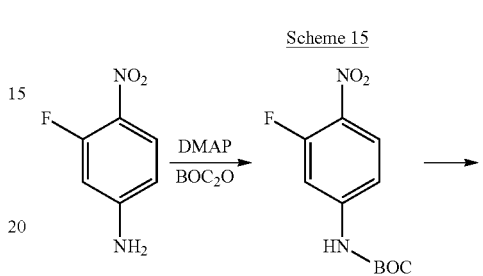

15-a

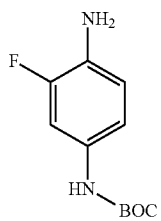

15-b

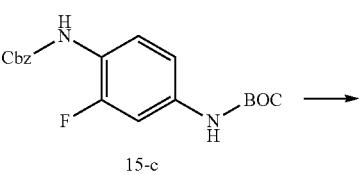

15-c

15-d

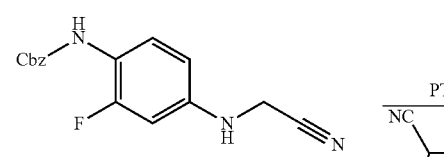

15-e

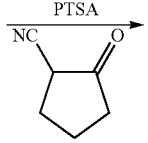

-continued

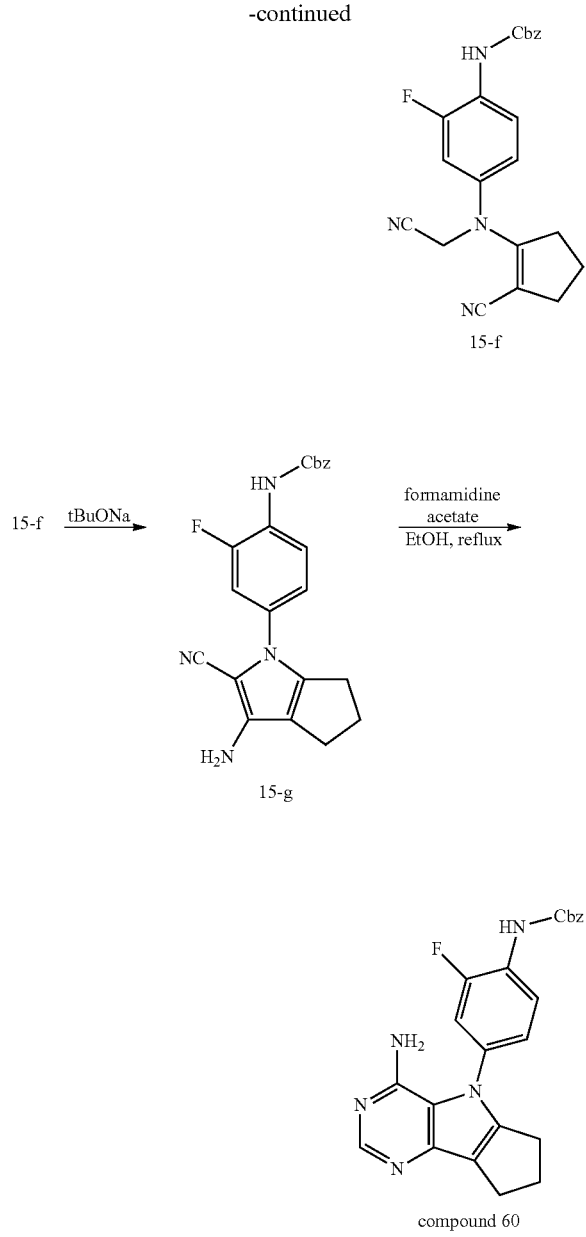

Step 1: Intermediate 15-a

To a solution of 3-fluoro-4-nitroaniline (5.0 g, 32.0 mmol) in dichloromethane (100 mL) was added BOC₂O (6.99 g, 32.0 mmol) and after stirring for 15 minutes, DMAP (391 mg, 3.20 mmol) was added. The reaction was stirred at room temperature for 2 days and then concentrated in vacuo. 10% citric acid and ethyl acetate were added; the organic layer was separated, washed with saturated aqueous NaHCO₃ and brine, dried over MgSO₄, filtered and concentrated under reduced pressure. Purification by silica gel chromatography provided intermediate 15-a as a yellow solid.

Step 2: Intermediate 15-b

A methanol solution of intermediate 15-a (1.7 g, 6.63 mmol) was treated with 10% Pd/C (1.41 g, 0.66 mmol) and purged with H₂. The solution was stirred under H₂ (1 atom.) overnight before being filtered through celite. The filtrate was concentrated in vacuo to provide intermediate 15-b as white solid.

Step 3: Intermediate 15-c

To a solution of intermediate 15-b (1.5 g, 6.63 mmol) in dichloromethane (66.0 mL), cooled to 0° C., were sequentially added benzyl chloroformate (943 µl, 6.63 mmol) and DIPEA (1.15 ml, 6.63 mmol) and the reaction was slowly warmed to room temperature and stirred overnight. The reaction was concentrated in vacuo. Water and ethyl acetate were added, the organic layer was separated, washed with brine, dried over MgSO₄, filtered and concentrated under reduced pressure to provide intermediate 15-c as beige oil.

Step 4: Intermediate 15-d

4N HCl in dioxane (10 ml, 40.0 mmol) was added to intermediate 15-c (2.17 g, 6.02 mmol) at 0° C. and the suspension was stirred at 0° C. for 1 hour. Volatiles were removed under reduced pressure and the residue was triturated with diethyl ether. A precipitate formed and was collected by filtration, dried under vacuum to provide intermediate 15-d as white solid. MS (m/z) M+H=261.1

Step 5: Intermediate 15-e

To a solution of intermediate 15-d (1.8 g, 6.07 mmol) and bromoacetonitrile (800 mg, 6.67 mmol) in THF (12.0 ml) was added DIPEA (2.22 ml, 12.74 mmol) at room temperature and the reaction mixture was then stirred at 80° C. overnight and then cooled to room temperature. A saturated aqueous ammonium chloride and ethyl acetate were added; the organic layer was separated, washed with saturated aqueous ammonium chloride and brine, dried over MgSO₄, filtered and concentrated under reduced pressure. Diethyl ether was added to the residue; a precipitate formed and was collected by filtration to provide intermediate 15-e as beige solid.

Step 6: Intermediate 15-f

To a solution of intermediate 15-e (1.8 g, 6.01 mmol) in toluene (30.0 ml), was added 2-oxocyclopentanecarbonitrile (984 mg, 9.02 mmol) and 4-methylbenzenesulfonic acid hydrate (114 mg, 0.60 mmol). The reaction was refluxed for 3 hours using a dean-stark and then cooled to room temperature. Saturated aqueous NaHCO₃ and ethyl acetate were added, the organic layer was separated, washed with brine, dried over MgSO₄, filtered and concentrated under reduced pressure. Purification by silica gel chromatography provided intermediate 15-f as beige solid. MS (m/z) M+H=391.5

Step 7: Intermediate 15-g

To a solution of intermediate 15-f (1.3 g, 3.33 mmol) in tert-butanol (33.0 mL) was added potassium tert-butoxide (411 mg, 3.66 mmol) and the reaction was stirred at 80° C. for 30 minutes and then cooled to room temperature. 10% aqueous HCl and ethyl acetate were added, the organic layer was separated, the aqueous phase was extracted with ethyl acetate, the combined organic extracts were washed with brine, dried over MgSO₄, filtered and concentrated under reduced pressure to provide intermediate 15-g as brown solid. MS (m/z) M+H=391.7

Step 8: Compound 60

To a solution of intermediate 15-h (1.3 g, 3.33 mmol) in ethanol (33 ml) was added formamidine acetate (2.77 g, 26.6 mmol) and the reaction was stirred at 80° C. for 1.5 hour. The reaction was concentrated under reduced pressure. A saturated aqueous solution of NaHCO₃ and ethyl acetate were added, the organic layer was separated, washed with brine, dried over anhydrous MgSO₄, filtered and concentrated under reduced pressure. Purification by reverse phase chromatography eluting with 10-50% methanol in 1% HCl gradient provided compound 60.HCl as beige solid. MS (m/z) M+H=418.1

Synthesis of Compound 61

Scheme 16

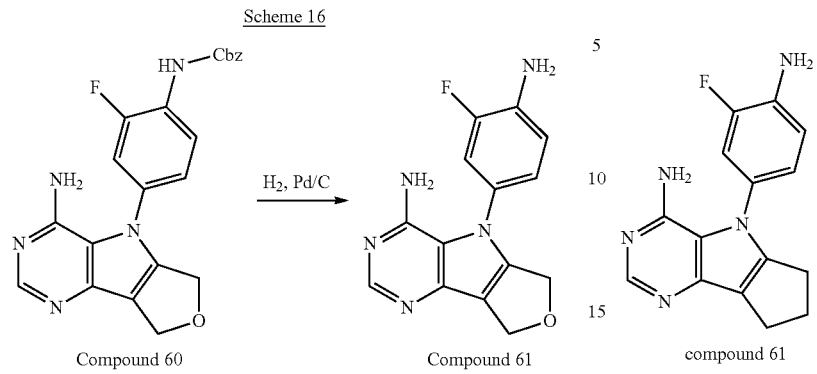

Compound 60 → Compound 61

A methanol solution of compound 60 (1.2 g, 2.87 mmol) was treated with 10% Pd/C (612 mg, 0.28 mmol) and purged with H$_2$. The solution was stirred under H$_2$ (1 atom.) for 45 minutes before being filtered through celite. The filtrate was concentrated in vacuo to provide compound 61 as an off-white solid.

Synthesis of Compound 62

Scheme 17

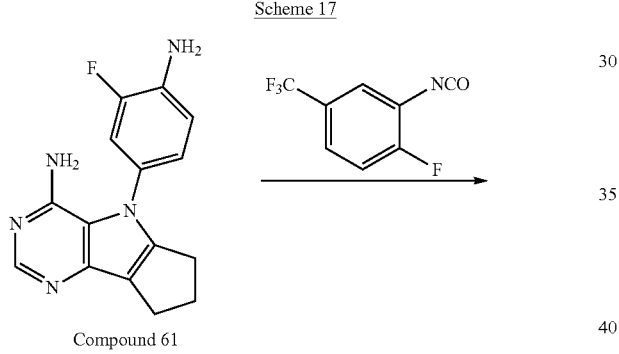

Compound 61 → Compound 62

To a solution of compound 61 (200 mg, 0.70 mmol) in AcOH (5 ml) was added 1-fluoro-2-isocyanato-4-(trifluoromethyl)benzene (145 mg, 0.76 mmol) and the reaction was then stirred at room temperature overnight. Volatiles were removed under reduced pressure. Purification by reverse phase chromatography eluting with 10-50% methanol in 1% HCl gradient provided compound 62.HCl as beige solid. MS (m/z) M+H=489.1

Synthesis of Compound 63

Scheme 18

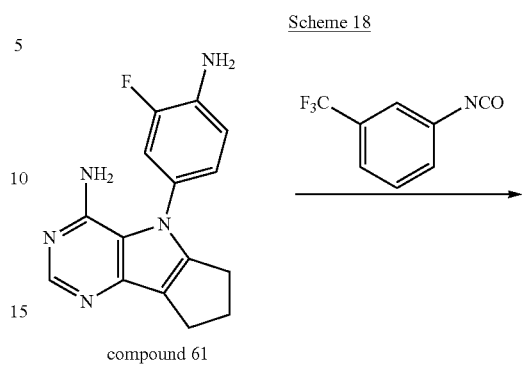

compound 61 → compound 63

To a solution of compound 61 (200 mg, 0.70 mmol) in AcOH (5 ml) was added 3-trifluoromethylphenyl isocyanate (132 mg, 0.70 mmol) and the reaction was then stirred at room temperature for 30 minutes. Ethyl acetate was added; a precipitate formed and was collected by filtration. Purification by reverse phase chromatography eluting with 10-50% methanol in 1% HCl gradient provided compound 63.HCl as white solid. MS (m/z) M+H=471.1

Synthesis of Compound 64

Scheme 19

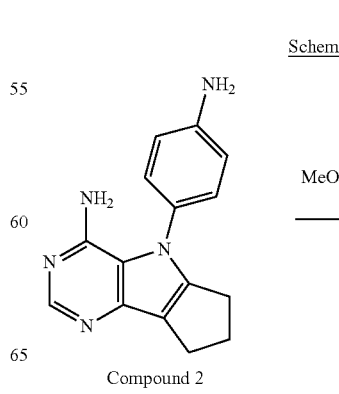

Compound 2

75
-continued

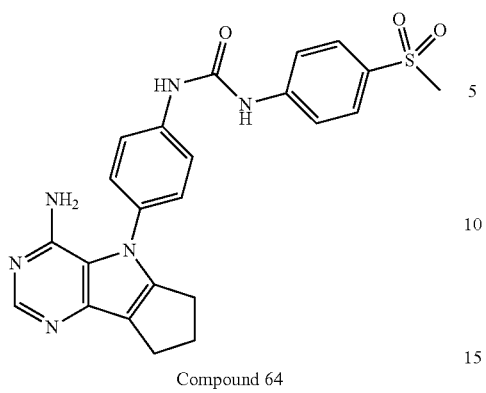

Compound 64

To a solution of compound 2 (119 mg, 0.45 mmol) in acetic acid (3 mL) was added 1-isocyanato-4-(methylsulfonyl)benzene (115 mg, 0.58 mmol) and the reaction was then stirred at room temperature for 30 minutes. Volatiles were removed under reduced pressure. Purification by reverse phase chromatography eluting with 10-70% methanol in 1% HCl gradient provided compound 64.HCl as white solid. MS (m/z) M+H=463.2

Synthesis of Compound 74

76
-continued

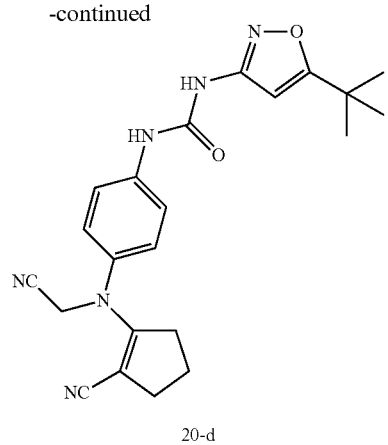

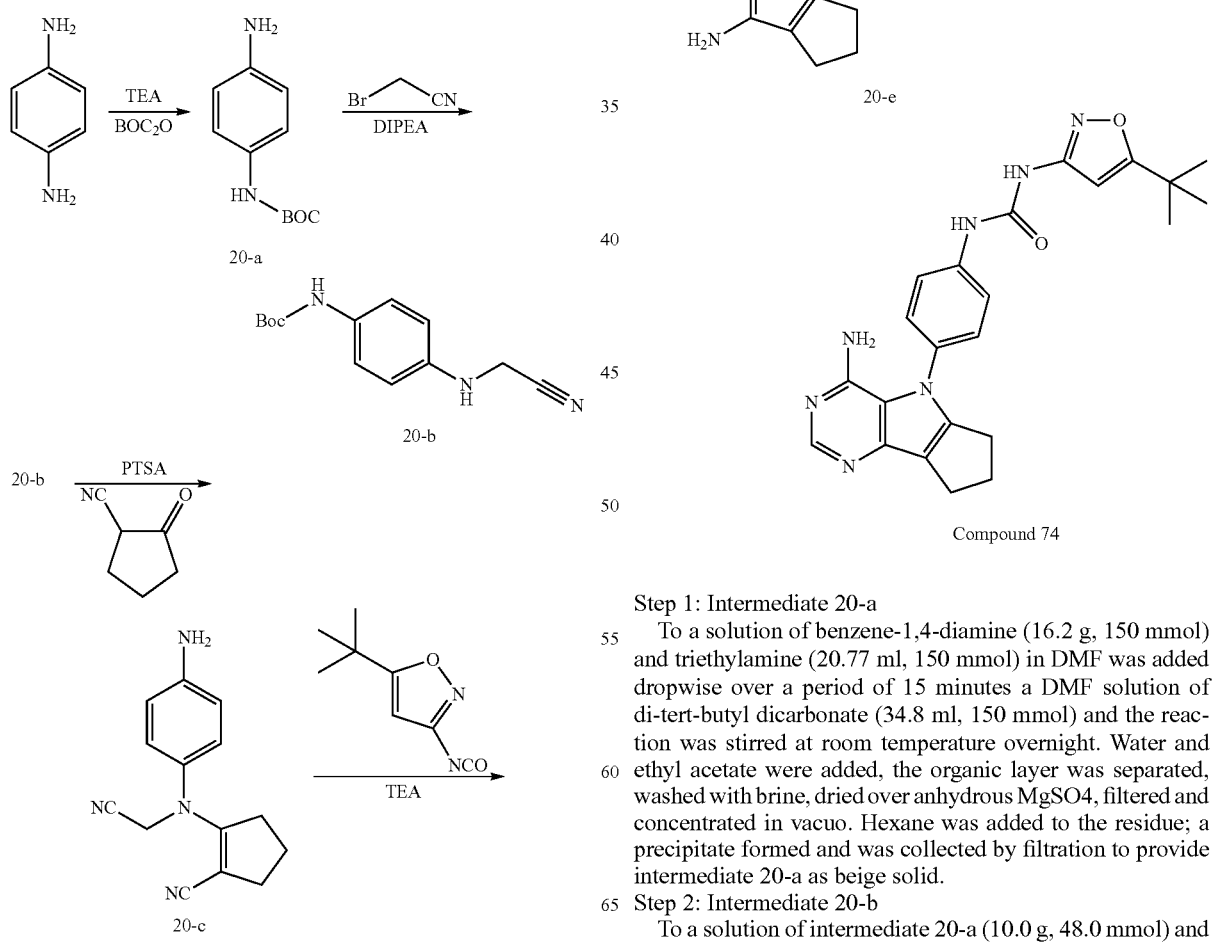

Step 1: Intermediate 20-a

To a solution of benzene-1,4-diamine (16.2 g, 150 mmol) and triethylamine (20.77 ml, 150 mmol) in DMF was added dropwise over a period of 15 minutes a DMF solution of di-tert-butyl dicarbonate (34.8 ml, 150 mmol) and the reaction was stirred at room temperature overnight. Water and ethyl acetate were added, the organic layer was separated, washed with brine, dried over anhydrous MgSO4, filtered and concentrated in vacuo. Hexane was added to the residue; a precipitate formed and was collected by filtration to provide intermediate 20-a as beige solid.

Step 2: Intermediate 20-b

To a solution of intermediate 20-a (10.0 g, 48.0 mmol) and bromoacetonitrile (6.34 g, 52.8 mmol) in THF (150 ml) was added DIPEA (17.61 ml, 101 mmol) at room temperature. The reaction mixture was then stirred at 80° C. overnight and then cooled to room temperature. Saturated aqueous ammonium chloride and ethyl acetate were added, the organic layer was separated, washed with saturates aqueous ammonium chloride and brine, dried over MgSO$_4$, filtered and concentrated under reduced pressure. Diethyl ether was added to the residue; a precipitate formed and was collected by filtration to provide intermediate 20-b as beige solid.

Step 3: Intermediate 20-c

To a solution of intermediate 20-b (1.2 g, 4.85 mmol) in toluene (30.0 ml), was added 2-oxocyclopentanecarbonitrile (794 mg, 7.28 mmol) and 4-methylbenzenesulfonic acid hydrate (92 mg, 0.48 mmol). The reaction was refluxed for 3 hours using a dean-stark and then cooled to room temperature. Saturated aqueous NaHCO$_3$ and ethyl acetate were added, the organic layer was separated, washed with brine, dried over MgSO$_4$, filtered and concentrated under reduced pressure to provide intermediate 20-c as a brown solid.

Step 4: Intermediate 20-d

To a solution of intermediate 20-c (1.3 g, 4.73 mmol) in THF (25 mL) was added 5-tert-butyl-3-isocyanatoisoxazole (865 mg, 5.20 mmol) and the reaction was stirred at reflux for 1 hour and then cooled to room temperature. Volatiles were removed under reduced pressure. Hexanes were added to the residue; a precipitate formed and was collected by filtration to provide intermediate 20-d as a brown solid.

Step 5: Intermediate 20-e

To a solution of intermediate 20-d (1.9 g, 4.70 mmol) in tert-butanol (23.0 mL) was added potassium tert-butoxide (580 mg, 5.17 mmol) and the reaction was stirred at 80° C. for 30 minutes and then cooled to room temperature. 10% aqueous HCl and ethyl acetate were added, the organic layer was separated, the aqueous phase was extracted with ethyl acetate, the combined organic extracts were washed with brine, dried over MgSO$_4$, filtered and concentrated under reduced pressure to provide intermediate 20-e as brown solid.

Step 6: Compound 74

To a solution of intermediate 20-e (1.9 g, 4.70 mmol) in ethanol (23 ml) was added formamidine acetate (3.91 g, 37.6 mmol) and the reaction was stirred at 80° C. for 30 minutes. The reaction was concentrated under reduced pressure. A saturated aqueous solution of NaHCO$_3$ and ethyl acetate were added, the organic layer was separated, washed with brine, dried over anhydrous MgSO$_4$, filtered and concentrated under reduced pressure. Purification by reverse phase chromatography eluting with 10-50% methanol in 1% HCl gradient provided compound 74.HCl. MS (m/z) M+H=432.2

Kinase Binding

Selected kinase binding affinities were determined using Kinase Profiler™ Service Assay Protocols (Millipore, V53.0).

Compound 14 inhibits cFMS(h), Aurora-B(h), Flt3 (h), KDR(h), PDGFR-b(h), FGFR1, Tie2, and FLT4 at a concentration of 100 nM.

Compound 44 inhibits cFMS, Flt3, KDR, FGFR1, and EphA2 at 100 nM. As a measure of selectivity, 216 other kinases were inhibited by 20% or less at 300 nM.

Biochemical cFMS (CSF1R) Assay:

Fluorescence polarization-based kinase biochemical assays were performed in 384 well-plate format using histidine tagged recombinant human colony stimulating factor 1 receptor (FMS) supplied from Invitrogen™ (containing the catalytic domain (amino acids 538-910), expressed in insect cells and activated in vitro via auto phosphorylation) and a modified protocol of the KinEASE™ FP Fluorescein Green Assay supplied from Millipore™.

Kinase reactions were performed in 384 well plate format at room temperature for 60 minutes in presence of 100 μM substrate, 10 μM ATP and variable test article concentrations. The reaction was stopped with EDTA/KinEASE™ detection reagents and the polarization measured on a Tecan 500 instrument. From the dose-response curve obtained, the IC$_{50}$ was estimated using Graph pad Prisms® using a non linear fit curve.

TABLE 2

| Compound | cFMS IC$_{50}$ |
|---|---|
| 3 | c |
| 4 | a |
| 9 | c |
| 10 | c |
| 11 | a |
| 12 | c |
| 14 | b |
| 16 | b |
| 17 | b |
| 19 | a |
| 20 | b |
| 21 | b |
| 23 | b |
| 27 | a |
| 28 | a |
| 30 | b |
| 33 | b |
| 35 | a |
| 36 | b |
| 39 | b |
| 41 | b |
| 43 | a |
| 44 | b |
| 45 | b |
| 46 | b |
| 47 | b |
| 48 | a |
| 50 | b |
| 54 | a |
| 55 | b |
| 56 | a |
| 57 | b |
| 58 | b |
| 59 | b |
| 62 | b |
| 63 | b |
| 64 | b |
| 65 | c |
| 66 | b |
| 67 | b |
| 68 | b |
| 69 | b |
| 71 | c |
| 72 | b |
| 73 | b |
| 74 | a |

IC$_{50}$ a: less than 100 nM; b: between 100 and 1000 nM; c: greater than 1000 nM.

Cellular Assays:

Murine M-CSF-Dependent M-NFS-60 Cell Survival Assay

Murine M-NFS-60 M-CSF-dependent myeloid leukemia cells were purchased from ATCC (CRL-1838). Cells were routinely cultured at 37° C., 5% CO$_2$ in complete medium (RPMI supplemented with 10% FBS, 1% penicillin/streptomycin, 50 uM beta mercaptoethanol) containing 30 ng/ml recombinant murine M-CSF (Peprotech 315-02). For survival assays, cells were transferred to depleted medium (complete medium depleted of M-CSF) for 24 hours prior to initiation of each experiment. M-CSF-starved cells were harvested and re-suspended in complete medium containing 20 ng/ml M-CSF. Cells were seeded at 25,000 cells/well in 96-well plates and incubated for 1 hour at 37° C., 5% CO$_2$. Cells were treated with 1 uM or 10 uM compound curves in triplicate and cell survival was measured 72 hours later by Cell Titer-Glo Luminescent Assay (Promega). Luminescence was read using a Tecan Infinite F200 microplate reader. EC50 values (50% survival in the presence of compound as compared to vehicle treated controls) were calculated from non-linear fit dose response compound curves using GraphPad Prism Software.

Human MV4-11 Biphenotypic B Myelomonocytic Leukemia Cell Survival Assay

Biphenotypic B myelomonocytic leukemia MV4-11 cells (ATCC CRL-9591) were cultured in suspension at 37° C., 5% $CO_2$ in complete medium (RPMI supplemented with 10% FBS, 1% penicillin/streptomycin). One day prior to treatment, cells per seeded in 96-well plates at 8000 cells/well in complete medium. The following day, triplicate wells were treated with compound curves of 100, 1000 or 10,000 nM starting concentration according to compound potency. Cell survival was measured 72h later by Cell Titer-Glo Luminescent Assay (Promega). Luminescence was read using a Tecan Infinite F200 microplate reader. EC50 values (50% survival in the presence of compound as compared to vehicle treated controls) were calculated from non-linear fit dose response compound curves using CambridgeSoft BioAssay software (Perkin Elmer).

TABLE 3

Results of the Cellular Assays

| Compound | $EC_{50}$ M-NFS-60 (nM) | $EC_{50}$ MV4-11 (nM) |
|---|---|---|
| 2 | — | a |
| 3 | c | c |
| 4 | a | a |
| 5 | — | c |
| 6 | — | c |
| 7 | — | c |
| 8 | — | c |
| 9 | c | b |
| 10 | c | c |
| 11 | a | a |
| 12 | c | c |
| 13 | a | a |
| 14 | a | a |
| 15 | — | c |
| 16 | a | a |
| 17 | a | a |
| 18 | — | b |
| 19 | a | b |
| 20 | a | b |
| 21 | a | b |
| 22 | a | b |
| 23 | b | c |
| 26 | — | c |
| 27 | a | a |
| 28 | a | a |
| 29 | — | c |
| 30 | b | a |
| 31 | — | b |
| 32 | — | b |
| 33 | b | b |
| 34 | — | c |
| 35 | b | a |
| 36 | b | c |
| 37 | — | c |
| 38 | b | c |
| 39 | a | b |
| 40 | — | b |
| 41 | b | a |
| 42 | b | a |
| 43 | a | a |
| 44 | b | a |
| 45 | b | a |
| 46 | b | a |
| 47 | a | a |
| 48 | b | a |

TABLE 3-continued

Results of the Cellular Assays

| Compound | $EC_{50}$ M-NFS-60 (nM) | $EC_{50}$ MV4-11 (nM) |
|---|---|---|
| 49 | — | b |
| 50 | a | a |
| 51 | — | c |
| 52 | b | a |
| 53 | — | c |
| 54 | a | a |
| 55 | b | a |
| 56 | a | a |
| 57 | a | a |
| 58 | b | a |
| 59 | b | a |
| 62 | b | a |
| 63 | a | a |
| 64 | c | b |
| 65 | b | a |
| 66 | b | a |
| 67 | b | a |
| 68 | b | a |
| 69 | b | a |
| 70 | — | a |
| 71 | c | b |
| 72 | b | a |
| 73 | b | a |
| 74 | a | — |

$EC_{50}$ a: less than 100 nM; b: between 100 and 1000 nM; c: greater than 1000 nM.

We claim:

1. A compound of the Formula 1:

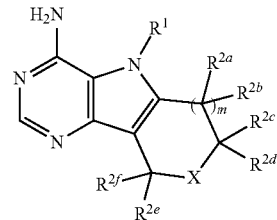

Formula 1 wherein m is an integer from 0 to 1;
n is an integer from 0 to 2;
$R^1$ is selected from alkyl, heteroalkyl, carbocyclyl, heterocyclyl, aryl, or heteroaryl, wherein the aryl and heteroaryl may be further substituted by the groups selected from:
1) Halogen,
2) Alkoxyl,
3) Amino,
4) —N(H)C(O)O-alkyl,
5) —N(H)SO$_2$-aryl,
6) —N(H)SO$_2$-heteroaryl,
7) —N(H)CON(H)-aryl,
8) and —N(H)CON(H)-heteroaryl;
$R^{2a}$, $R^{2b}$, $R^{2c}$, $R^{2d}$, $R^{2e}$, $R^{2f}$ are independently selected from hydrogen, alkyl, heteroalkyl, carbocyclyl, heterocyclyl, aryl, and heteroaryl; $R^{2a}$ and $R^{2b}$, $R^{2c}$ and $R^{2d}$, or $R^{2e}$ and $R^{2f}$ can be fused to form a 3 to 8 membered cycloalkyl or heterocyclyl ring system;
X is selected CH$_2$, O, S(O)$_n$, and NR$^3$;
$R^3$ is selected from hydrogen, alkyl, heteroalkyl, carbocyclyl, heterocyclyl, aryl, heteroaryl, .C(O)R$^4$, —C(O)OR$^4$, S(O)$_2$R$^4$, C(O)NR$^4$R$^5$, —S(O)$_2$NR$^4$R$^5$, and —C(S)NR$^4$R$^5$; and R⁴ and R⁵ are independently selected from alkyl, heteroalkyl, carbocyclyl, heterocyclyl, aryl, and heteroaryl, or R⁴ and R⁵ can be fused to form a 3 to 8 membered heterocyclyl ring system.

2. The compound according to claim 1, wherein Formula 1 is selected from the group consisting of:

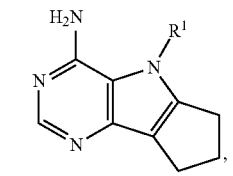
Formula 1a

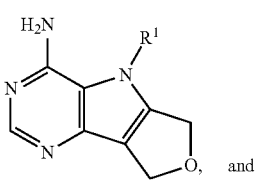
Formula 1b

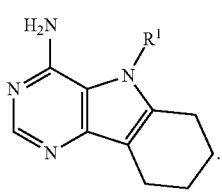
Formula 1c

3. A compound of claim 1 wherein R¹ is selected from the group consisting of:

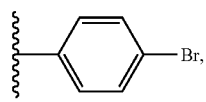
1

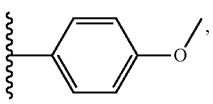
2

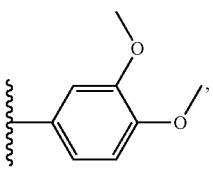
3

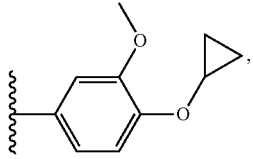
4

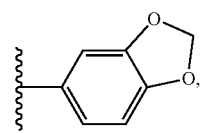
5

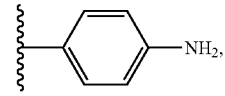
6

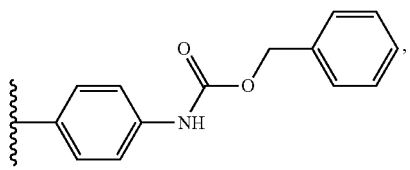
7

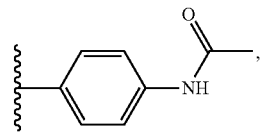
8

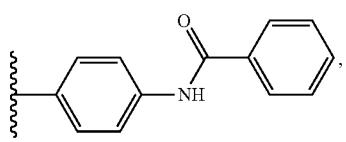
9

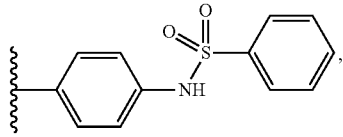
10

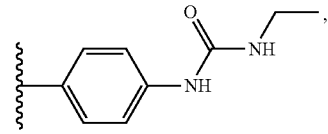
11

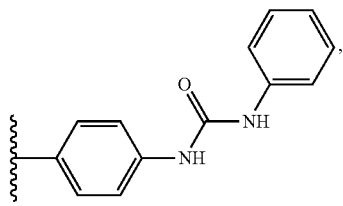
12

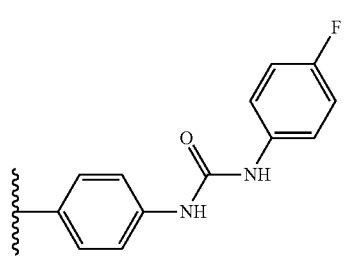
13

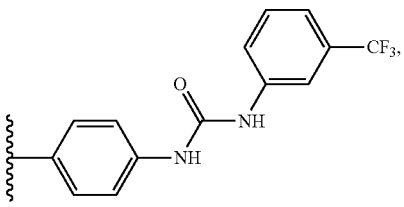
14

15 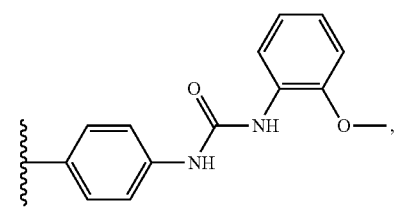
16 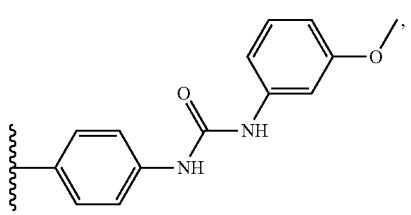
17 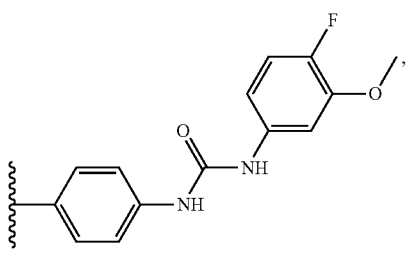
18 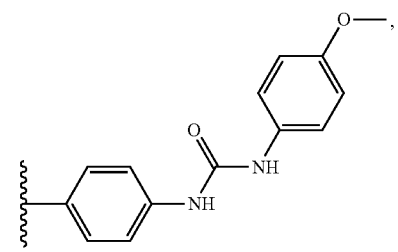
19 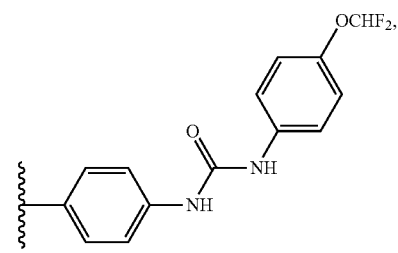
20 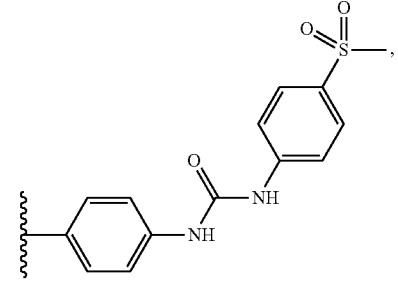
21 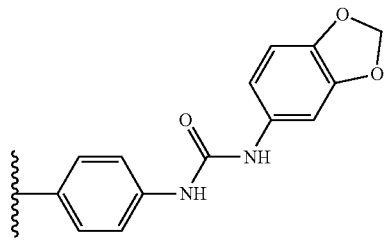
22 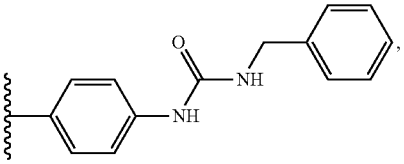
23 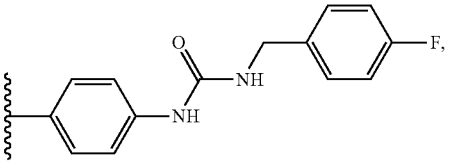
24 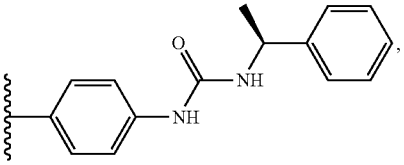
25 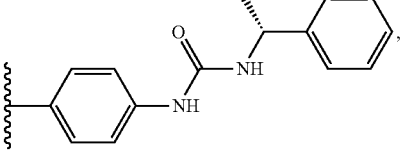
26 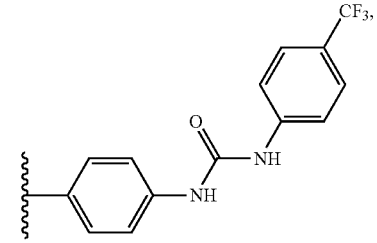
27 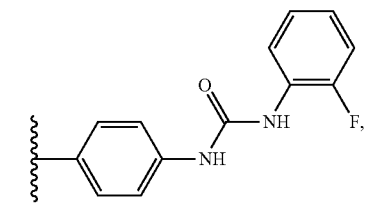
28 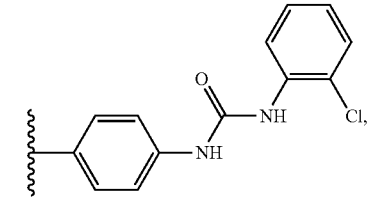

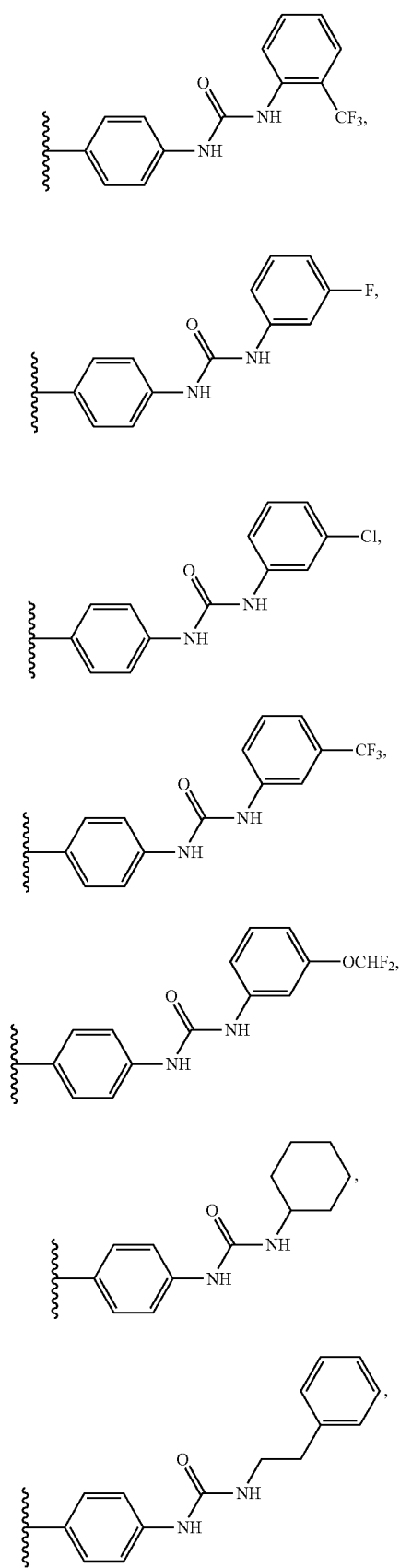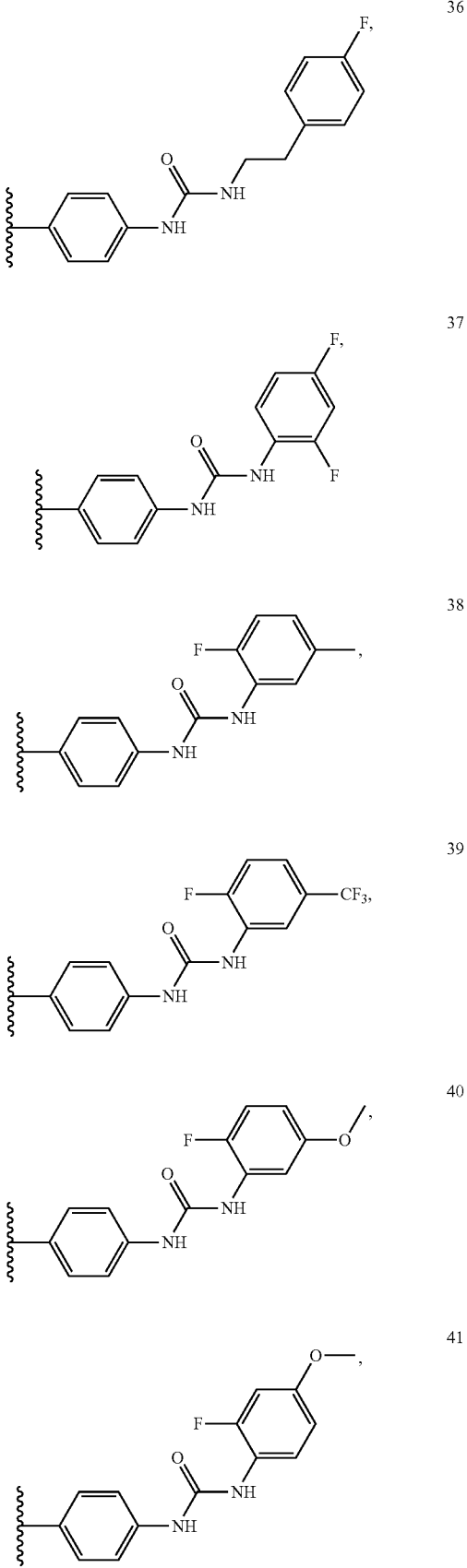

42 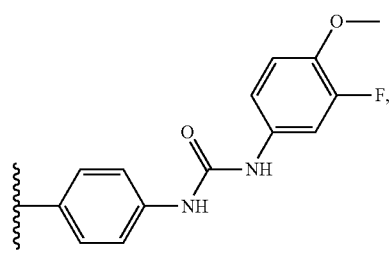
43 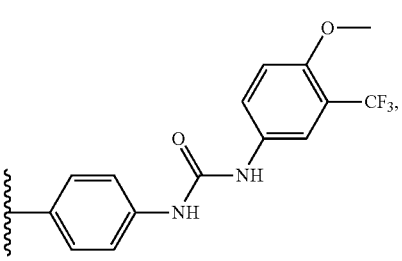
44 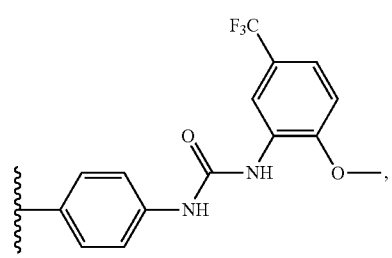
45 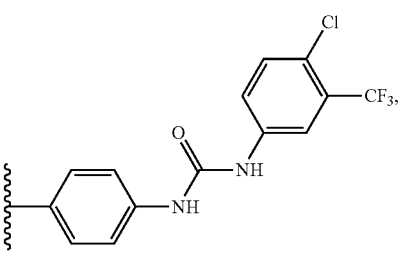
46 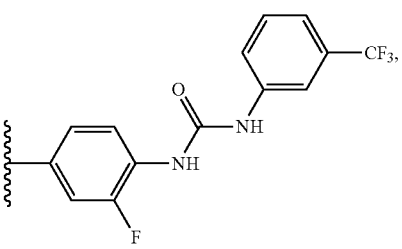
47 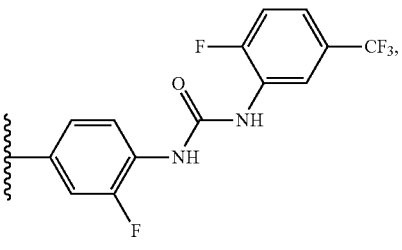
48 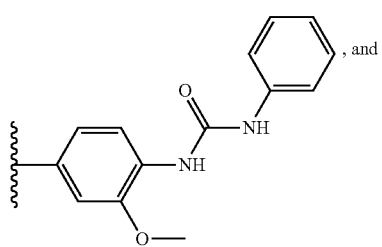
49 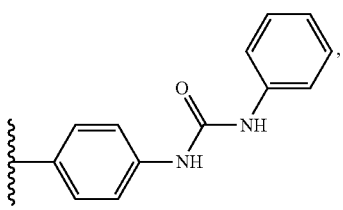
4. The compound according to claim 1 wherein $R^1$ is selected from the group consisting of:
1 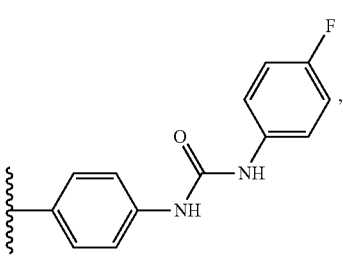
2 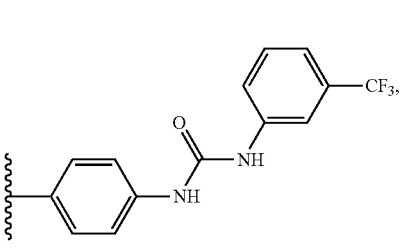
3 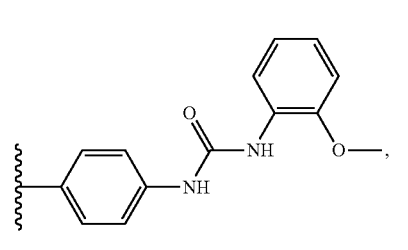
4

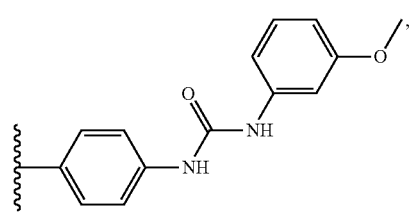
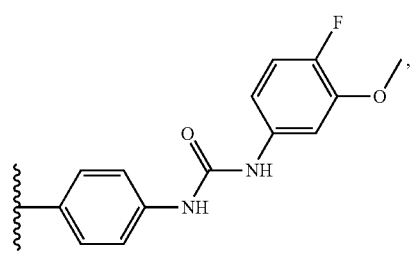
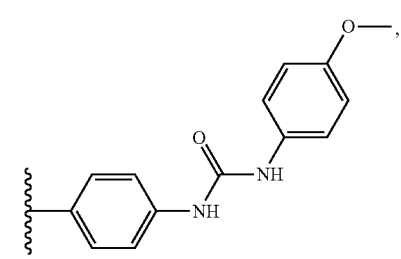
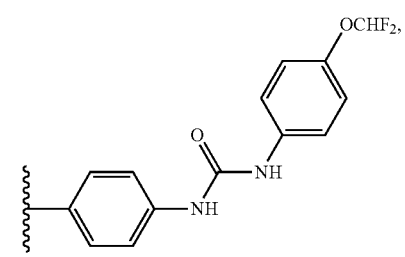
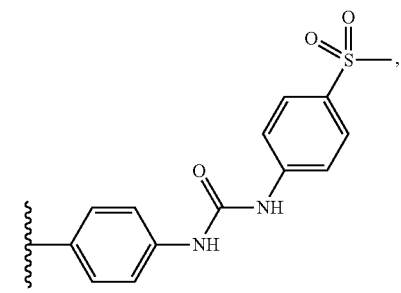
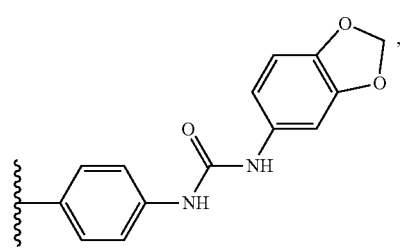
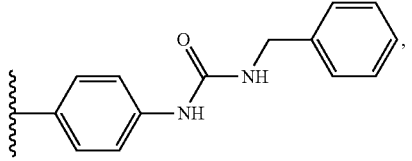
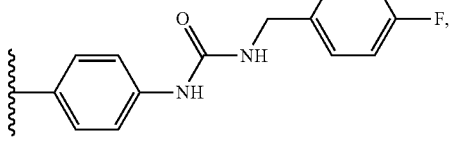
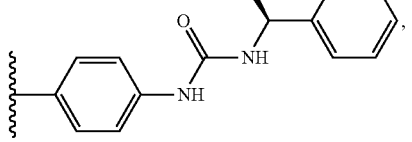
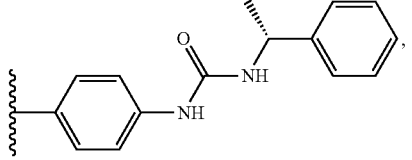
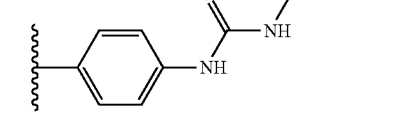
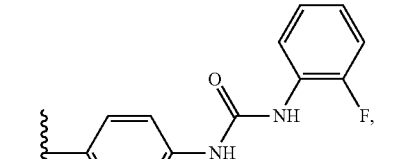
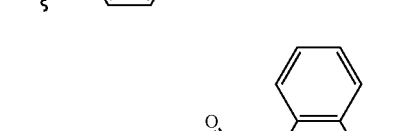
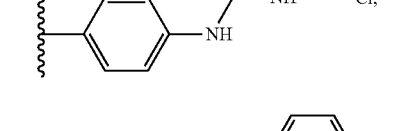
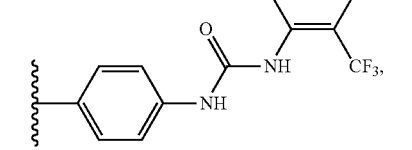

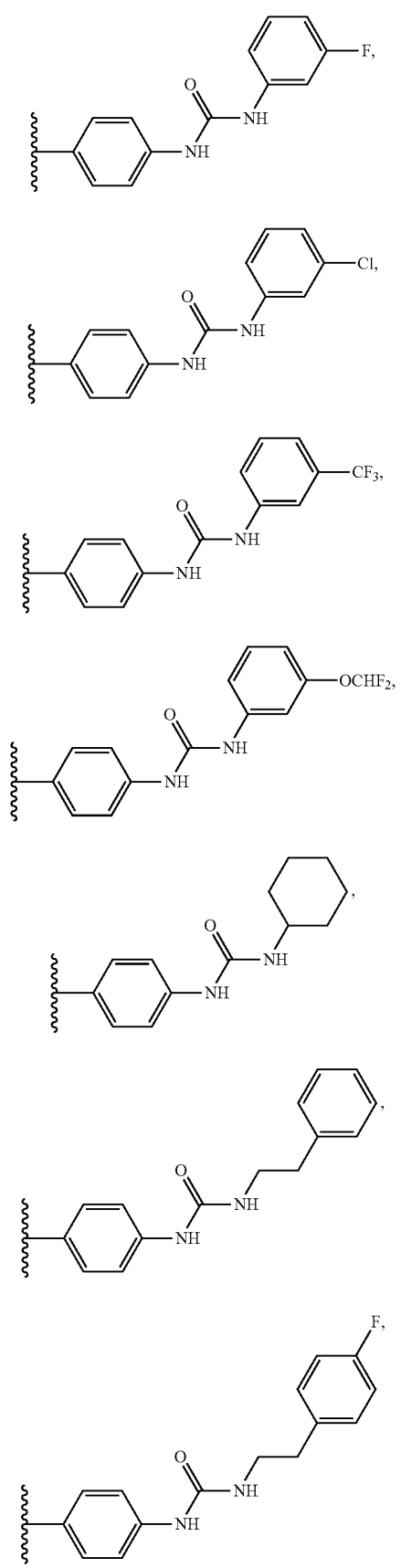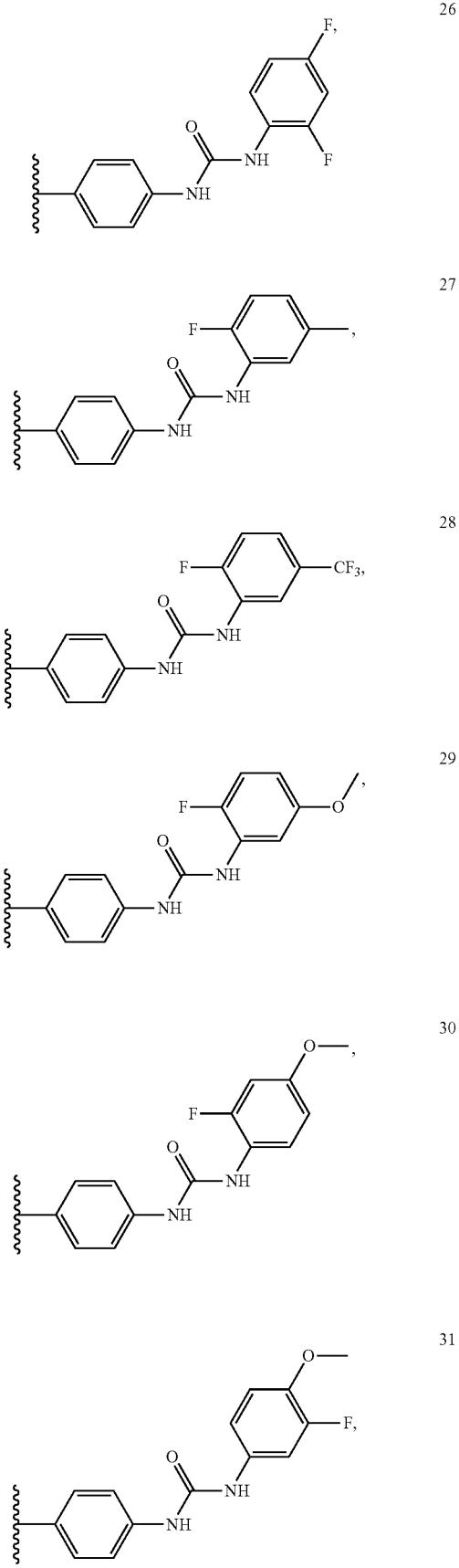

5. A compound selected from the group consisting of:
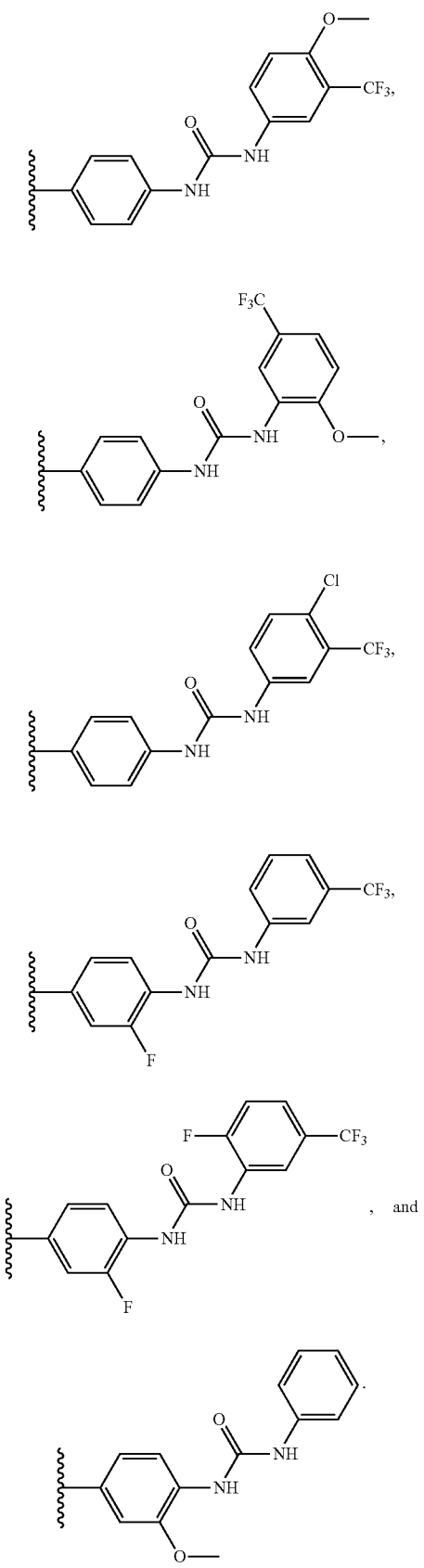

-continued
| Compound | Structure |
|---|---|
| 5 | 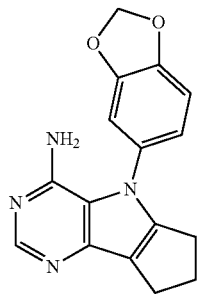 [SMILES: Nc1ncnc2c3c(n(-c4ccc5c(c4)OCO5)c12)CCC3] |
| 6 | 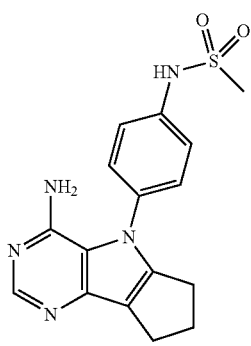 [SMILES: CS(=O)(=O)Nc1ccc(-n2c3c(c4ncnc(N)c42)CCC3)cc1] |
| 7 | 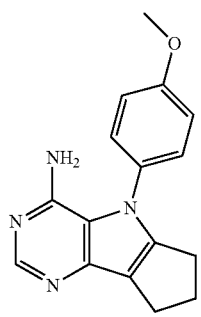 [SMILES: COc1ccc(-n2c3c(c4ncnc(N)c42)CCC3)cc1] |
| 8 | 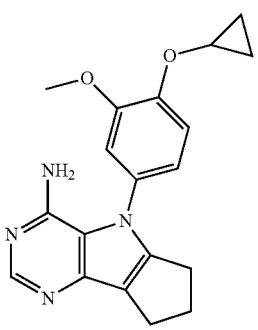 |
-continued
| Compound | Structure |
|---|---|
| 9 | 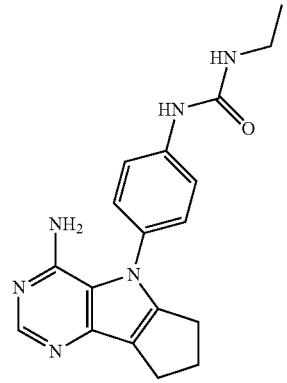 |
| 10 | 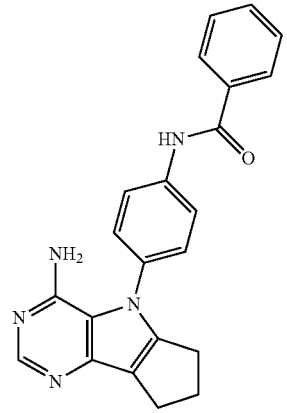 [SMILES: Nc1ncnc2c3c(n(-c4ccc(NC(=O)c5ccccc5)cc4)c12)CCC3] |
| 11 | 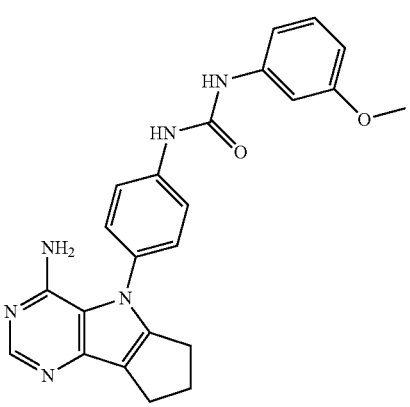 [SMILES: COc1cccc(NC(=O)Nc2ccc(-n3c4c(c5ncnc(N)c53)CCC4)cc2)c1] |
| 12 | 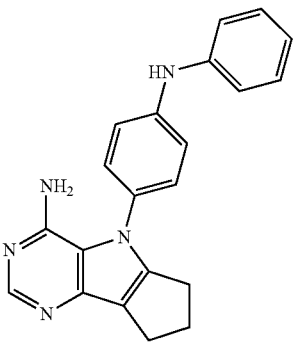 [SMILES: Nc1ncnc2c3c(n(-c4ccc(Nc5ccccc5)cc4)c12)CCC3] |

-continued

| Compound | Structure |
|---|---|
| 13 | *structure: N-(4-methoxyphenyl)-N'-[4-(4-amino-7,8-dihydro-6H-cyclopenta[4,5]pyrrolo[2,3-d]pyrimidin-5-yl)phenyl]urea* |
| 14 | *structure: N-(4-fluorophenyl)-N'-[4-(4-amino-7,8-dihydro-6H-cyclopenta[4,5]pyrrolo[2,3-d]pyrimidin-5-yl)phenyl]urea* |
| 15 | *structure: 5-benzyl-4-amino-7,8-dihydro-6H-cyclopenta[4,5]pyrrolo[2,3-d]pyrimidine* |
| 16 | *structure: N-(2-methoxyphenyl)-N'-[4-(4-amino-7,8-dihydro-6H-cyclopenta[4,5]pyrrolo[2,3-d]pyrimidin-5-yl)phenyl]urea* |

-continued

| Compound | Structure |
|---|---|
| 17 | *structure: N-[3-(trifluoromethyl)phenyl]-N'-[4-(4-amino-7,8-dihydro-6H-cyclopenta[4,5]pyrrolo[2,3-d]pyrimidin-5-yl)phenyl]urea* |
| 18 | *structure: 4-amino-5-(4-aminophenyl)-5,6,7,8-tetrahydropyrimido[4,5-b]indole* |
| 19 | *structure: N-(3-fluorophenyl)-N'-[4-(4-amino-7,8-dihydro-6H-cyclopenta[4,5]pyrrolo[2,3-d]pyrimidin-5-yl)phenyl]urea* |
| 20 | *structure: N-(3-chlorophenyl)-N'-[4-(4-amino-7,8-dihydro-6H-cyclopenta[4,5]pyrrolo[2,3-d]pyrimidin-5-yl)phenyl]urea* |

| Compound | Structure |
|---|---|
| 21 | 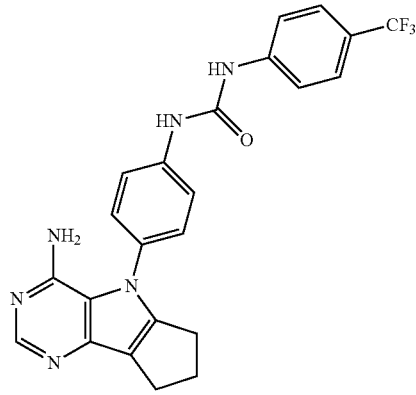 [SMILES: Nc1ncnc2c3c(n(-c4ccc(NC(=O)Nc5ccc(C(F)(F)F)cc5)cc4)c12)CCC3] |
| 22 | 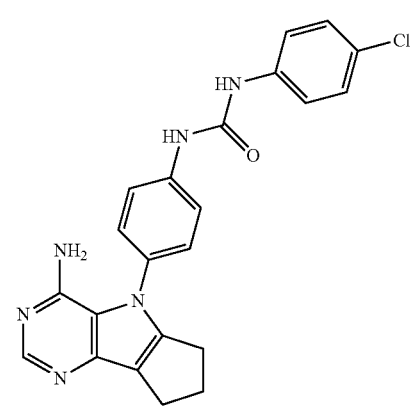 [SMILES: Nc1ncnc2c3c(n(-c4ccc(NC(=O)Nc5ccc(Cl)cc5)cc4)c12)CCC3] |
| 23 | 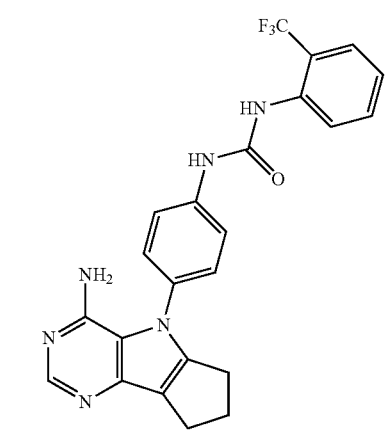 [SMILES: Nc1ncnc2c3c(n(-c4ccc(NC(=O)Nc5ccccc5C(F)(F)F)cc4)c12)CCC3] |
| 24 | 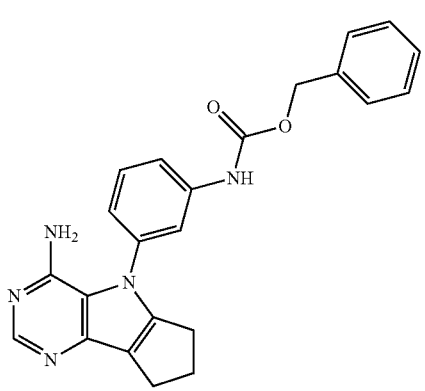 [SMILES: Nc1ncnc2c3c(n(-c4cccc(NC(=O)OCc5ccccc5)c4)c12)CCC3] |
| Compound | Structure |
|---|---|
| 25 | 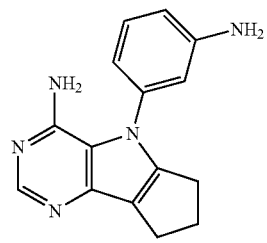 [SMILES: Nc1cccc(-n2c3c(c4ncnc(N)c42)CCC3)c1] |
| 26 | 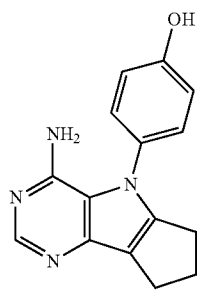 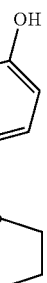 |
| 27 | 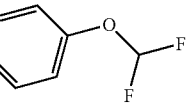 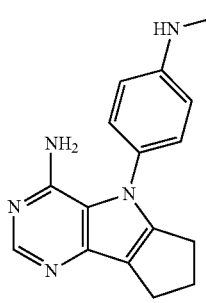 |
| 28 | 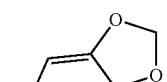 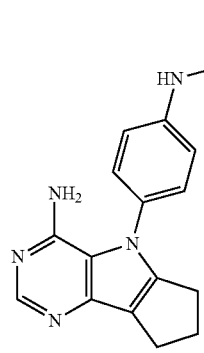 |

-continued
| Compound | Structure |
|---|---|
| 29 | 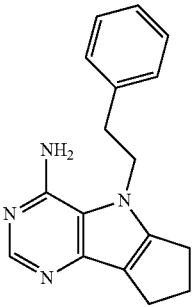 [SMILES: Nc1ncnc2c3c(n(CCc4ccccc4)c12)CCC3] |
| 30 | 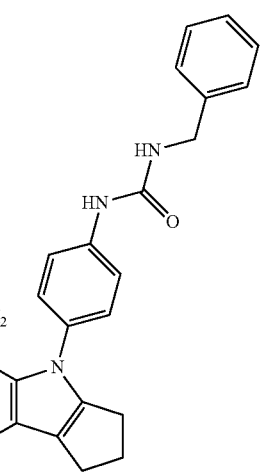 |
| 31 | 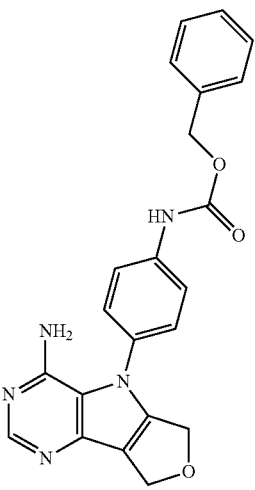 [SMILES: Nc1ncnc2c3c(n(-c4ccc(NC(=O)OCc5ccccc5)cc4)c12)COC3] |
| 32 | 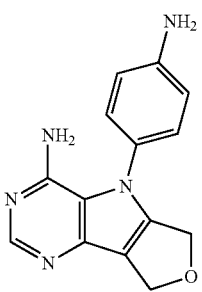 [SMILES: Nc1ccc(-n2c3c(c4ncnc(N)c42)COC3)cc1] |
-continued
| Compound | Structure |
|---|---|
| 33 | 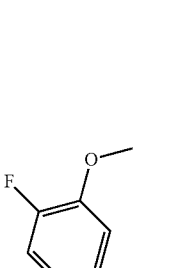 |
| 34 | 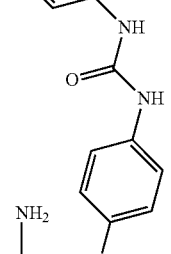 |
| 35 | 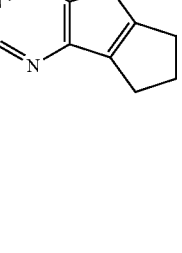 |

-continued
| Compound | Structure |
|---|---|
| 36 | 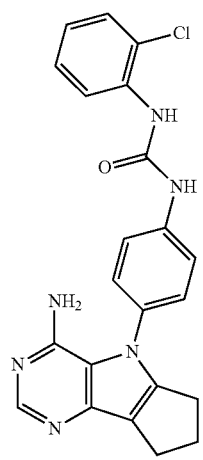 |
| 37 | 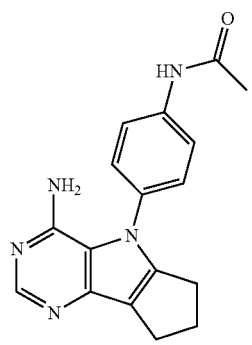 [SMILES: CC(=O)Nc1ccc(-n2c3c(c4ncnc(N)c42)CCC3)cc1] |
| 38 | 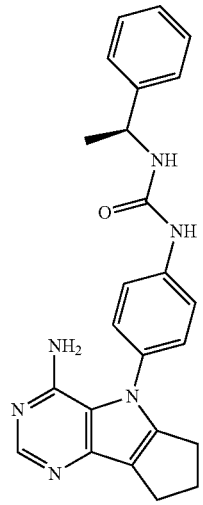 [SMILES: C[C@H](NC(=O)Nc1ccc(-n2c3c(c4ncnc(N)c42)CCC3)cc1)c1ccccc1] |
-continued
| Compound | Structure |
|---|---|
| 39 | 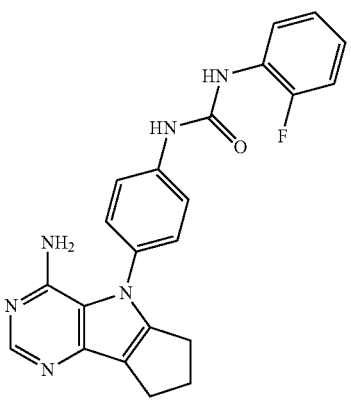 [SMILES: Nc1ncnc2c3c(n(-c4ccc(NC(=O)Nc5ccccc5F)cc4)c12)CCC3] |
| 40 | 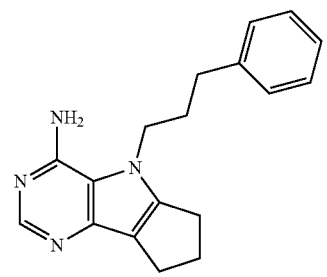 [SMILES: Nc1ncnc2c3c(n(CCCc4ccccc4)c12)CCC3] |
| 41 | 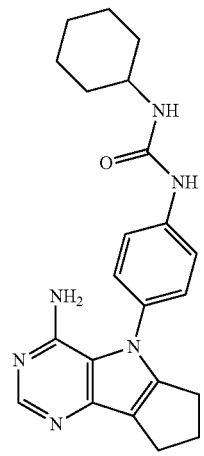 |

TABLE-continued
| Compound | Structure |
|---|---|
| 42 | 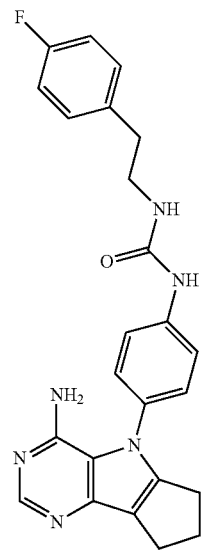 [SMILES: Nc1ncnc2c3c(n(-c4ccc(NC(=O)NCCc5ccc(F)cc5)cc4)c12)CCC3] |
| 43 | 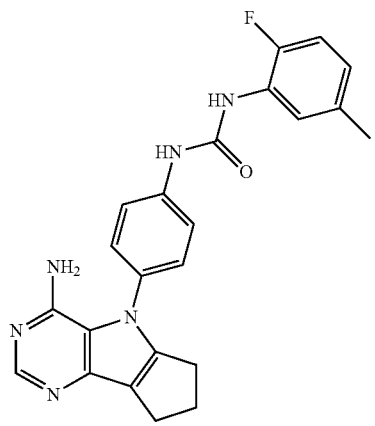 [SMILES: Cc1ccc(F)c(NC(=O)Nc2ccc(-n3c4c(c5ncnc(N)c53)CCC4)cc2)c1] |
| 44 | 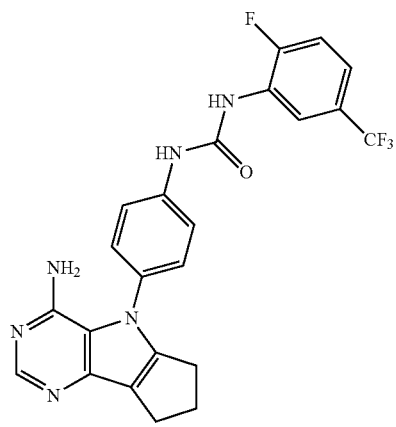 |
TABLE-continued
| Compound | Structure |
|---|---|
| 45 | 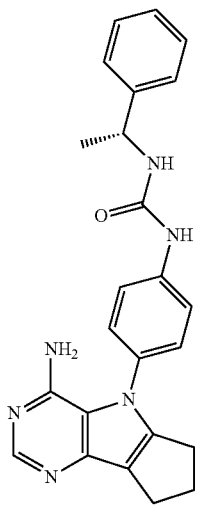 [SMILES: C[C@@H](NC(=O)Nc1ccc(-n2c3c(c4ncnc(N)c42)CCC3)cc1)c1ccccc1] |
| 46 | 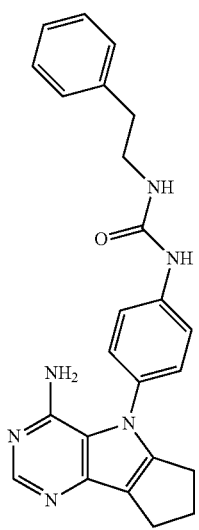 |
| 47 | 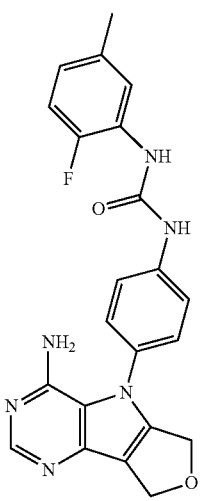 |

-continued

| Compound | Structure |
|---|---|
| 48 | (structure) |
| 49 | (structure) |
| 50 | (structure) |
| 51 | (structure) |

-continued

| Compound | Structure |
|---|---|
| 52 | (structure) |
| 53 | (structure) |
| 54 | (structure) |

-continued
| Compound | Structure |
|---|---|
| 55 | 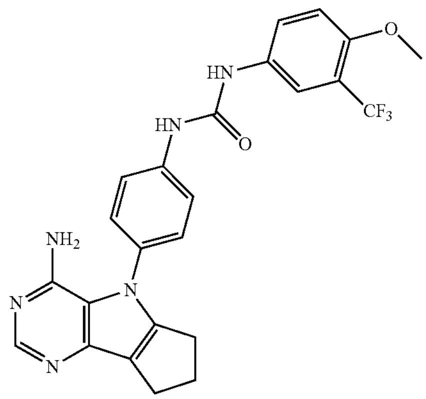 [SMILES: COc1ccc(NC(=O)Nc2ccc(-n3c4c(c5ncnc(N)c53)CCC4)cc2)cc1C(F)(F)F] |
| 56 | 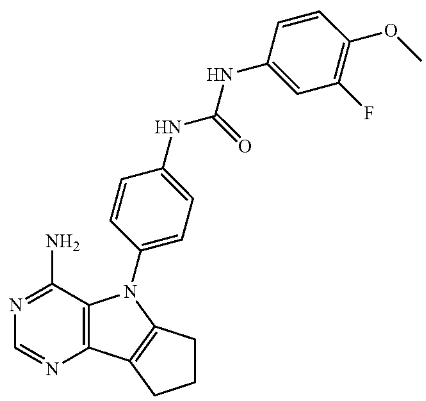 [SMILES: COc1ccc(NC(=O)Nc2ccc(-n3c4c(c5ncnc(N)c53)CCC4)cc2)cc1F] |
| 57 | 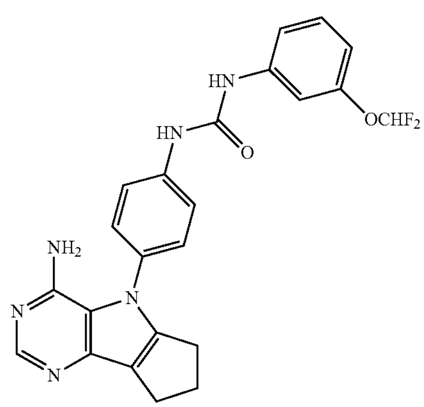 [SMILES: Nc1ncnc2c3c(n(-c4ccc(NC(=O)Nc5cccc(OC(F)F)c5)cc4)c12)CCC3] |
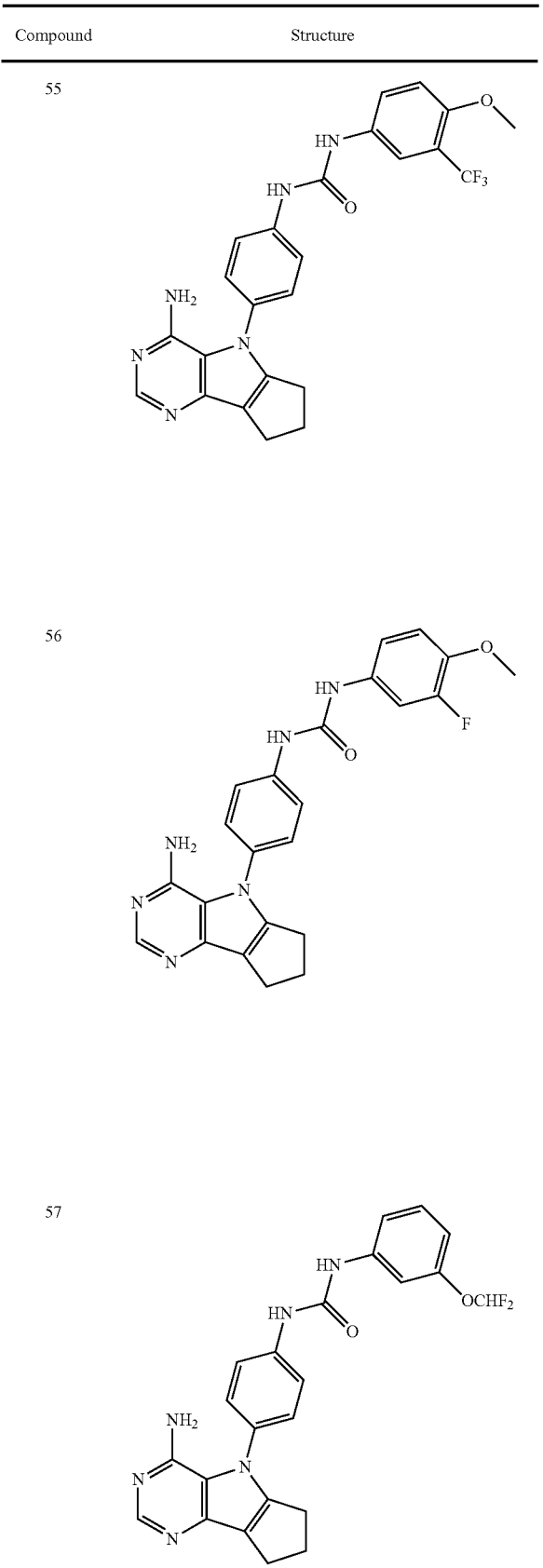
-continued
| Compound | Structure |
|---|---|
| 58 | 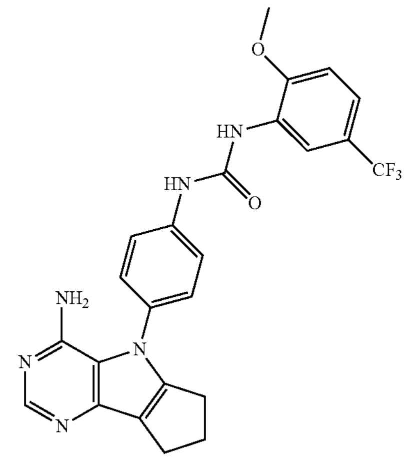 [SMILES: COc1ccc(C(F)(F)F)cc1NC(=O)Nc1ccc(-n2c3c(c4ncnc(N)c42)CCC3)cc1] |
| 59 | 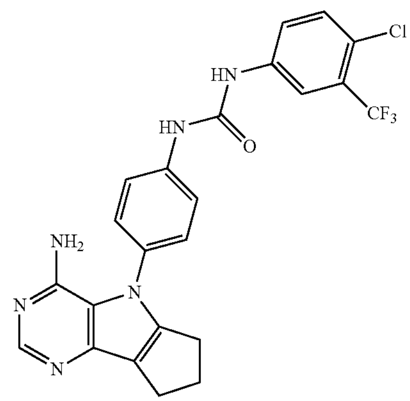 [SMILES: Nc1ncnc2c3c(n(-c4ccc(NC(=O)Nc5ccc(Cl)c(C(F)(F)F)c5)cc4)c12)CCC3] |
| 60 | 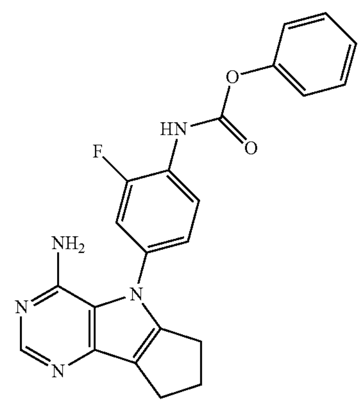 [SMILES: Nc1ncnc2c3c(n(-c4ccc(NC(=O)Oc5ccccc5)c(F)c4)c12)CCC3] |
| 61 | 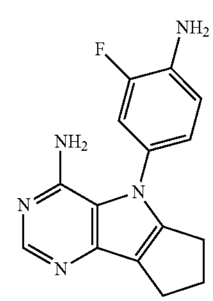 [SMILES: Nc1ccc(-n2c3c(c4ncnc(N)c42)CCC3)cc1F] |
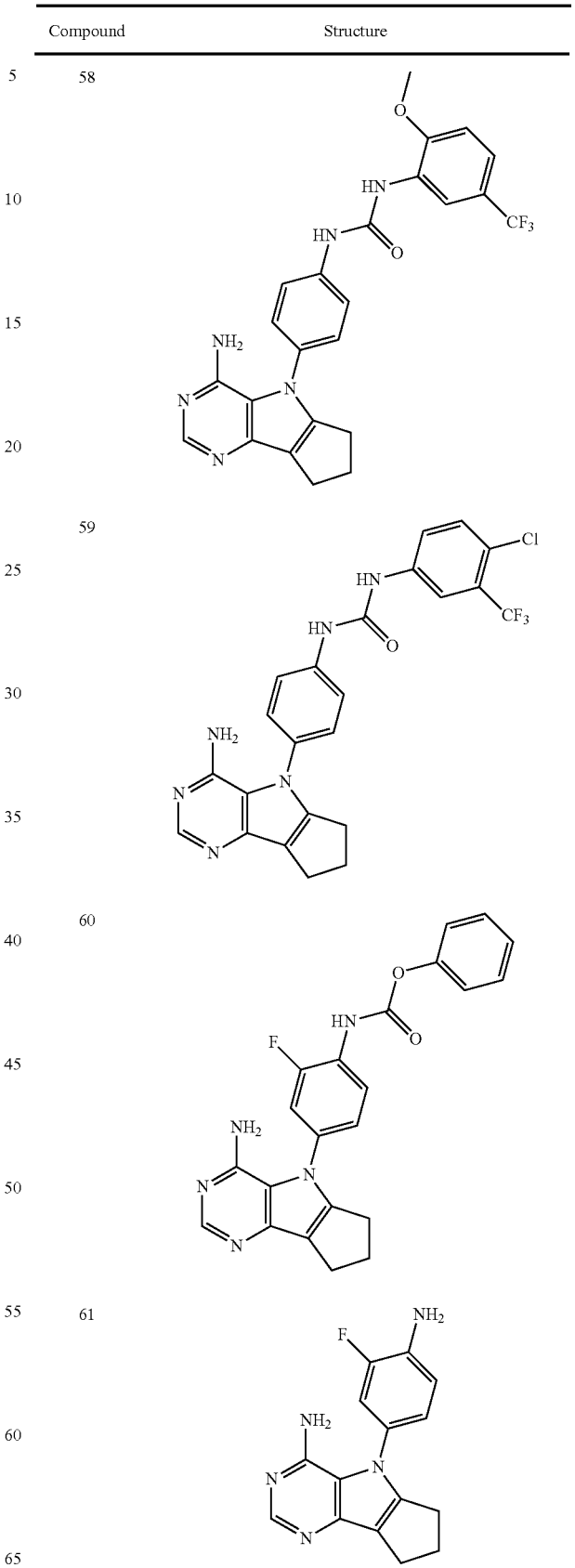

-continued
| Compound | Structure |
|----------|-----------|
| 62 | 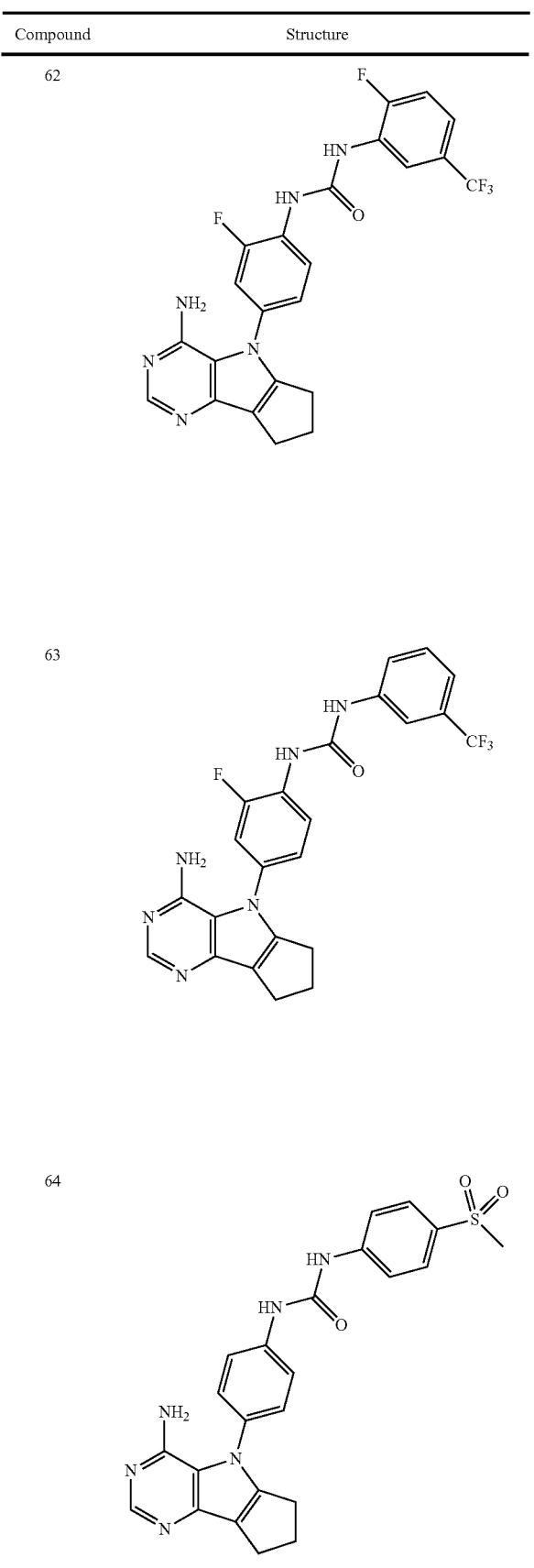 |
| 63 | 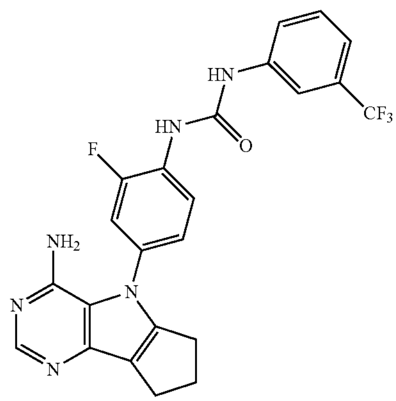 [SMILES: Nc1ncnc2c3c(n(-c4ccc(NC(=O)Nc5cccc(C(F)(F)F)c5)c(F)c4)c12)CCC3] |
| 64 | 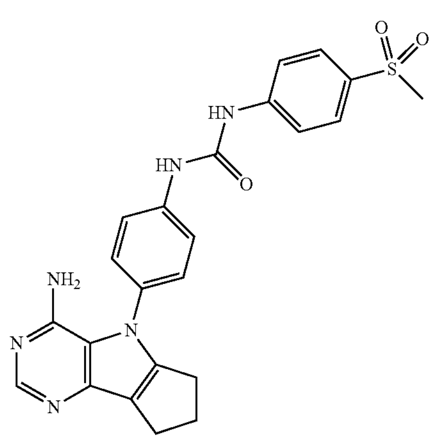 [SMILES: CS(=O)(=O)c1ccc(NC(=O)Nc2ccc(-n3c4c(c5ncnc(N)c53)CCC4)cc2)cc1] |
-continued
| Compound | Structure |
|----------|-----------|
| 65 | 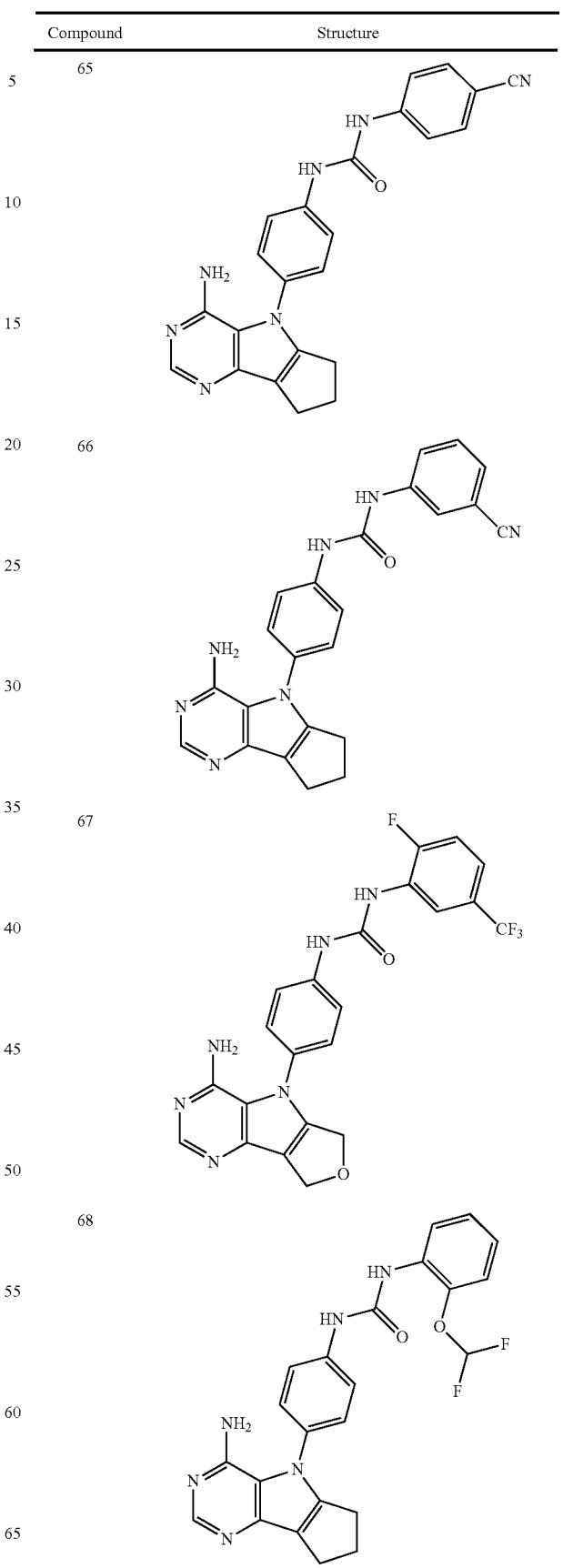 |
| 66 | 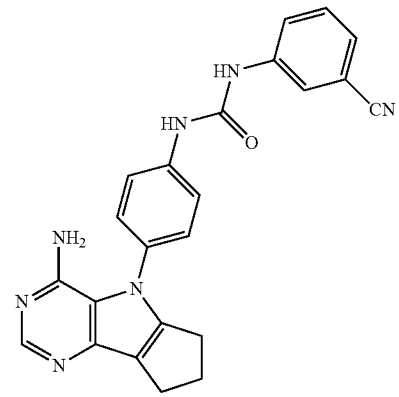 [SMILES: N#Cc1cccc(NC(=O)Nc2ccc(-n3c4c(c5ncnc(N)c53)CCC4)cc2)c1] |
| 67 | 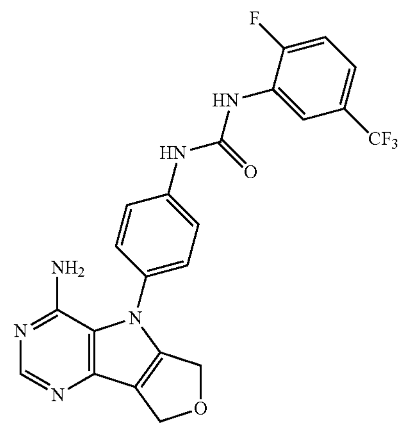 |
| 68 | 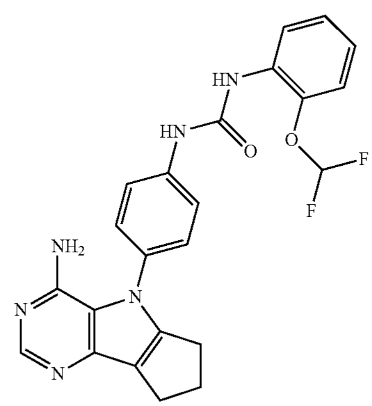 [SMILES: Nc1ncnc2c3c(n(-c4ccc(NC(=O)Nc5ccccc5OC(F)F)cc4)c12)CCC3] |

-continued
| Compound | Structure |
|---|---|
| 69 | 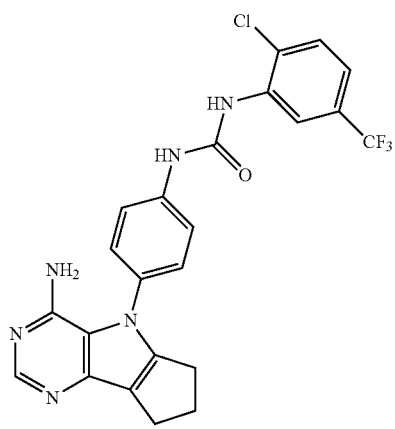 [SMILES: Nc1ncnc2c3c(n(-c4ccc(NC(=O)Nc5cc(C(F)(F)F)ccc5Cl)cc4)c12)CCC3] |
| 70 | 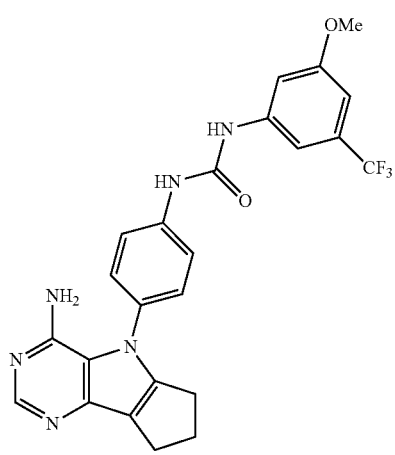 [SMILES: COc1cc(NC(=O)Nc2ccc(-n3c4c(c5ncnc(N)c53)CCC4)cc2)cc(C(F)(F)F)c1] |
| 71 | 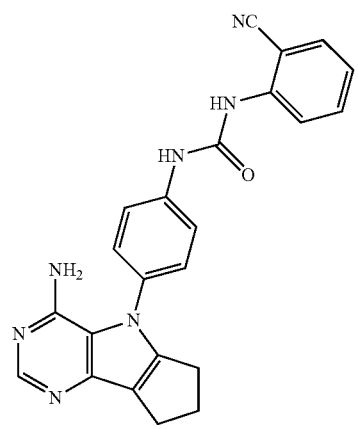 [SMILES: N#Cc1ccccc1NC(=O)Nc1ccc(-n2c3c(c4ncnc(N)c42)CCC3)cc1] |
-continued
| Compound | Structure |
|---|---|
| 72 | 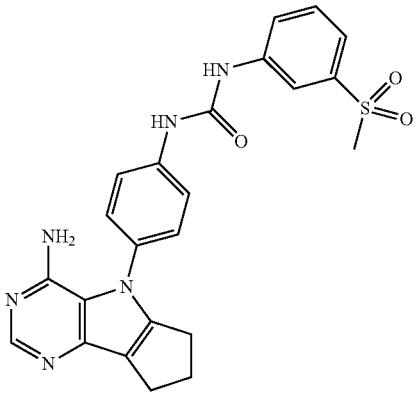 [SMILES: CS(=O)(=O)c1cccc(NC(=O)Nc2ccc(-n3c4c(c5ncnc(N)c53)CCC4)cc2)c1] |
| 73 | 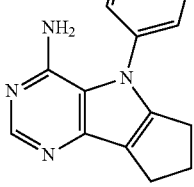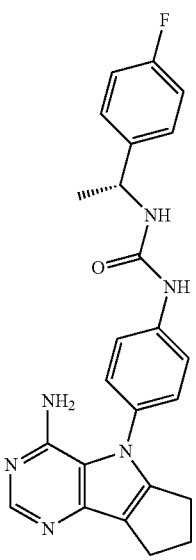 |
| 74 | 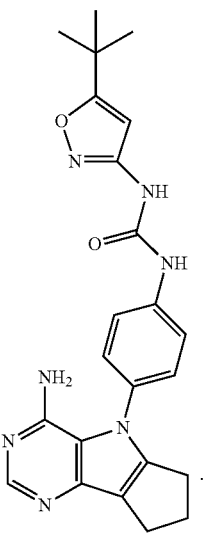 [SMILES: CC(C)(C)c1cc(NC(=O)Nc2ccc(-n3c4c(c5ncnc(N)c53)CCC4)cc2)no1] |
6. The compound according to claim 5, wherein the compound is selected from the group consisting of compounds 1, 2, 18, 24, 25, 31, 32, 60 and 61.

7. The compound according to claim 5, wherein the compound is selected from the group consisting of compounds 3, 5, 6, 7, 8, 9, 10, 12, 15, 26, 29, 34, 37, 40, 49 and 51.

8. The compound according to claim 5, wherein the compound is selected from the group consisting of compounds 14, 16, 17, 20, 21, 23, 30, 33, 36, 39, 41, 44, 45, 46, 47, 50, 55, 57, 58, 59, 62, 63, 64, 66, 67, 68, 69, 72 and 73.

9. The compound according to claim 5, wherein the compound is selected from the group consisting of compounds 11, 13, 19, 27, 28, 35, 43, 48, 54, 56 and 74.

10. A pharmaceutical composition comprising a compound of claim 1 and a pharmaceutically acceptable carrier or diluent.

11. A method of modulating a target kinase function comprising administering a pharmaceutical composition of claim 10.

12. The method according to claim 11, wherein the target kinase function is a function of kinase selected from the group consisting of PDGFR, FGFR, and VEGFR.

13. The method according to claim 12, wherein the kinase is cFMS, Flt3, KDR, FGFR1 or Tie2.

14. A method of treating a patient, comprising the step of administering a compound according to claim 1 to the patient, thereby modulating the function of a protein kinase.

15. The method according to claim 14, wherein the protein kinase is selected from the group consisting of PDGFR, FGFR and VEGFR.

16. The method according to claim 14, wherein the protein kinase is selected from the group consisting of cFMS, Flt3, KDR, FGFR1 and Tie2.

17. A probe comprising a compound of claim 1 and a detectable label or affinity tag for said compound.

18. The probe according to claim 17, wherein the detectable label is selected from a fluorescent moiety, a chemiluminescent moiety, a paramagnetic contrast agent, a metal chelate, a radioactive isotope-containing moiety, and biotin.

19. A method of modulating target kinase function comprising contacting a cell with a compound of claim 1 in an amount sufficient to modulate the target kinase function, whereby the target kinase activity and signaling is modulated.

20. A process for preparing a compound of formula i-e, comprising the steps of:
(a) alkylation of R¹NH₂ with bromoacetonitrile to provide intermediate i-a

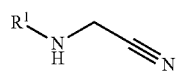

(b) condensation of i-a with i-b in the presence of an acid to provide intermediate i-c

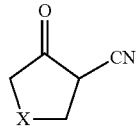

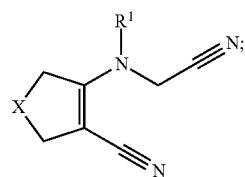

(c) treatment of intermediate i-c with a base to provide intermediate i-d

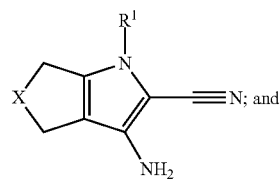

(d) treatment of intermediate i-d with formamidine acetate in an alcohol to provide a compound of formula i-e

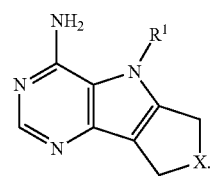

* * * * *